US011980671B2

(12) United States Patent
Bursac et al.

(10) Patent No.: US 11,980,671 B2
(45) Date of Patent: May 14, 2024

(54) USE OF BACTERIAL VOLTAGE GATED ION CHANNELS FOR HUMAN THERAPIES

(71) Applicant: Duke University, Durham, NC (US)

(72) Inventors: Nenad Bursac, Durham, NC (US); Hung Nguyen, Durham, NC (US); Robert Kirkton, Durham, NC (US)

(73) Assignee: Duke University, Durham, NC (US)

( * ) Notice: Subject to any disclaimer, the term of this patent is extended or adjusted under 35 U.S.C. 154(b) by 506 days.

(21) Appl. No.: 16/046,939

(22) Filed: Jul. 26, 2018

(65) Prior Publication Data

US 2019/0030186 A1 Jan. 31, 2019

Related U.S. Application Data

(60) Provisional application No. 62/557,957, filed on Sep. 13, 2017, provisional application No. 62/537,289, filed on Jul. 26, 2017.

(51) Int. Cl.

| | |
|---|---|
| *A61K 48/00* | (2006.01) |
| *A61P 9/06* | (2006.01) |
| *A61P 9/10* | (2006.01) |
| *C07K 14/195* | (2006.01) |
| *C12N 15/113* | (2010.01) |
| *C12N 15/31* | (2006.01) |
| *C12N 15/864* | (2006.01) |

(52) U.S. Cl.
CPC ...... *A61K 48/0058* (2013.01); *A61K 48/0008* (2013.01); *A61K 48/0083* (2013.01); *A61P 9/06* (2018.01); *A61P 9/10* (2018.01); *C07K 14/195* (2013.01); *A61K 48/0075* (2013.01); *C12N 2750/14143* (2013.01)

(58) Field of Classification Search
None
See application file for complete search history.

(56) References Cited

U.S. PATENT DOCUMENTS

| | | |
|---|---|---|
| 4,554,101 A | 11/1985 | Hopp |
| 5,580,859 A | 12/1996 | Felgner et al. |
| 5,679,647 A | 10/1997 | Carson et al. |
| 5,703,055 A | 12/1997 | Felgner et al. |

OTHER PUBLICATIONS

Mathur et al, In Vitro Cardiac Tissue Models: Current Status and Future Prospects, Adv Drug Deliv Rev. Jan. 15, 2016; 96: 203-213.*
Ishikawa, Human Cardiac Gene Therapy, Circ Res. 2018;123:601-613.*
Wolfram et al, Gene Therapy to Treat Cardiovascular Disease, Journal of the American Heart Association, 2013, pp. 1-11.*
Cannata, Gene Therapy for the Heart, Circulation Research. 2020;126:1394-1414.*
Fumoto et al, Targeted Gene Delivery: Importance of Administration Routes, Chapter 1, Intech, 2013, pp. 3-31.*
Abbaci et al., "Gap junctional intercellular communication capacity by gap-FRAP technique: a comparative study," Biotechnol. J., 2007, 2, 50-61.
Arrigoni et al., "Unfolding of a temperature-sensitive domain controls voltage-gated channel activation," Cell, 2016, 164, 922-936.
Badie et al., "Conduction block in micropatterned cardiomyocyte cultures replicating the structure of ventricular cross-sections," Cardiovasc. Res., 2012, 93, 263-271.
Badie et al., "Novel micropatterned cardiac cell cultures with realistic ventricular microstructure," Biophys. J., 2009, 96, 3873-3885.
Bagneris et al., "Prokaryotic NavMs channel as a structural and functional model for eukaryotic sodium channel antagonism," Proc. Natl Acad. Sci. USA, 2014, 111, 8428-8433.
Bagneris et al., "Structural model of the open-closed-inactivated cycle of prokaryotic voltage-gated sodium channels," J. Gen. Physiol., 2015, 145, 5-16.
Bando et al., "Control of spontaneous Ca2+ transients is critical for neuronal maturation in the developing neocortex," Cereb. Cortex, 2014, 26, 106-117.
Black et al., "Noncanonical roles of voltage-gated sodium channels," Neuron, 2013, 80, 280-291.
Blanchet et al., "Acidic residues on the voltage-sensor domain determine the activation of the NaChBac sodium channel," Biophys. J., 2007, 92, 3513-3523.
Bocelli-Tyndall et al., "Human articular chondrocytes suppress in vitro proliferation of anti-CD3 activated peripheral blood mononuclear cells," Journal of cellular physiology, 2006, 209(3): 732-4.
Boink et al., "HCN2/SkM1 gene transfer into canine left bundle branch induces stable, autonomically responsive biological pacing at physiological heart rates," J. Am. Coll. Cardiol., 2013, 61, 1192-1201.
Bonifacino et al., "Signals for sorting of transmembrane proteins to endosomes and lysosomes," Annu Rev Biochem, 2003, 72, 395-447.
Boshart et al., "A very strong enhancer is located upstream of an immediate early gene of human cytomegalovirus," Cell, 1985, 41, 521-30.
Bulman et al., "A novel sodium channel mutation in a family with hypokalemic periodic paralysis," Neurology, 1999, 53, 1932-1936.
Bursac et al., "Multiarm spirals in a two-dimensional cardiac substrate," Proc. Natl Acad. Sci. USA, 2004, 101, 15530-15534.
Bursac, "Bioengineering Cardiac Regeneration and Repair," ICENet 2014, Dolgoprudny, Russia, May 28, 2014 (20 pages).
Bursac, "Engineering of Human Excitable Tissues," Northwestern University, Evanston, IL, Nov. 20, 2014 (23 pages).
Bursac, "Engineering Patches and Fibroblasts for Cardiac Therapy," Department of Biomedical Engineering, UAB, Mar. 19, 2016 (17 pages).

(Continued)

*Primary Examiner* — Maria Marvich
(74) *Attorney, Agent, or Firm* — Michael Best & Friedrich LLP

(57) ABSTRACT

Disclosed herein are compositions including prokaryotic ion channel polypeptides and methods of treating voltage gated ion channel-related condition such as heart arrhythmia, chronic atrial fibrillation, damage from myocardial infarction, damage from stroke, and chronic ischemia.

9 Claims, 14 Drawing Sheets

Specification includes a Sequence Listing.

(56) References Cited

OTHER PUBLICATIONS

Bursac, "Excitable Tissue Engineering and Repair," George Washington University, Washington, DC, Apr. 7, 2015 (24 pages).
Bursac, "In Vitro Engineered Myocardium for Cardiac Repair," Transdifferentiantion and Tissue Plasticity in Cardiovascular Rejuvenation, Wiston House, Feb. 7, 2016 (8 pages).
Bursac, "Somatic and Stem Cell Engineering for Cardiac Repair," DCL Series, UCLA, Los Angeles, CA, May 11, 2015 (25 pages).
C.T.F.A. Cosmetic Ingredient Handbook, 1992, pp. 587-592.
Carmeliet, "Cardiac ionic currents and acute ischemia: from channels to arrhythmias," Physiol. Rev., 1999, 79, 917-1017.
Catterall et al., "International Union of Pharmacology. XLVII. Nomenclature and structure-function relationships of voltage-gated sodium channels," Pharmacol Rev, 2005, 57, 397-409.
Catterall, "From ionic currents to molecular mechanisms: the structure and function of voltage-gated sodium channels," Neuron, 2000, 26, 13-25.
Cerrone et al., "Sodium current deficit and arrhythmogenesis in a murine model of plakophilin-2 haploinsufficiency," Cardiovasc Res, 2012, 95(4): 460-8.
Charalambous et al., "NaChBac: the long lost sodium channel ancestor," Biochemistry, 2011, 50, 6742-6752.
Cho et al., "Biological therapies for cardiac arrhythmias: can genes and cells replace drugs and devices?," Circ. Res., 2010, 106, 674-685.
Chong et al., "Human embryonic-stem-cell-derived cardiomyocytes regenerate non-human primate hearts," Nature, 2014, 510, 273-277.
Corry et al., "Pharmacological insights and quirks of bacterial sodium channels," Handb. Exp. Pharmacol., 2014, 221, 251-267.
Cox et al., "Therapeutic genome editing: prospects and challenges," Nat. Med., 2015, 21, 121-131.
Danik et al., "Modulation of cardiac gap junction expression and arrhythmic susceptibility," Circ. Res., 2004, 95, 1035-1041.
de Bakker et al., "Slow conduction in the infarcted human heart. 'Zigzag' course of activation," Circulation, 1993, 88, 915-926.
de Diego et al., "Electrophysiological consequences of acute regional ischemia/reperfusion in neonatal rat ventricular myocyte monolayers," Circulation, 2008, 118, 2330-2337.
Deisseroth, "Optogenetics: 10 years of microbial opsins in neuroscience," Nat. Neurosci., 2015, 18, 1213-1225.
Di Nicola et al., "Human bone marrow stromal cells suppress T-lymphocyte proliferation induced by cellular or nonspecific mitogenic stimuli," Blood, 2002, 99(10): 3838-43.
Dijkema et al., "Cloning and expression of the chromosomal immune interferon gene of the rat," EMBO J., 1985, 4, 761-767.
Donnelly et al., "DNA vaccines," Ann. Rev. Immunol., 1997, 15, 617-648.
George Jr., "Inherited disorders of voltage-gated sodium channels," J Clin Invest, 2005, 115, 1990-1999.
Goddard et al., "Physiological consequences of the P2328S mutation in the ryanodine receptor (RyR2) gene in genetically modified murine hearts," Acta Physiol 2008, 194(2): 123-40.
Gorman et al., "The Rous sarcoma virus long terminal repeat is a strong promoter when introduced into a variety of eukaryotic cells by DNA-mediated transfection," Proc. Natl. Acad. Sci. USA, 1982, 79, 6777-6781.
Grossmann et al., "Requirement of plakophilin 2 for heart morphogenesis and cardiac junction formation," J Cell Biol, 2004, 167(1): 149-60.
Hakim et al., "Scn3b knockout mice exhibit abnormal ventricular electrophysiological properties," Prog Biophys Mol Biol, 2008, 98(2-3): 251-66.
Han et al., "Deletion of PDK1 causes cardiac sodium current reduction in mice," PLoS One, 2015, 10(3): e0122436.
Haniffa et al., "Adult human fibroblasts are potent immunoregulatory cells and functionally equivalent to mesenchymal stem cells," Journal of immunology, 2007, 179(3): 1595-604.

Hanks et al., "The eukaryotic protein kinase superfamily: kinase (catalytic) domain structure and classification," FASEB J., 1995, 9, 576-596.
Heagerty et al., "Time-dependent ROC curves for censored survival data and a diagnostic marker," Biometrics, 2000, 56, 337-44.
Hodgkin et al., "Propagation of electrical signals along giant nerve fibers," Proc. R. Soc. Lond. B, 1952, 140, 177-183.
Hodgkin et al., "The electrical constants of a crustacean nerve fibre," Proc. R. Soc. Med., 1946, 134, 444-479.
Hofherr et al., "Selective Golgi export of Kir2.1 controls the stoichiometry of functional Kir2.x channel heteromers," J Cell Sci, 2005, 118, 1935-1943.
Hou et al., "Genetically engineered excitable cardiac myofibroblasts coupled to cardiomyocytes rescue normal propagation and reduce arrhythmia complexity in heterocellular monolayers," PLoS ONE, 2013, 8, e55400.
Hu et al., "Generation of a stable mammalian cell line for simultaneous expression of multiple genes by using 2A peptide-based lentiviral vector," Biotechnol. Lett., 2009, 31, 353-359.
Hu et al., "Mutations in SCN10A are responsible for a large fraction of cases of Brugada syndrome," J. Am. Coll. Cardiol., 2014, 64, 66-79.
Irie et al., "Comparative study of the gating motif and C-type inactivation in prokaryotic voltage-gated sodium channels," J. Biol. Chem., 2010, 285, 3685-3694.
Janse et al., "Electrophysiological mechanisms of ventricular arrhythmias resulting from myocardial ischemia and infarction," Physiol. Rev., 1989, 69, 1049-1169.
Jurkat-Rott et al., "Voltage-sensor sodium channel mutations cause hypokalemic periodic paralysis type 2 by enhanced inactivation and reduced current," Proc. Natl Acad. Sci. USA, 2000, 97, 9549-9554.
Kamiya et al., "A nonsense mutation of the sodium channel gene SCN2A in a patient with intractable epilepsy and mental decline," J. Neurosci, 2004, 24, 2690-2698.
Kapplinger et al., "An international compendium of mutations in the SCN5A-encoded cardiac sodium channel in patients referred for Brugada syndrome genetic testing," Heart Rhythm, 2010, 7, 33-46.
Kim et al., "Use of the human elongation factor 1 alpha promoter as a versatile and efficient expression system," Gene, 1990, 91, 217-23.
King et al., "Loss of Nav1.5 expression and function in murine atria containing the RyR2-P2328S gain-of-function mutation," Cardiovasc Res, 2013, 99(4): 751-9.
Kirkton et al., "Engineering biosynthetic excitable tissues from unexcitable cells for electrophysiological and cell therapy studies." Nat. Commun., 2011, 2, 300.
Kirkton et al., "Genetic engineering of somatic cells to study and improve cardiac function," Europace, 2012, 14(Suppl 5): v40-v49.
Klinger et al., "Cardiac cell therapy in vitro: reproducible assays for comparing the efficacy of different donor cells," IEEE Eng. Med. Biol. Mag., 2008, 27, 72-80.
Koishi et al., "A superfamily of voltage-gated sodium channels in bacteria," J. Biol. Chem., 2004, 279, 9532-9538.
Kyte et al., "A simple method for displaying the hydropathic character of a protein," J. Mol. Biol., 1982, 157, 105-132.
Lau et al., "Epicardial border zone overexpression of skeletal muscle sodium channel SkM1 normalizes activation, preserves conduction, and suppresses ventricular arrhythmia: an in silico, in vivo, in vitro study," Circulation, 2009, 119, 19-27.
Liao et al., "Proarrhythmic risk of embryonic stem cell-derived cardiomyocyte transplantation in infarcted myocardium," Heart Rhythm, 2010, 7, 1852-1859.
Lin et al., "Genetically increased cell-intrinsic excitability enhances neuronal integration into adult brain circuits," Neuron, 2010, 65, 32-39.
Lossin et al., "Epilepsy-associated dysfunction in the voltage-gated neuronal sodium channel SCN1A," J. Neurosci, 2003, 23, 11289-11295.
Luo et al., "A model of the ventricular cardiac action potential. Depolarization, repolarization, and their interaction," Circ Res, 1991, 68, 1501-1526.

(56) References Cited

OTHER PUBLICATIONS

Makara et al., "Ankyrin-G coordinates intercalated disc signaling platform to regulate cardiac excitability in vivo," Circ Res, 2014, 115(11): 929-38.
Maniatis et al., "Regulation of inducible and tissue-specific gene expression," Science, 1987, 236: 1237-45.
Martin, "Wound healing—aiming for perfect skin regeneration," Science, 1997, 276, 75-81.
Mayer et al., "Signalling through SH2 and SH3 domains," Trends Cell. Biol., 1993, 3, 8-13.
McCusker et al., "Structure of a bacterial voltage-gated sodium channel pore reveals mechanisms of opening and closing," Nat. Commun., 2012, 3, 1102.
McCutcheon's vol. 1, Emulsifiers & Detergents, 1994, North American Edition, pp. 236-239.
McSpadden et al., "Electrotonic loading of anisotropic cardiac monolayers by unexcitable cells depends on connexin type and expression level," Am. J. Physiol. Cell. Physiol., 2009, 297, C339-C351.
Mehdi et al., "Abstract 17871: Brugada Phenotype in Cardiac-Specific GPD1-L Knockout Mice," Circulation, 2014, 130(Suppl 2): A17871, 2 pages.
Mizushima et al., "pEF-BOS, a powerful mammalian expression vector," Nuc. Acids. Res., 1990, 18, 5322.
Nguyen et al., "Actively Conducting Human Fibroblast Tissues for Cardiac Therapy," Poster presented at conference in Durham, NC, Oct. 13, 2014.
Nguyen et al., "Engineering Primary Human Fibroblasts with Customizable Electrical Phenotypes," Tampa, FL, Oct. 8, 2015.
Nguyen et al., "Engineering prokaryotic channels for control of mammalian tissue excitability," Nat Commun, 2016, 7, 13132.
Nguyen et al., "Gene and Cell Therapies for Heart Disease using Electrically Active Fibroblasts," Poster presented at the American Society of Gene and cell Therapy meeting, May 22, 2014.
Nguyen et al., "Generation of Actively Conducting 3D Human Fibroblast Tissues for Cardiac Therapy," Poster presented at conference in Durham, NC, Oct. 13, 2014.
Nguyen et al., "Genetic engineering of actively conducting human fibroblasts" Poster presented at the Heart Rhythm Society scientific session, May 8, 2014.
Nygren et al., "Mathematical model of an adult human atrial cell: the role of K+ currents in repolarization," Circ. Res., 1998, 82, 63-81.
Papadatos et al., "Slowed conduction and ventricular tachycardia after targeted disruption of the cardiac sodium channel gene Scn5a," Proc Natl Acad Sci U S A, 2002, 99(9): 6210-5.
Payandeh et al., "Bacterial Voltage-Gated Sodium Channels (BacNas) from the Soil, Sea, and Salt Lakes Enlighten Molecular Mechanisms of Electrical Signaling and Pharmacology in the Brain and Heart," J. Mol. Biol., 2014, 427, 3-30.
Payandeh et al., "The crystal structure of a voltage-gated sodium channel," Nature, 2011, 475, 353-358.
Pilichou et al., "Myocyte necrosis underlies progressive myocardial dystrophy in mouse dsg2-related arrhythmogenic right ventricular cardiomyopathy," J Exp Med, 2009, 206(8): 1787-802.
Pitts et al., "Coverslip hypoxia: a novel method for studying cardiac myocyte hypoxia and ischemia in vitro," Am. J. Physiol. Heart Circ. Physiol., 2004, 287, H1801-H1812.
Protas et al., "Expression of skeletal but not cardiac Na+ channel isoform preserves normal conduction in a depolarized cardiac syncytium," Cardiovasc. Res., 2009, 81, 528-535.
Quah et al., "Monitoring lymphocyte proliferation in vitro and in vivo with the intracellular fluorescent dye carboxyfluorescein diacetate succinimidyl ester," Nature protocols, 2007, 2(9): p. 2049-2056.
Remington's Pharmaceutical Sciences, 15th Ed. 1975, pp. 335-337.
Ren et al., "A prokaryotic voltage-gated sodium channel," Science, 2001, 294, 2372-2375.
Rizzo et al., "Intercalated disc abnormalities, reduced Na(+) current density, and conduction slowing in desmoglein-2 mutant mice prior to cardiomyopathie changes," Cardiovasc Res, 2012, 95(4): 409-18.
Rog-Zielinska et al., "The living scar—cardiac fibroblasts and the injured heart," Trends Mol. Med., 2016, 22, 99-114.
Sadowski et al., "A noncatalytic domain conserved among cytoplasmic protein-tyrosine kinases modifies the kinase function and transforming activity of Fujinami sarcoma virus P130gag-fps," Mol. Cell. Bio., 1986, 6, 4396-4408.
Sanders et al., "De novo mutations revealed by whole-exome sequencing are strongly associated with autism," Nature, 2012, 485, 237-241.
Scheuer, "Bacterial sodium channels: models for eukaryotic sodium and calcium channels," Handb. Exp. Pharmacol., 2014, 221, 269-291.
Severs et al., "Remodelling of gap junctions and connexin expression in diseased myocardium," Cardiovasc. Res., 2008, 80, 9-19.
Shaw et al., "Ionic mechanisms of propagation in cardiac tissue. Roles of the sodium and L-type calcium currents during reduced excitability and decreased gap junction coupling, " Circ. Res., 1997, 81, 727-741.
Shaya et al., "Structure of a prokaryotic sodium channel pore reveals essential gating elements and an outer ion binding site common to eukaryotic channels," J. Mol. Biol., 2014, 426, 467-483.
Shaya et al., "Voltage-gated sodium channel (NaV) protein dissection creates a set of functional pore-only proteins," Proc. Natl Acad. Sci. USA, 2011, 108, 12313-12318.
Shimomura et al., "Arrangement and mobility of the voltage sensor domain in prokaryotic voltage-gated sodium channels," J. Biol. Chem., 2011, 286, 7409-7417.
Shy et al., "PDZ domain-binding motif regulates cardiomyocyte compartment-specific NaV1.5 channel expression and function," Circulation, 2014, 130(2): 147-60.
Subramanyam et al., "Manipulating L-type calcium channels in cardiomyocytes using split-intein protein transsplicing," Proc. Natl Acad. Sci. USA, 2013, 110, 15461-15466.
Tang et al., "Structural basis for Ca2+ selectivity of a voltage-gated calcium channel," Nature, 2014, 505, 56-61.
ten Tusscher et al., "A model for human ventricular tissue," Am. J. Physiol. Heart Circ. Physiol., 2004, 286, H1573-H1589.
Uetsuki et al., "Isolation and characterization of the human chromosomal gene for polypeptide chain elongation factor-1 alpha," J. Biol. Chem., 1989, 264, 5791-5798.
Voss et al., "The role of enhancers in the regulation of cell-type-specific transcriptional control," Trends Biochem. Sci., 1986, 11: 287-289.
Wada et al., "Human foreskin fibroblasts exert immunomodulatory properties by a different mechanism to bone marrow stromal/stem cells," Stem cells and development, 2011, 20(4): 647-59.
Wade et al., "A fluorescence photobleaching assay of gap junction-mediated communication between human cells," Science, 1986, 232, 525-528.
Weiss et al., "Loss-of-function mutations in sodium channel Nav1.7 cause anosmia," Nature, 2011, 472, 186-190.
Welch et al., "Design parameters to control synthetic gene expression in *Escherichia coli*," PLoS One, 2009, 4, e7002.
Yue et al., "The cation selectivity filter of the bacterial sodium channel, NaChBac," J. Gen. Physiol., 2002, 120, 845-853.
Zacharias et al., "Partitioning of lipid-modified monomeric GFPs into membrane microdomains of live cells," Science, 2002, 296, 913-916.
Zhang et al., "Crystal structure of an orthologue of the NaChBac voltage-gated sodium channel," Nature, 2012, 486, 130-134.

\* cited by examiner

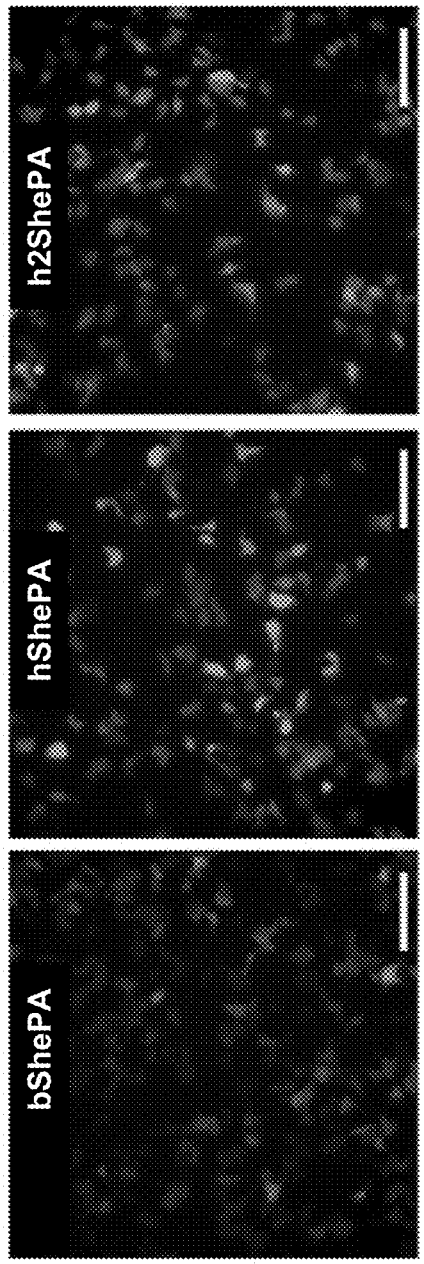
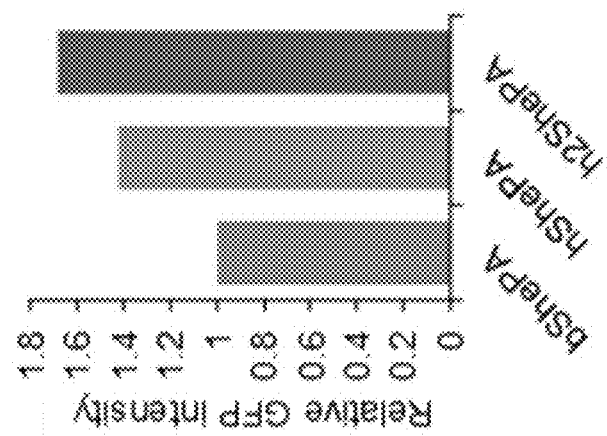
FIG. 1A
FIG. 1B

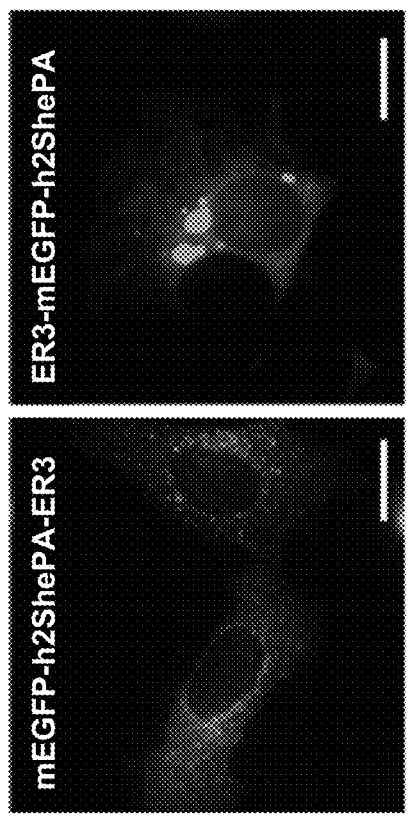
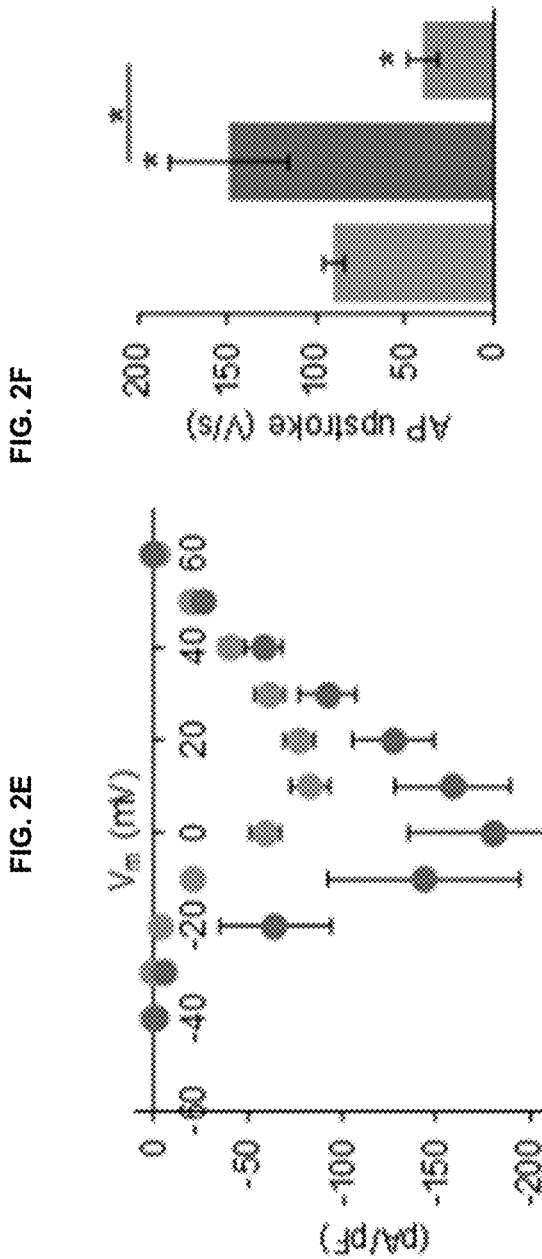
FIG. 2E
FIG. 2F
FIG. 2G
FIG. 2H

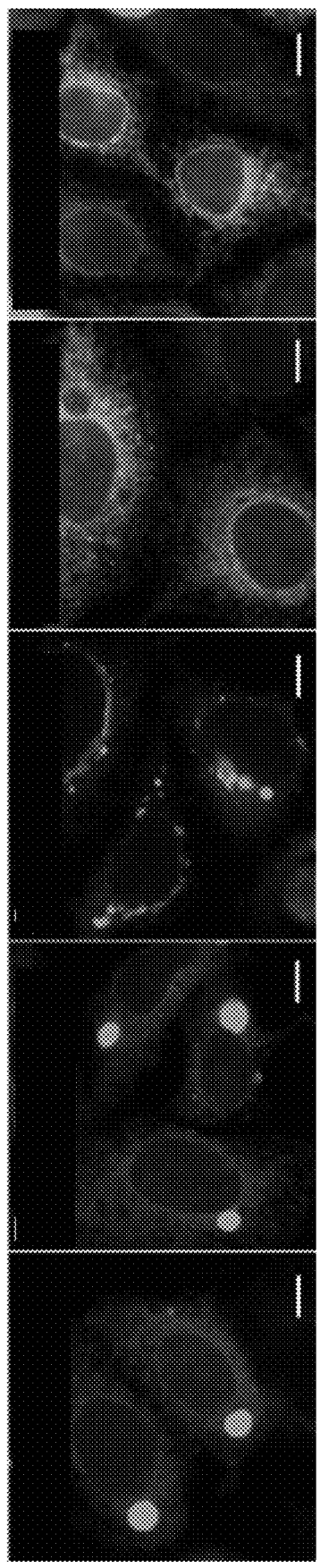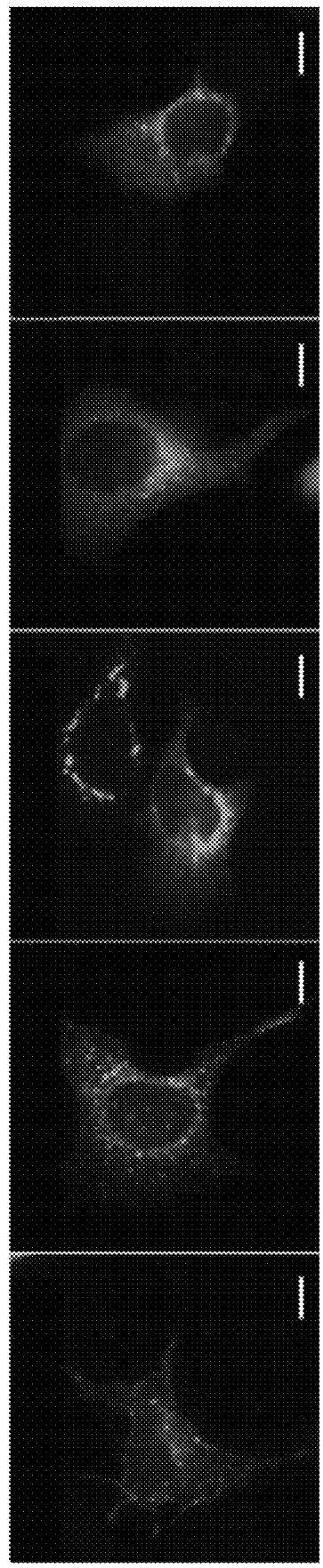

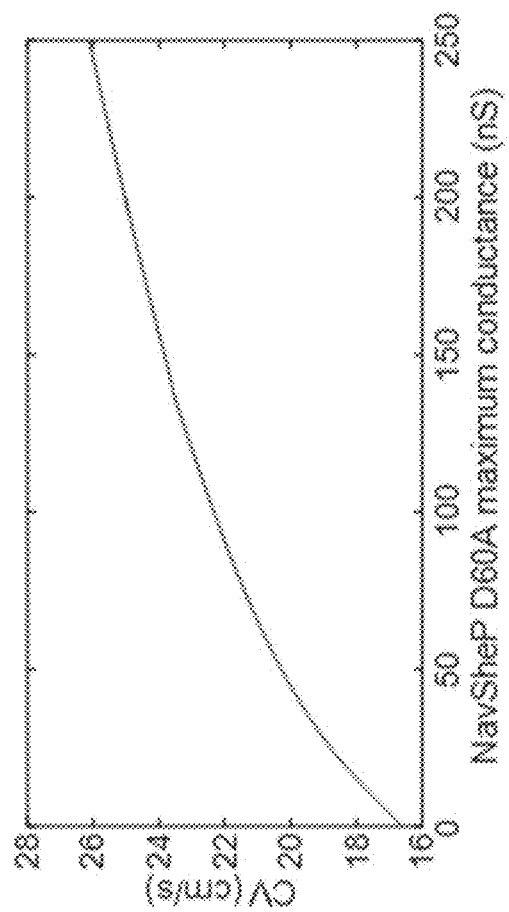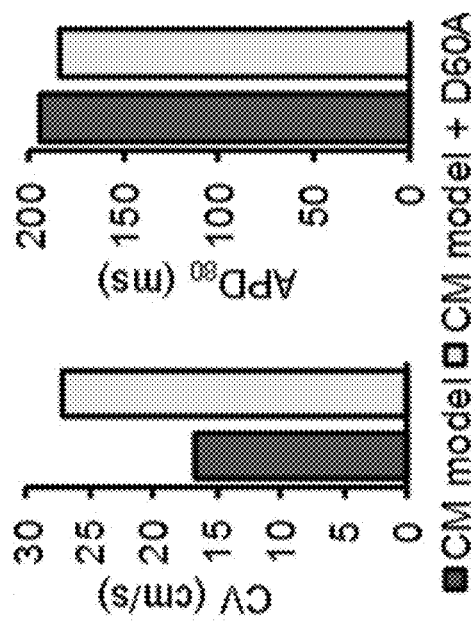
FIG. 4F
FIG. 4G
FIG. 4H

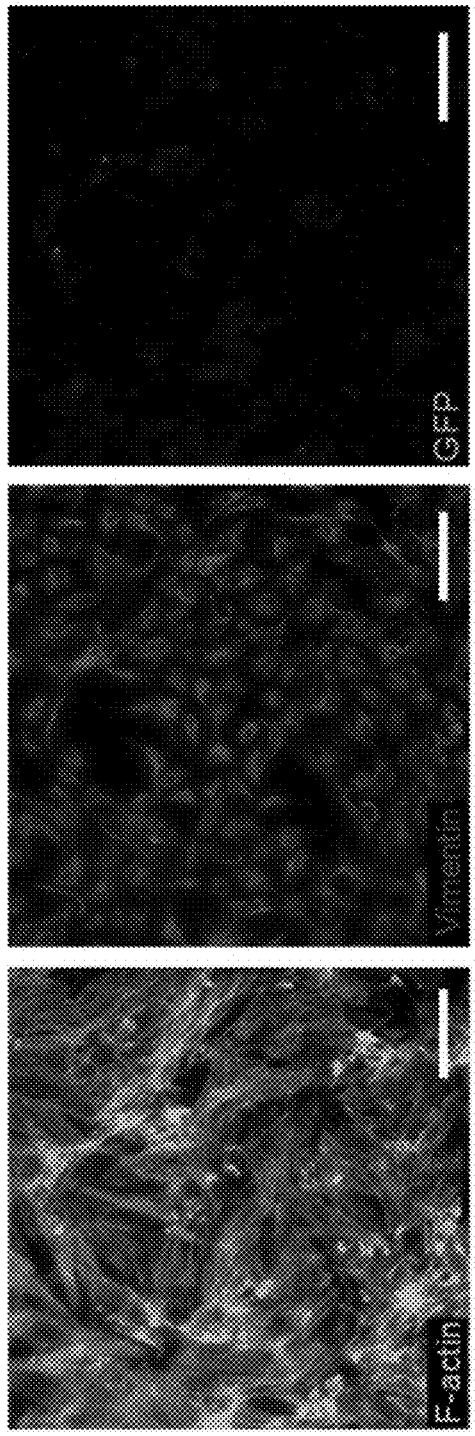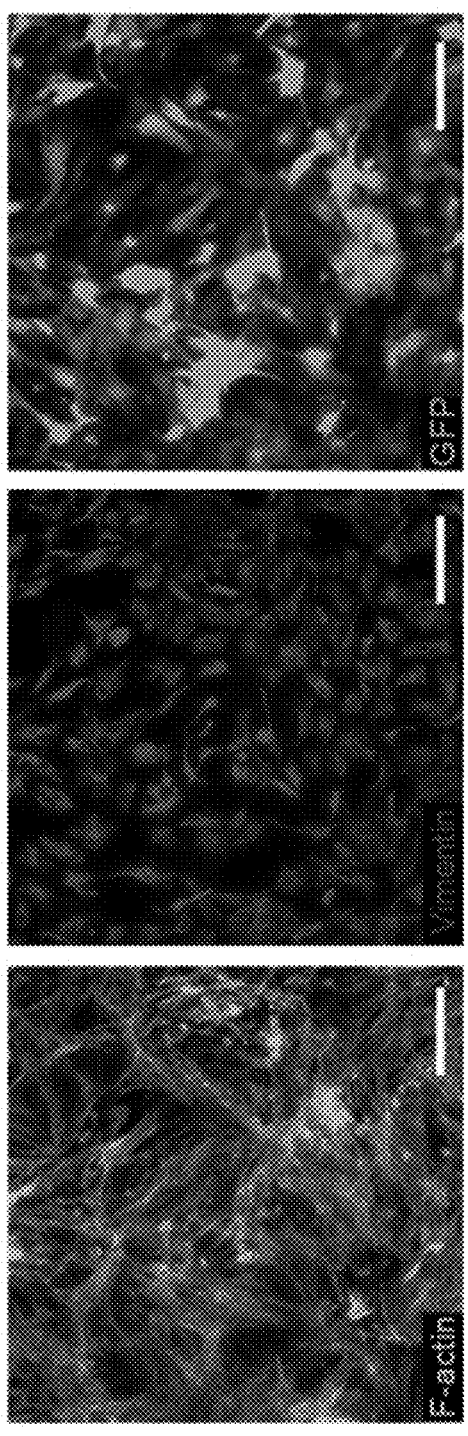
FIG. 5A
FIG. 5B

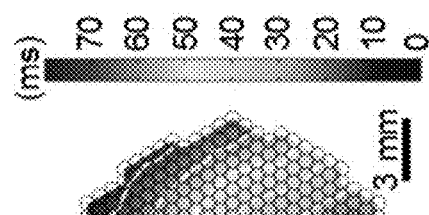
FIG. 5C
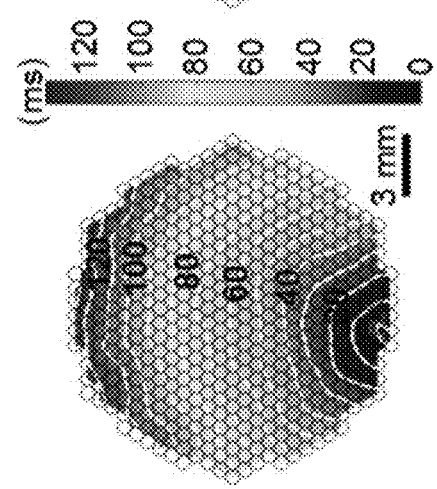
FIG. 5D
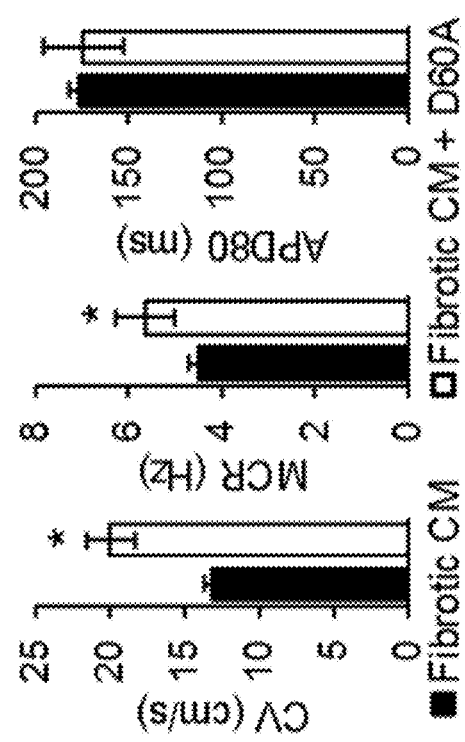
FIG. 5E
FIG. 5F
FIG. 5G

SEQUENCE LISTING

<160> NUMBER OF SEQ ID NOS: 27

<210> SEQ ID NO 1
<211> LENGTH: 888
<212> TYPE: DNA
<213> ORGANISM: Artificial sequence
<220> FEATURE:
<223> OTHER INFORMATION: Synthetic

<400> SEQUENCE: 1

```
atgagtacat ctttacttaa cgcgccaacg ggtttgcagg cacgagtgat taacttggtt      60
gagcaaaact ggtttggtca ttttattttg gcattgattt taatcaacgc ggtgcagtta     120
ggtatggaga cctcagccag cctgatggcg caatacggta cttgttgat gagtcttgat     180
```

```
aagttgctac tgagtgtatt tgtggtggag ttattgctgc ggatttatgc ctacagggggg    240 aaattttta aagacccttg gagcgtgttc gattttaccg tgatagtgat agcactgatc     300
cctgcatctg ggccattggc tgtcctgcgt tcgctcaggg tattgcgggt gctgagagtg    360
ttaacaattg tgccatcaat gaaacgggtg tgtctgcgc tgttgggatc acttcctgga    420
ttggcatcga tcgccacggt attactgttg atttattatg tgtttgcggt gattgctacc    480 aaaattttg gcgatgcatt ccctgaatgg tttggcacta ttgctgactc attttatacc     540
ctatttcaaa taatgacgct tgaaagctgg tctatgggaa tttcgcggcc agtgatggaa    600 gtgtacccctt atgcttgggt attttctgta ccatttattc tggtagcgac tttcacaatg   660
ctaaatttgt ttattgcgat tatcgtcaat accatgcaaa ccttcagcga cgaagagcat    720
gcattagagc gtgaacaaga caaacaaatc ttagagcagg aacaaagaca aatgcacgag    780
gagttgaaag ccatcagact cgagctacaa caattacaaa ccttgttgcg caatgctgct    840
ggtgattctt ctaatgtgtc gacaagggga aacattggtt ctgactga               888
```

```
<210> SEQ ID NO 2
<211> LENGTH: 888
<212> TYPE: DNA
<213> ORGANISM: Artificial sequence
<220> FEATURE:
<223> OTHER INFORMATION: Synthetic

<400> SEQUENCE: 2
```

```
atgtcaacct cactgctgaa cgctccaact gggctgcagg caagagtcat caatctggtc    60
gaacagaact ggtttgggca ctttattctg gcactgatcc tgattaacgc agtgcagctg   120
ggaatggaga ccagcgcctc cctgatggca cagtacggaa cactgctgat gtccctggca   180
aagctgctgc tgagcgtgtt cgtggtcgaa ctgctgctgc gaatctacgc ctatcggggc    240
aagttcttta aagacccctg gagcgtgttc gacttcaccg tgatcgtcat tgccctgatt   300
ccagctagtg gacctctggc cgtgctgcgg tcactgagag tgctgagggt cctgcgcgtg    360
ctgacaatcg tgcctagcat gaagagggtg gtctcagctc tgctgggcag cctgccagga    420
ctggcatcca tcgctactgt gctgctgctg atctactatg tcttcgcagt gatcgccact    480
aaaattttcg gagacgcttt tcccgagtgg ttcggcacca tcgcagattc ttttttataca   540 ctgttccaga tcatgactct ggagtcttgg agtatgggca tcagtcgccc agtcatggaa    600
gtgtacccct atgcctgggt cttctttgtg ccttttattc tggtcgccac cttcacaatg    660
ctgaacctgt ttatcgctat cattgtgaat actatgcaga cctttagcga cgaggaacac    720
gctctggagc gagaacagga taagcagatt ctggagcagg aacagagaca gatgcatgag    780
gaactgaaag caatcaggct ggagctgcag cagctgcaga cactgctgag aaacgctgct    840
ggcgattcat caaacgtgtc cactaaagga aacattggct ctgactga               888
```

```
<210> SEQ ID NO 3
<211> LENGTH: 888
<212> TYPE: DNA
<213> ORGANISM: Artificial sequence
<220> FEATURE:
<223> OTHER INFORMATION: Synthetic

<400> SEQUENCE: 3
```

```
atgtcaacct cccttctgaa cgcccccacc ggtctgcaag cccgcgtcat caacctggtc    60
gaacagaact ggttcggcca cttcatcctg gcactgattc tcattaacgc cgtgcagctt   120
```

```
ggaatggaaa ctagcgcgtc cctgatggct caatacggca cactgctcat gagcctggcg    180
aagctgctcc tgtccgtgtt cgtggtggaa ctgttgctgc ggatctatgc gtaccgcgga    240
aaattcttca aggatccatg gagcgtgttc gactttactg tgattgtgat cgcactcatc    300
ccggcctcgg gaccgctcgc cgtgctccgg tcactgagag tcctgagggt gctcagagtg    360
ctgaccattg tgcctagcat gaagcgcgtg gtgtccgccc tgttgggatc cctgccgggt    420
ttggcttcga ttgccactgt gctgctcctg atctactacg tgttcgccgt cattgccact    480
aagattttcg gcgacgcctt tcctgagtgg ttcggaacca tcgctgactc tttctacacc    540
ttgttccaaa tcatgaccct ggaatcctgg tccatgggga tttcgaggcc cgtgatggag    600
gtgtacccct acgcctgggt gttcttcgtc cccttcatcc ttgtcgcaac cttcaccatg    660
cttaacctgt ttatcgccat catcgtgaac acgatgcaga ccttctccga tgaagaacat    720
gcgctggagc gggaacagga caagcagatc ctggagcagg aacagcggca gatgcacgag    780
gagctgaagg ccatccggct ggagctgcag cagctccaaa ctctgctgcg caacgcggcc    840
ggagattcaa gcaatgtgtc gaccaagggg aacatcggct ccgactga               888
```

<210> SEQ ID NO 4
<211> LENGTH: 6
<212> TYPE: PRT
<213> ORGANISM: Artificial sequence
<220> FEATURE:
<223> OTHER INFORMATION: Synthetic

<400> SEQUENCE: 4

Gly Val Lys Glu Ser Leu
1               5

<210> SEQ ID NO 5
<211> LENGTH: 6
<212> TYPE: PRT
<213> ORGANISM: Artificial sequence
<220> FEATURE:
<223> OTHER INFORMATION: Synthetic

<400> SEQUENCE: 5

Asp Leu Arg Arg Ser Leu
1               5

<210> SEQ ID NO 6
<211> LENGTH: 7
<212> TYPE: PRT
<213> ORGANISM: Artificial sequence
<220> FEATURE:
<223> OTHER INFORMATION: Synthetic

<400> SEQUENCE: 6

Phe Cys Tyr Glu Asn Glu Val
1               5

<210> SEQ ID NO 7
<211> LENGTH: 6
<212> TYPE: PRT
<213> ORGANISM: Artificial sequence
<220> FEATURE:
<223> OTHER INFORMATION: Synthetic

<400> SEQUENCE: 7

Leu Glu Ser Trp Ser Met
1               5

```
<210> SEQ ID NO 8
<211> LENGTH: 6
<212> TYPE: PRT
<213> ORGANISM: Artificial sequence
<220> FEATURE:
<223> OTHER INFORMATION: Synthetic

<400> SEQUENCE: 8

Leu Asp Asp Trp Ser Asp
1               5

<210> SEQ ID NO 9
<211> LENGTH: 3
<212> TYPE: PRT
<213> ORGANISM: Artificial sequence
<220> FEATURE:
<223> OTHER INFORMATION: Synthetic

<400> SEQUENCE: 9

Ser Glu Ile
1

<210> SEQ ID NO 10
<211> LENGTH: 3
<212> TYPE: PRT
<213> ORGANISM: Artificial sequence
<220> FEATURE:
<223> OTHER INFORMATION: Synthetic

<400> SEQUENCE: 10

Ser Ile Val
1

<210> SEQ ID NO 11
<211> LENGTH: 3
<212> TYPE: PRT
<213> ORGANISM: Artificial sequence
<220> FEATURE:
<223> OTHER INFORMATION: Synthetic

<400> SEQUENCE: 11

Thr Asp Val
1

<210> SEQ ID NO 12
<211> LENGTH: 9
<212> TYPE: PRT
<213> ORGANISM: Artificial sequence
<220> FEATURE:
<223> OTHER INFORMATION: Synthetic

<400> SEQUENCE: 12

Val Pro Ile Ala Val Ala Glu Ser Asp
1               5

<210> SEQ ID NO 13
<211> LENGTH: 17
<212> TYPE: PRT
<213> ORGANISM: Artificial sequence
<220> FEATURE:
<223> OTHER INFORMATION: Synthetic

<400> SEQUENCE: 13

Arg Ser Phe Val Lys Lys Asp Gly His Cys Asn Val Gln Phe Ile Asn
1               5                   10                  15

Val
```

```
<210> SEQ ID NO 14
<211> LENGTH: 20
<212> TYPE: PRT
<213> ORGANISM: Artificial sequence
<220> FEATURE:
<223> OTHER INFORMATION: Synthetic

<400> SEQUENCE: 14

Lys Ser Arg Ile Thr Ser Glu Gly Glu Tyr Ile Pro Leu Asp Gln Ile
1               5                   10                  15

Asp Ile Asn Val
            20

<210> SEQ ID NO 15
<211> LENGTH: 1
<212> TYPE: PRT
<213> ORGANISM: Artificial sequence
<220> FEATURE:
<223> OTHER INFORMATION: Synthetic
<220> FEATURE:
<221> NAME/KEY: Gly
<222> LOCATION: (1)..(1)
<223> OTHER INFORMATION: Gly at position 1 may repeat from 1 to 10 times

<400> SEQUENCE: 15

Gly
1

<210> SEQ ID NO 16
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: Gly-Gly-Gly-Gly-Ser
<222> LOCATION: (1)..(5)
<223> OTHER INFORMATION: Gly-Gly-Gly-Gly-Ser at positions 1-5 may
      repeat from 1 to 10 times

<400> SEQUENCE: 16

Gly Gly Gly Gly Ser
1               5

<210> SEQ ID NO 17
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: Glu-Ala-Ala-Ala-Lys
<222> LOCATION: (1)..(5)
<223> OTHER INFORMATION: Glu-Ala-Ala-Ala-Lys at positions 1-5 may
      repeat from 1 to 10 times

<400> SEQUENCE: 17

Glu Ala Ala Ala Lys
1               5

<210> SEQ ID NO 18
<211> LENGTH: 2
<212> TYPE: PRT
<213> ORGANISM: Artificial sequence
<220> FEATURE:
<223> OTHER INFORMATION: Synthetic
<220> FEATURE:
<221> NAME/KEY: Xaa-Pro
<222> LOCATION: (1)..(2)
```

```
<223> OTHER INFORMATION: Xaa-Pro at positions 1-2 may repeat from 1 to
      10 times
<220> FEATURE:
<221> NAME/KEY: Xaa
<222> LOCATION: (1)..(1)
<223> OTHER INFORMATION: Xaa at position 1 is any amino acid

<400> SEQUENCE: 18

Xaa Pro
1

<210> SEQ ID NO 19
<211> LENGTH: 21
<212> TYPE: DNA
<213> ORGANISM: Artificial sequence
<220> FEATURE:
<223> OTHER INFORMATION: Synthetic

<400> SEQUENCE: 19
ttctgctacg agaacgaggt g                                              21

<210> SEQ ID NO 20
<211> LENGTH: 909
<212> TYPE: DNA
<213> ORGANISM: Artificial sequence
<220> FEATURE:
<223> OTHER INFORMATION: Synthetic

<400> SEQUENCE: 20
atgagtacat ctttacttaa cgcgccaacg ggtttgcagg cacgagtgat taacttggtt     60
gagcaaaact ggtttggtca ttttattttg gcattgattt taatcaacgc ggtgcagtta    120
ggtatggaga cctcagccag cctgatggcg caatacggta ctttgttgat gagtcttgat    180
aagttgctac tgagtgtatt tgtggtggag ttattgctgc ggatttatgc ctacaggggg    240 aaattttta aagacccttg gagcgtgttc gattttaccg tgatagtgat agcactgatc    300
cctgcatctg ggccattggc tgtcctgcgt tcgctcaggg tattgcgggt gctgagagtg    360
ttaacaattg tgccatcaat gaaacgggtg gtgtctgcgc tgttgggatc acttcctgga    420
ttggcatcga tcgccacggt attactgttg atttattatg tgtttgcggt gattgctacc    480 aaaattttg gcgatgcatt ccctgaatgg tttggcacta ttgctgactc attttatacc    540
ctatttcaaa taatgacgct tgaaagctgg tctatgggaa tttcgcggcc agtgatggaa    600
gtgtaccctt atgcttgggt attttttcgta ccatttattc tggtagcgac tttcacaatg    660
ctaaatttgt ttattgcgat tatcgtcaat accatgcaaa ccttcagcga cgaagagcat    720
gcattagagc gtgaacaaga caaacaaatc ttagagcagg aacaaagaca aatgcacgag    780
gagttgaaag ccatcagact cgagctacaa caattacaaa ccttgttgcg caatgctgct    840
ggtgattctt ctaatgtgtc gacaaaggga aacattggtt ctgacttctg ctacgagaac    900
gaggtgtga                                                            909

<210> SEQ ID NO 21
<211> LENGTH: 909
<212> TYPE: DNA
<213> ORGANISM: Artificial sequence
<220> FEATURE:
<223> OTHER INFORMATION: Synthetic

<400> SEQUENCE: 21
atgtcaacct cactgctgaa cgctccaact gggctgcagg caagagtcat caatctggtc     60
gaacagaact ggtttgggca ctttattctg gcactgatcc tgattaacgc agtgcagctg    120
```

```
ggaatggaga ccagcgcctc cctgatggca cagtacggaa cactgctgat gtccctggca      180
aagctgctgc tgagcgtgtt cgtggtcgaa ctgctgctgc gaatctacgc ctatcggggc      240
aagttcttta agacccctg gagcgtgttc gacttcaccg tgatcgtcat tgccctgatt      300
ccagctagtg gacctctggc cgtgctgcgg tcactgagag tgctgagggt cctgcgcgtg      360
ctgacaatcg tgcctagcat gaagagggtg gtctcagctc tgctgggcag cctgccagga      420
ctggcatcca tcgctactgt gctgctgctg atctactatg tcttcgcagt gatcgccact      480
aaaattttcg agacgctttt ccccgagtgg ttcggcacca tcgcagattc tttttataca      540
ctgttccaga tcatgactct ggagtcttgg agtatgggca tcagtcgccc agtcatggaa      600
gtgtacccct atgcctgggt cttctttgtg ccttttattc tggtcgccac cttcacaatg      660
ctgaacctgt ttatcgctat cattgtgaat actatgcaga cctttagcga cgaggaacac      720
gctctggagc gagaacagga taagcagatt ctggagcagg aacagagaca gatgcatgag      780
gaactgaaag caatcaggct ggagctgcag cagctgcaga cactgctgag aaacgctgct      840
ggcgattcat caaacgtgtc cactaaagga acattggct ctgacttctg ctacgagaac      900
gaggtgtga                                                              909

<210> SEQ ID NO 22
<211> LENGTH: 909
<212> TYPE: DNA
<213> ORGANISM: Artificial sequence
<220> FEATURE:
<223> OTHER INFORMATION: Synthetic

<400> SEQUENCE: 22
atgtcaacct cccttctgaa cgcccccacc ggtctgcaag cccgcgtcat caacctggtc       60
gaacagaact ggttcggcca cttcatcctc gcactgattc tcattaacgc cgtgcagctt      120
ggaatggaaa ctagcgcgtc cctgatggct caatacggca cactgctcat gagcctggcg      180
aagctgctcc tgtccgtgtt cgtggtggaa ctgttgctgc ggatctatgc gtaccgcgga      240
aaattcttca aggatccatg gagcgtgttc gactttactg tgattgtgat cgcactcatc      300
ccggcctcgg gaccgctcgc cgtgctccgg tcactgagag tcctgagggt gctcagagtg      360
ctgaccattg tgcctagcat gaagcgcgtg gtgtccgccc tgttgggatc cctgccgggt      420
ttggcttcga ttgccactgt gctgctcctg atctactacg tgttcgccgt cattgccact      480
aagattttcg gcgacgcctt tcctgagtgg ttcggaacca tcgctgactc tttctacacc      540
ttgttccaaa tcatgaccct ggaatcctgg tccatgggga tttcgaggcc cgtgatggag      600
gtgtaccctt acgcctgggt gttcttcgtc cccttcatcc ttgtcgcaac cttcaccatg      660
cttaacctgt ttatcgccat catcgtgaac acgatgcaga ccttctccga tgaagaacat      720
gcgctggagc gggaacagga caagcagatc ctggagcagg aacagcggca gatgcacgag      780
gagctgaagg ccatccggct ggagctgcag cagctccaaa ctctgctgcg caacgcggcc      840
ggagattcaa gcaatgtgtc gaccaagggg aacatcggct ccgacttctg ctacgagaac      900
gaggtgtga                                                              909

<210> SEQ ID NO 23
<211> LENGTH: 294
<212> TYPE: PRT
<213> ORGANISM: Shewanella putrefacien

<400> SEQUENCE: 23
```

```
Ser Thr Ser Leu Leu Asn Ala Pro Thr Gly Leu Gln Ala Arg Val Ile
1               5                   10                  15

Asn Leu Val Glu Gln Asn Trp Phe Gly His Phe Ile Leu Ala Leu Ile
            20                  25                  30

Leu Ile Asn Ala Val Gln Leu Gly Met Glu Thr Ser Ala Ser Leu Met
        35                  40                  45

Ala Gln Tyr Gly Thr Leu Leu Met Ser Leu Ala Lys Leu Leu Leu Ser
50                  55                  60

Val Phe Val Val Glu Leu Leu Arg Ile Tyr Ala Tyr Arg Gly Lys
65                  70                  75                  80

Phe Phe Lys Asp Pro Trp Ser Val Phe Asp Phe Thr Val Ile Val Ile
                85                  90                  95

Ala Leu Ile Pro Ala Ser Gly Pro Leu Ala Val Leu Arg Ser Leu Arg
                100                 105                 110

Val Leu Arg Val Leu Arg Val Leu Thr Ile Val Pro Ser Met Lys Arg
            115                 120                 125

Val Val Ser Ala Leu Leu Gly Ser Leu Pro Gly Leu Ala Ser Ile Ala
        130                 135                 140

Thr Val Leu Leu Leu Ile Tyr Tyr Val Phe Ala Val Ile Ala Thr Lys
145                 150                 155                 160

Ile Phe Gly Asp Ala Phe Pro Glu Trp Phe Gly Thr Ile Ala Asp Ser
                165                 170                 175

Phe Tyr Thr Leu Phe Gln Ile Met Thr Leu Glu Ser Trp Ser Met Gly
            180                 185                 190

Ile Ser Arg Pro Val Met Glu Val Tyr Pro Tyr Ala Trp Val Phe Phe
        195                 200                 205

Val Pro Phe Ile Leu Val Ala Thr Phe Thr Met Leu Asn Leu Phe Ile
210                 215                 220

Ala Ile Ile Val Asn Thr Met Gln Thr Phe Ser Asp Glu Glu His Ala
225                 230                 235                 240

Leu Glu Arg Glu Gln Asp Lys Gln Ile Leu Gln Glu Gln Arg Gln
                245                 250                 255

Met His Glu Glu Leu Lys Ala Ile Arg Leu Glu Leu Gln Gln Leu Gln
            260                 265                 270

Thr Leu Leu Arg Asn Ala Ala Gly Asp Ser Ser Asn Val Ser Thr Lys
        275                 280                 285

Gly Asn Ile Gly Ser Asp
    290

<210> SEQ ID NO 24
<211> LENGTH: 301
<212> TYPE: PRT
<213> ORGANISM: Shewanella putrefacien

<400> SEQUENCE: 24

Ser Thr Ser Leu Leu Asn Ala Pro Thr Gly Leu Gln Ala Arg Val Ile
1               5                   10                  15

Asn Leu Val Glu Gln Asn Trp Phe Gly His Phe Ile Leu Ala Leu Ile
            20                  25                  30

Leu Ile Asn Ala Val Gln Leu Gly Met Glu Thr Ser Ala Ser Leu Met
        35                  40                  45

Ala Gln Tyr Gly Thr Leu Leu Met Ser Leu Ala Lys Leu Leu Leu Ser
50                  55                  60

Val Phe Val Val Glu Leu Leu Arg Ile Tyr Ala Tyr Arg Gly Lys
65                  70                  75                  80
```

Phe Phe Lys Asp Pro Trp Ser Val Phe Asp Phe Thr Val Ile Val Ile
            85                  90                  95

Ala Leu Ile Pro Ala Ser Gly Pro Leu Ala Val Leu Arg Ser Leu Arg
        100                 105                 110

Val Leu Arg Val Leu Arg Val Leu Thr Ile Val Pro Ser Met Lys Arg
    115                 120                 125

Val Val Ser Ala Leu Leu Gly Ser Leu Pro Gly Leu Ala Ser Ile Ala
130                 135                 140

Thr Val Leu Leu Leu Ile Tyr Tyr Val Phe Ala Val Ile Ala Thr Lys
145                 150                 155                 160

Ile Phe Gly Asp Ala Phe Pro Glu Trp Phe Gly Thr Ile Ala Asp Ser
                165                 170                 175

Phe Tyr Thr Leu Phe Gln Ile Met Thr Leu Glu Ser Trp Ser Met Gly
            180                 185                 190

Ile Ser Arg Pro Val Met Glu Val Tyr Pro Tyr Ala Trp Val Phe Phe
        195                 200                 205

Val Pro Phe Ile Leu Val Ala Thr Phe Thr Met Leu Asn Leu Phe Ile
    210                 215                 220

Ala Ile Ile Val Asn Thr Met Gln Thr Phe Ser Asp Glu Glu His Ala
225                 230                 235                 240

Leu Glu Arg Glu Gln Asp Lys Gln Ile Leu Glu Gln Glu Gln Arg Gln
                245                 250                 255

Met His Glu Glu Leu Lys Ala Ile Arg Leu Glu Leu Gln Gln Leu Gln
            260                 265                 270

Thr Leu Leu Arg Asn Ala Ala Gly Asp Ser Ser Asn Val Ser Thr Lys
        275                 280                 285

Gly Asn Ile Gly Ser Asp Phe Cys Tyr Glu Asn Glu Val
    290                 295                 300

<210> SEQ ID NO 25
<211> LENGTH: 7784
<212> TYPE: DNA
<213> ORGANISM: Artificial sequence
<220> FEATURE:
<223> OTHER INFORMATION: Synthetic

<400> SEQUENCE: 25
agcttaatgt agtcttatgc aatactcttg tagtcttgca acatggtaac gatgagttag      60
caacatgcct tacaaggaga gaaaaagcac cgtgcatgcc gattggtgga agtaaggtgg     120
tacgatcgtg ccttattagg aaggcaacag acgggtctga catggattgg acgaaccact     180
gaattgccgc attgcagaga tattgtattt aagtgcctag ctcgatacaa taaacgggtc     240
tctctggtta gaccagatct gagcctggga gctctctggc taactaggga acccactgct     300
taagcctcaa taaagcttgc cttgagtgct tcaagtagtg tgtgcccgtc tgttgtgtga     360
ctctggtaac tagagatccc tcagaccctt ttagtcagtg tggaaaatct ctagcagtgg     420
cgcccgaaca gggacctgaa agcgaagggg aaaccagagc tctctcgacg caggactcgg     480
cttgctgaag cgcgcacggc aagaggcgag gggcggcgac tggtgagtac gccaaaaatt     540
ttgactagcg gaggctagaa ggagagagat gggtgcgaga gcgtcagtat taagcggggg     600
agaattagat cgcgatggga aaaaattcgg ttaaggccag ggggaagaa aaaatataaa     660 ttaaaacata tagtatgggc aagcaggag ctagaacgat tcgcagttaa tcctggcctg     720
ttagaaacat cagaaggctg tagacaaata ctgggacagc tacaaccatc ccttcagaca     780

```
ggatcagaag aacttagatc attatataat acagtagcaa ccctctattg tgtgcatcaa    840
aggatagaga taaaagacac caaggaagct ttagacaaga tagaggaaga gcaaaacaaa    900
agtaagacca ccgcacagca agcggccgct gatcttcaga cctggaggag gagatatgag    960
ggacaattgg agaagtgaat tatataaata taaagtagta aaaattgaac cattaggagt   1020
agcacccacc aaggcaaaga gaagagtggt gcagagagaa aaaagagcag tgggaatagg   1080
agctttgttc cttgggttct tgggagcagc aggaagcact atgggcgcag cctcaatgac   1140
gctgacggta caggccagac aattattgtc tggtatagtg cagcagcaga acaatttgct   1200
gagggctatt gaggcgcaac agcatctgtt gcaactcaca gtctgggggca tcaagcagct   1260 ccaggcaaga atcctggctg tggaaagata cctaaaggat caacagctcc tggggatttg   1320
gggttgctct ggaaaactca tttgcaccac tgctgtgcct tggaatgcta gttggagtaa   1380
taaatctctg gaacagattt ggaatcacac gacctggatg gagtgggaca gagaaattaa   1440
caattcacac agcttaatac actccttaat tgaagaatcg caaaaccagc aagaaaagaa   1500
tgaacaagaa ttattggaat tagataaatg ggcaagtttg tggaattggt ttaacataac   1560
aaattggctg tggtatataa aattattcat aatgatagta ggaggcttgg taggtttaag   1620
aatagttttt gctgtacttt ctatagtgaa tagagttagg cagggatatt caccattatc   1680
gtttcagacc cacctcccaa ccccgagggg acccgacagg cccgaaggaa tagaagaaga   1740
aggtggagag agagacagag acagatccat tcgattagtg aacggatctc gacggtatcg   1800 gttaacttttt aaaagaaaag gggggattgg ggggtacagt gcaggggaaa gaatagtaga   1860
cataatagca acagacatac aaactaaaga attacaaaaa caaattacaa aaattcaaaa   1920
ttttatcgat aagcttggga gttccgcgtt acataactta cggtaaatgg cccgcctggc   1980
tgaccgccca acgaccccccg cccattgacg tcaataatga cgtatgttcc catagtaacg   2040 ccaatagggga ctttccattg acgtcaatgg gtggagtatt tacggtaaac tgcccacttg   2100
gcagtacatc aagtgtatca tatgccaagt acgccccctta ttgacgtcaa tgacggtaaa   2160
tggcccgcct ggcattatgc ccagtacatg accttatggg actttcctac ttggcagtac   2220
atctacgtat tagtcatcgc tattaccatg gtgatgcggt tttggcagta catcaatggg   2280
cgtggatagc ggtttgactc acggggattt ccaagtctcc accccattga cgtcaatggg   2340
agtttgtttt ggcaccaaaa tcaacgggac tttccaaaat gtcgtaacaa ctccgcccca   2400
ttgacgcaaa tgggcggtag gcgtgtacgg tgggaggtct atataagcag agctcgttta   2460
gtgaaccgtc agatcgcctg gagacgccat ccacgctgtt ttgacctcca tagaagacac   2520
cgactctagt aatacgactc actataggct agcgccacca tgagtacatc tttacttaac   2580
gcgccaacgg gtttgcaggc acgagtgatt aacttggttg agcaaaactg gtttggtcat   2640
tttattttgg cattgatttt aatcaacgcg gtgcagttag gtatggagac ctcagccagc   2700
ctgatggcgc aatacggtac tttgttgatg agtcttgata agttgctact gagtgtattt   2760
gtggtggagt tattgctgcg gatttatgcc tacaggggga aatttttttaa agacccttgg   2820 agcgtgttcg attttaccgt gatagtgata gcactgatcc ctgcatctgg gccattggct   2880
gtcctgcgtt cgctcagggt attgcgggtg ctgagagtgt taacaattgt gccatcaatg   2940
aaacgggtgg tgtctgcgct gttgggatca cttcctggat tggcatcgat cgccacggta   3000
ttactgttga tttattatgt gtttgcggtg attgctacca aaattttttgg cgatgcattc   3060 cctgaatggt ttgcactat tgctgactca ttttataccc tatttcaaat aatgacgctt   3120
gaaagctggt ctatgggaat ttcgcggcca gtgatggaag tgtacccctta tgcttgggta   3180
```

```
tttttcgtac catttattct ggtagcgact ttcacaatgc taaatttgtt tattgcgatt    3240
atcgtcaata ccatgcaaac cttcagcgac gaagagcatg cattagagcg tgaacaagac    3300
aaacaaatct tagagcagga acaaagacaa atgcacgagg agttgaaagc catcagactc    3360
gagctacaac aattacaaac cttgttgcgc aatgctgctg gtgattcttc taatgtgtcg    3420
acaaagggaa acattggttc tgacgaattc gagggcagag gaagtcttct aacatgcggt    3480
gacgtggagg agaatcccgg ccctaccaca accatggtga gcaagggcga ggagctgttc    3540
accggggtgg tgcccatcct ggtcgagctg gacggcgacg taaacggcca agttcagc     3600
gtgtccggcg agggcgaggg cgatgccacc tacggcaagc tgaccctgaa gttcatctgc    3660
accaccggca agctgcccgt gccctggccc accctcgtga ccaccctgac ctacggcgtg    3720
cagtgcttca gccgctaccc cgaccacatg aagcagcacg acttcttcaa gtccgccatg    3780
cccgaaggct acgtccagga gcgcaccatc ttcttcaagg acgacggcaa ctacaagacc    3840
cgcgccgagg tgaagttcga gggcgacacc ctggtgaacc gcatcgagct gaagggcatc    3900
gacttcaagg aggacggcaa catcctgggg cacaagctgg agtacaacta caacagccac    3960
aacgtctata tcatggccga caagcagaag aacggcatca aggtgaactt caagatccgc    4020
cacaacatcg aggacggcag cgtgcagctc gccgaccact accagcagaa cacccccatc    4080
ggcgacggcc ccgtgctgct gcccgacaac cactacctga gcacccagtc cgccctgagc    4140
aaagacccca acgagaagcg cgatcacatg gtcctgctgg agttcgtgac cgccgccggg    4200
atcactctcg gcatggacga gctgtacaag tagtctagac ttaagccttt aagaccaatg    4260
acttacaagg cagctgtaga tcttagccac ttttttaaaag aaaagggggg actggaaggg    4320
ctaattcact cccaacgaag acaagatctg cttttttgctt gtactgggtc tctctggtta    4380
gaccagatct gagcctggga gctctctggc taactaggga acccactgct taagcctcaa    4440
taaagcttgc cttgagtgct tcaagtagtg tgtgcccgtc tgttgtgtga ctctggtaac    4500
tagagatccc tcagaccctt ttagtcagtg tggaaaatct ctagcagtag tagttcatgt    4560
catcttatta ttcagtattt ataacttgca aagaaatgaa tatcagagag tgagaggaac    4620
ttgtttattg cagcttataa tggttacaaa taaagcaata gcatcacaaa tttcacaaat    4680
aaagcatttt tttcactgca ttctagttgt ggtttgtcca aactcatcaa tgtatcttat    4740
catgtctggc tctagctatc ccgcccctaa ctccgcccag ttccgcccat tctccgcccc    4800
atggctgact aattttttt atttatgcag aggccgaggc cgcctcggcc tctgagctat    4860
tccagaagta gtgaggaggc ttttttggag gcctaggctt ttgcgtcgag acgtacccaa    4920
ttcgccctat agtgagtcgt attacgcgcg ctcactggcc gtcgttttac aacgtcgtga    4980
ctgggaaaac cctggcgtta cccaacttaa tcgccttgca gcacatcccc ctttcgccag    5040
ctggcgtaat agcgaagagg cccgcaccga tcgcccttcc caacagttgc gcagcctgaa    5100
tggcgaatgg cgcgacgcgc cctgtagcgg cgcattaagc gcggcgggtg tggtggttac    5160
gcgcagcgtg accgctacac ttgccagcgc cctagcgccc gctcctttcg ctttcttccc    5220
ttcctttctc gccacgttcg ccggctttcc ccgtcaagct ctaaatcggg gctccctt    5280
agggttccga tttagtgctt tacggcacct cgaccccaaa aaacttgatt agggtgatgg    5340
ttcacgtagt gggccatcgc cctgatagac ggtttttcgc cctttgacgt tggagtccac    5400
gttctttaat agtggactct tgttccaaac tggaacaaca ctcaacccta tctcggtcta    5460
ttcttttgat ttataaggga ttttgccgat ttcggcctat tggttaaaaa atgagctgat    5520
```

-continued

```
ttaacaaaaa tttaacgcga attttaacaa aatattaacg tttacaatt  cccaggtggc    5580 acttttcggg gaaatgtgcg cggaacccct atttgtttat ttttctaaat acattcaaat    5640
atgtatccgc tcatgagaca ataaccctga taaatgcttc aataatattg aaaaaggaag    5700
agtatgagta ttcaacattt ccgtgtcgcc cttattccct tttttgcggc attttgcctt    5760 cctgttttg  ctcacccaga aacgctggtg aaagtaaaag atgctgaaga tcagttgggt    5820
gcacgagtgg gttacatcga actggatctc aacagcggta agatccttga gagttttcgc    5880
cccgaagaac gttttccaat gatgagcact tttaaagttc tgctatgtgg cgcggtatta    5940
tcccgtattg acgccgggca agagcaactc ggtcgccgca tacactattc tcagaatgac    6000
ttggttgagt actcaccagt cacagaaaag catcttacgg atggcatgac agtaagagaa    6060
ttatgcagtg ctgccataac catgagtgat aacactgcgg ccaacttact tctgacaacg    6120
atcggaggac cgaaggagct aaccgctttt ttgcacaaca tgggggatca tgtaactcgc    6180
cttgatcgtt gggaaccgga gctgaatgaa gccataccaa acgacgagcg tgacaccacg    6240
atgcctgtag caatggcaac aacgttgcgc aaactattaa ctggcgaact acttactcta    6300
gcttcccggc aacaattaat agactggatg gaggcggata agttgcagg  accacttctg    6360 cgctcggccc ttccggctgg ctggtttatt gctgataaat ctggagccgg tgagcgtggg    6420
tctcgcggta tcattgcagc actggggcca gatggtaagc cctcccgtat cgtagttatc    6480
tacacgacgg gagtcaggc  aactatggat gaacgaaata gacagatcgc tgagataggt    6540
gcctcactga ttaagcattg gtaactgtca gaccaagttt actcatatat actttagatt    6600
gatttaaaac ttcattttta atttaaaagg atctaggtga agatcctttt tgataatctc    6660
atgaccaaaa tcccttaacg tgagttttcg ttccactgag cgtcagaccc cgtagaaaag    6720
atcaaaggat cttcttgaga tcctttttt  ctgcgcgtaa tctgctgctt gcaaacaaaa    6780
aaaccaccgc taccagcggt ggtttgtttg ccggatcaag agctaccaac tcttttccg    6840 aaggtaactg gcttcagcag agcgcagata ccaaatactg tccttctagt gtagccgtag    6900
ttaggccacc acttcaagaa ctctgtagca ccgcctacat acctcgctct gctaatcctg    6960
ttaccagtgg ctgctgccag tggcgataag tcgtgtctta ccgggttgga ctcaagacga    7020
tagttaccgg ataaggcgca gcggtcgggc tgaacggggg gttcgtgcac acagcccagc    7080
ttggagcgaa cgacctacac cgaactgaga tacctacagc gtgagctatg agaaagcgcc    7140
acgcttcccg aagggagaaa ggcggacagg tatccggtaa gcggcagggt cggaacagga    7200
gagcgcacga gggagcttcc agggggaaac gcctggtatc tttatagtcc tgtcgggttt    7260
cgccacctct gacttgagcg tcgatttttg tgatgctcgt caggggggcg gagcctatgg    7320
aaaaacgcca gcaacgcggc ctttttacgg ttcctggcct tttgctggcc ttttgctcac    7380
atgttctttc ctgcgttatc ccctgattct gtggataacc gtattaccgc ctttgagtga    7440
gctgataccg ctcgccgcag ccgaacgacc gagcgcagcg agtcagtgag cgaggaagcg    7500
gaagagcgcc caatacgcaa accgcctctc cccgcgcgtt ggccgattca ttaatgcagc    7560
tggcacgaca ggtttcccga ctggaaagcg ggcagtgagc gcaacgcaat taatgtgagt    7620
tagctcactc attaggcacc ccaggcttta cactttatgc ttccggctcg tatgttgtgt    7680
ggaattgtga gcggataaca atttcacaca ggaaacagct atgaccatga ttacgccaag    7740
cgcgcaatta accctcacta aagggaacaa aagctggagc tgca                    7784
```

<210> SEQ ID NO 26
<211> LENGTH: 382

<212> TYPE: PRT
<213> ORGANISM: Homo sapien

<400> SEQUENCE: 26

```
Met Gly Asp Trp Ser Ala Leu Gly Lys Leu Leu Asp Lys Val Gln Ala
1               5                   10                  15

Tyr Ser Thr Ala Gly Gly Lys Val Trp Leu Ser Val Leu Phe Ile Phe
            20                  25                  30

Arg Ile Leu Leu Leu Gly Thr Ala Val Glu Ser Ala Trp Gly Asp Glu
        35                  40                  45

Gln Ser Ala Phe Arg Cys Asn Thr Gln Gln Pro Gly Cys Glu Asn Val
    50                  55                  60

Cys Tyr Asp Lys Ser Phe Pro Ile Ser His Val Arg Phe Trp Val Leu
65                  70                  75                  80

Gln Ile Ile Phe Val Ser Val Pro Thr Leu Leu Tyr Leu Ala His Val
                85                  90                  95

Phe Tyr Val Met Arg Lys Glu Glu Lys Leu Asn Lys Lys Glu Glu Glu
            100                 105                 110

Leu Lys Val Ala Gln Thr Asp Gly Val Asn Val Asp Met His Leu Lys
        115                 120                 125

Gln Ile Glu Ile Lys Lys Phe Lys Tyr Gly Ile Glu Glu His Gly Lys
    130                 135                 140

Val Lys Met Arg Gly Gly Leu Leu Arg Thr Tyr Ile Ile Ser Ile Leu
145                 150                 155                 160

Phe Lys Ser Ile Phe Glu Val Ala Phe Leu Leu Ile Gln Trp Tyr Ile
                165                 170                 175

Tyr Gly Phe Ser Leu Ser Ala Val Tyr Thr Cys Lys Arg Asp Pro Cys
            180                 185                 190

Pro His Gln Val Asp Cys Phe Leu Ser Arg Pro Thr Glu Lys Thr Ile
        195                 200                 205

Phe Ile Ile Phe Met Leu Val Val Ser Leu Val Ser Leu Ala Leu Asn
    210                 215                 220

Ile Ile Glu Leu Phe Tyr Val Phe Phe Lys Gly Val Lys Asp Arg Val
225                 230                 235                 240

Lys Gly Lys Ser Asp Pro Tyr His Ala Thr Ser Gly Ala Leu Ser Pro
                245                 250                 255

Ala Lys Asp Cys Gly Ser Gln Lys Tyr Ala Tyr Phe Asn Gly Cys Ser
            260                 265                 270

Ser Pro Thr Ala Pro Leu Ser Pro Met Ser Pro Pro Gly Tyr Lys Leu
        275                 280                 285

Val Thr Gly Asp Arg Asn Asn Ser Ser Cys Arg Asn Tyr Asn Lys Gln
    290                 295                 300

Ala Ser Glu Gln Asn Trp Ala Asn Tyr Ser Ala Glu Gln Asn Arg Met
305                 310                 315                 320

Gly Gln Ala Gly Ser Thr Ile Ser Asn Ser His Ala Gln Pro Phe Asp
                325                 330                 335

Phe Pro Asp Asp Asn Gln Asn Ser Lys Lys Leu Ala Ala Gly His Glu
            340                 345                 350

Leu Gln Pro Leu Ala Ile Val Asp Gln Arg Pro Ser Ser Arg Ala Ser
        355                 360                 365

Ser Arg Ala Ser Ser Arg Pro Arg Pro Asp Asp Leu Glu Ile
    370                 375                 380
```

<210> SEQ ID NO 27

<211> LENGTH: 427
<212> TYPE: PRT
<213> ORGANISM: Homo sapien

<400> SEQUENCE: 27

```
Met Gly Ser Val Arg Thr Asn Arg Tyr Ser Ile Val Ser Ser Glu Glu
1               5                   10                  15

Asp Gly Met Lys Leu Ala Thr Met Ala Val Ala Asn Gly Phe Gly Asn
            20                  25                  30

Gly Lys Ser Lys Val His Thr Arg Gln Gln Cys Arg Ser Arg Phe Val
        35                  40                  45

Lys Lys Asp Gly His Cys Asn Val Gln Phe Ile Asn Val Gly Glu Lys
    50                  55                  60

Gly Gln Arg Tyr Leu Ala Asp Ile Phe Thr Thr Cys Val Asp Ile Arg
65                  70                  75                  80

Trp Arg Trp Met Leu Val Ile Phe Cys Leu Ala Phe Val Leu Ser Trp
                85                  90                  95

Leu Phe Phe Gly Cys Val Phe Trp Leu Ile Ala Leu Leu His Gly Asp
            100                 105                 110

Leu Asp Ala Ser Lys Glu Gly Lys Ala Cys Val Ser Glu Val Asn Ser
        115                 120                 125

Phe Thr Ala Ala Phe Leu Phe Ser Ile Glu Thr Gln Thr Thr Ile Gly
    130                 135                 140

Tyr Gly Phe Arg Cys Val Thr Asp Glu Cys Pro Ile Ala Val Phe Met
145                 150                 155                 160

Val Val Phe Gln Ser Ile Val Gly Cys Ile Ile Asp Ala Phe Ile Ile
                165                 170                 175

Gly Ala Val Met Ala Lys Met Ala Lys Pro Lys Lys Arg Asn Glu Thr
            180                 185                 190

Leu Val Phe Ser His Asn Ala Val Ile Ala Met Arg Asp Gly Lys Leu
        195                 200                 205

Cys Leu Met Trp Arg Val Gly Asn Leu Arg Lys Ser His Leu Val Glu
210                 215                 220

Ala His Val Arg Ala Gln Leu Leu Lys Ser Arg Ile Thr Ser Glu Gly
225                 230                 235                 240

Glu Tyr Ile Pro Leu Asp Gln Ile Asp Ile Asn Val Gly Phe Asp Ser
                245                 250                 255

Gly Ile Asp Arg Ile Phe Leu Val Ser Pro Ile Thr Ile Val His Glu
            260                 265                 270

Ile Asp Glu Asp Ser Pro Leu Tyr Asp Leu Ser Lys Gln Asp Ile Asp
        275                 280                 285

Asn Ala Asp Phe Glu Ile Val Val Ile Leu Glu Gly Met Val Glu Ala
    290                 295                 300

Thr Ala Met Thr Thr Gln Cys Arg Ser Ser Tyr Leu Ala Asn Glu Ile
305                 310                 315                 320

Leu Trp Gly His Arg Tyr Glu Pro Val Leu Phe Glu Glu Lys His Tyr
                325                 330                 335

Tyr Lys Val Asp Tyr Ser Arg Phe His Lys Thr Tyr Glu Val Pro Asn
            340                 345                 350

Thr Pro Leu Cys Ser Ala Arg Asp Leu Ala Glu Lys Lys Tyr Ile Leu
        355                 360                 365

Ser Asn Ala Asn Ser Phe Cys Tyr Glu Asn Glu Val Ala Leu Thr Ser
    370                 375                 380

Lys Glu Glu Asp Asp Ser Glu Asn Gly Val Pro Glu Ser Thr Ser Thr
```

-continued

```
            385                 390                 395                 400

Asp Thr Pro Pro Asp Ile Asp Leu His Asn Gln Ala Ser Val Pro Leu
                405                 410                 415

Glu Pro Arg Pro Leu Arg Arg Glu Ser Glu Ile
                420                 425
```

USE OF BACTERIAL VOLTAGE GATED ION CHANNELS FOR HUMAN THERAPIES

CROSS-REFERENCE TO RELATED APPLICATIONS

This application claims priority to U.S. Provisional Patent Application No. 62/537,289, filed Jul. 26, 2017, and U.S. Provisional Patent Application No. 62/557,957, filed Sep. 13, 2017, each of which is incorporated herein by reference in its entirety.

STATEMENT REGARDING FEDERALLY SPONSORED RESEARCH

This invention was made with government support under grant HL104326, HL132389, HL126524, and HL126193 awarded by the National Institutes of Health. The government has certain rights in the invention.

FIELD

This disclosure relates to compositions including prokaryotic ion channel polypeptides and methods of treating voltage gated ion channel-related conditions such as heart arrhythmia, chronic atrial fibrillation, damage from myocardial infarction, damage from stroke, and chronic ischemia.

SEQUENCE LISTING

The instant application includes a Sequence Listing which has been submitted electronically in ASCII format and is hereby incorporated by reference in its entirety. Said ASCII copy, created on Oct. 9, 2018, is named 028193-9257-US02_As_Filed_Sequence_Listing.txt and is 33,921 bytes in size.

INTRODUCTION

Voltage-gated sodium channels (VGSCs) enable firing and spread of action potentials (APs) in electrically excitable tissues, and their loss-of-function mutations cause a variety of neuronal, cardiac, and skeletal muscle disorders. Similarly, acute tissue injuries such as myocardial infarction may result in permanent excitability loss and are associated with long-term disability and death. Treatment of such disorders is often hindered by the inability to stably overexpress large mammalian VGSCs via viral delivery methods. There is a need for new methods of treatment for voltage gated ion channel-related conditions.

SUMMARY

In an aspect, the disclosure relates to methods of treating a voltage gated ion channel-related condition in a subject. The method may include administering to the subject a recombinant AAV9 vector encoding a BacNav prokaryotic ion channel polypeptide, wherein the BacNav prokaryotic ion channel polypeptide is expressed in the cardiomyocytes of the subject, and wherein the voltage gated ion channel-related condition is selected from heart arrhythmia, chronic atrial fibrillation, damage from myocardial infarction, damage from stroke, and chronic ischemia.

In a further aspect, the disclosure relates to methods of increasing the conductivity of a cardiac tissue of a subject. The method may include administering to the subject a recombinant AAV9 vector encoding a BacNav prokaryotic ion channel polypeptide, wherein the BacNav prokaryotic ion channel polypeptide is expressed in the cardiomyocytes of the subject.

Another aspect of the disclosure provides methods of increasing the resistance to conduction block of a cardiac tissue of a subject. The method may include administering to the subject a recombinant AAV9 vector encoding a BacNav prokaryotic ion channel polypeptide, wherein the BacNav prokaryotic ion channel polypeptide is expressed in the cardiomyocytes of the subject.

Another aspect of the disclosure provides methods of increasing the upstroke velocity of a cardiac tissue of a subject. The method may include administering to the subject a recombinant AAV9 vector encoding a BacNav prokaryotic ion channel polypeptide, wherein the BacNav prokaryotic ion channel polypeptide is expressed in the cardiomyocytes of the subject.

In some embodiments, the BacNav prokaryotic ion channel polypeptide comprises an amino acid sequence selected from SEQ ID NO. 23 or a variant thereof, or SEQ ID NO: 24 or a variant thereof. In some embodiments, the BacNav prokaryotic ion channel polypeptide comprises an amino acid sequence encoded by a polynucleotide sequence selected from SEQ ID NO: 1, SEQ ID NO: 2, and SEQ ID NO: 3. In some embodiments, the BacNav prokaryotic ion channel polypeptide comprises a motif having an amino acid sequence of SEQ ID NO: 4 (GVKESL), SEQ ID NO: 5 (DLRRSL), or SEQ ID NO: 6 (FCYENEV), or a combination thereof. In some embodiments, the motif is positioned at the C-terminal end of the BacNav prokaryotic ion channel polypeptide. In some embodiments, the vector comprises a polynucleotide sequence of SEQ ID NO: 25. In some embodiments, the vector is administered to the subject in a pharmaceutical composition comprising the vector and a pharmaceutically acceptable carrier. In some embodiments, the vector is administered to a coronary artery or a coronary sinus of the subject. In some embodiments, the vector is administered to the subject sublingually, orally, intranasally, intravenously, parenterally, subcutaneously, intramuscularly, intraperitoneally, rectally, intravaginally, or intrathecally. In some embodiments, the BacNav prokaryotic ion channel polypeptide is a sodium channel, a calcium channel, or a combination thereof. In some embodiments, the BacNav prokaryotic ion channel polypeptide is a sodium channel. In some embodiments, the prokaryotic ion channel polypeptide has reduced immunogenicity relative to a control. In some embodiments, the prokaryotic ion channel polypeptide has reduced antigenicity relative to a control. In some embodiments, the prokaryotic ion channel polypeptide is immunosuppressive. In some embodiments, the cardiomyocyte expressing the prokaryotic ion channel polypeptide has reduced immunogenicity relative to a control. In some embodiments, the cardiomyocyte expressing the prokaryotic ion channel polypeptide has reduced antigenicity relative to a control. In some embodiments, the cardiomyocyte expressing the prokaryotic ion channel polypeptide is immunosuppressive.

The disclosure provides for other aspects and embodiments that will be apparent in light of the following detailed description and accompanying figures.

BRIEF DESCRIPTION OF THE DRAWINGS

FIG. 1A-FIG. 1F. Improving NavSheP D60A gene expression via codon optimization. (FIG. 1A-FIG. 1B) When linked with EGFP gene via T2A peptide in a bi-cistronic lentiviral vector, codon optimized NavSheP D60A sequences using Genscript (hShePA) and ATUM (h2ShePA) algorithms resulted in higher GFP intensity in transduced HEK293s compared to a non-optimized version (bShePA), as examined under fluorescence microscope (FIG. 1A) or flow cytometry (FIG. 1B). Scale bars, 100 µm. (FIG. 1C) Peak INa measured in HEK293 cells transduced with h2ShePA and hShePA were significantly greater than bShePA-expressing cells. (FIG. 1D-FIG. 1F) When transduced in Kir2.1 HEK293 cells, codon optimized channels showed notably higher AP upstroke (FIG. 1D), slightly longer (but not statistically significant) APD (FIG. 1E), and similar resting membrane potential (FIG. 1F). *$P<0.001$ vs bShePA in (FIG. 1D).

FIG. 2A-FIG. 2H. Improving membrane trafficking of NavSheP D60A. (FIG. 2A-FIG. 2B) Addition of mEGFP to the C-terminus of h2ShePA channel resulted in only perinuclear labeling (FIG. 2A) while mEGFP fusion to the N-terminus of h2ShePA showed GFP labeling throughout the cell, including big intracellular aggregates (FIG. 2B). (FIG. 2C-FIG. 2D) Addition of ER export motifs from Kv1.4 (FIG. 2C) or Kv1.5 (FIG. 2D) did not improve trafficking of h2ShePA channels. (FIG. 2E-FIG. 2F) ER export motif significantly improved membrane labeling of h2ShePA channel when added to the C-terminus of the fusion protein (FIG. 2E), but not its N-terminus (FIG. 2F). (FIG. 2G-FIG. 2H) Improved membrane trafficking via the addition of ER3 increased INa peak current (FIG. 2G) and upstroke velocity (FIG. 2H) in transfected Kir2.1+Cx43 HEK293 cells. *$P<0.001$. Scale bars, 20 µm in (FIG. 2A)-(FIG. 2F).

FIG. 3A-FIG. 3K. Improving membrane trafficking in other BacNav orthologs. (FIG. 3A-FIG. 3E) Large intracellular aggregates were observed in cells expressing NavBacL (FIG. 3A) and NaChBac (FIG. 3B) while NavMs expression resulted in primarily perinuclear labeling (FIG. 3C). Expressions of NavPz (FIG. 3D) and NavSilP (FIG. 3E) yielded no aggregation but membrane labeling remained poor. (FIG. 3F-FIG. 3J) Membrane trafficking of all tested channels were enhanced in the presence of ER3 motif. (FIG. 3K) Improved NavPZ membrane trafficking via the addition of ER3 increased INa peak current in transfected Kir2.1+Cx43 HEK293 cells. Scale bars, 10 µm.

FIG. 4A-FIG. 4H. BacNav expression augmented cardiac conduction under normal condition. (FIG. 4A) Schematic depicting exogenous expression of BacNav in cardiomyocytes (CMs) to augment conduction. (FIG. 4B and FIG. 4C) Representative isochrone maps of AP conduction in electrically stimulated isotropic monolayers of control neonatal rat CMs (FIG. 4B) and CMs transduced with NavSheP D60A lentivirus (FIG. 4C). Pulse signs indicate location of stimulating electrode. Circles denote 504 recording sites. (FIG. 4D and FIG. 4E) CM monolayers transduced with NavSheP D60A lentivirus (CM+D60A) show increased CV (FIG. 4D) and unaltered APD80 (FIG. 4E) compared to control CM monolayers (n=5). *$P<0.001$ vs control CM. (FIG. 4F) Simulated CV of NRVM model gradually increased with higher NavSheP D60A conductance ($\overline{G}$Na). (FIG. 4G and FIG. 4H) Simulated CV (FIG. 4G) and APD80 (FIG. 4H) of CM model when $\overline{G}$Na=0 (blue bar) and when $\overline{G}$Na=281 nS (yellow bar).

FIG. 5A-FIG. 5I. BacNav expression improved conduction and prevented reentrant activity in fibrotic cardiac cultures. (FIG. 5A and FIG. 5B) Immunostaining images of F-actin+ NRVM cultures with high content of vimentin+ fibroblasts exhibiting robust GFP expression in the NavSheP D60A-GFP transduced group (FIG. 5B) but not in the non-transduced control (FIG. 5A). Scale bas, 100 µm. (FIG. 5C and FIG. 5D) Representative isochrone maps of AP propagation in electrically stimulated fibrotic cardiac cultures in the absence (FIG. 5D) and presence (FIG. 5E) of NavSheP D60A expression. Pulse signs indicate location of stimulating electrode. Circles denote 504 recording sites. (FIG. 5E-FIG. 5G) Fibrotic cardiac monolayers transduced with NavSheP D60A lentivirus exhibit improved CV (FIG. 5E), higher maximum capture rate (FIG. 5F), and unaltered APD80 (FIG. 5G) compared to untransduced control monolayers (n=12-18). *$P<0.001$ vs. untransduced control. (FIG. 5H) Representative isochrone maps showing reentry in untransduced fibrotic control. (FIG. 5I) Untransduced control (fibrotic) exhibited reentry in 10/22 monolayers while transduction with BacNav lentivirus (D60A) prevented development of reentrant activity in all 12 tested monolayers.

DETAILED DESCRIPTION

Figure 1D:
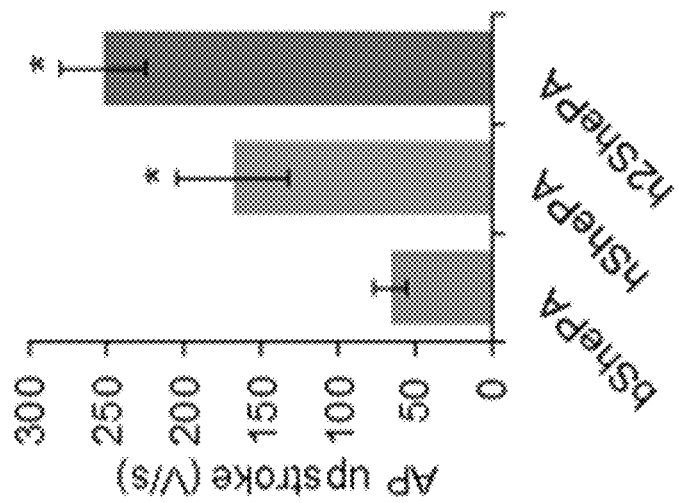

Described herein are prokaryotic ion channel polypeptides and their use in methods of treating a voltage gated ion channel-related condition in a subject.

The recent discovery of a prokaryotic voltage-gated sodium channel superfamily (BacNav) has provided novel insights into the crystal structure, gating mechanisms, and pharmacology of mammalian VGSCs3. The small gene size of BacNav may be exploited to generate and directly enhance mammalian tissue excitability. As detailed herein, coexpression of engineered BacNav, Kir2.1, and Cx43 in primary human fibroblasts yielded actively conducting cells with customizable electrophysiological phenotypes that successfully rescued conduction slowing in an in vitro model of cardiac interstitial fibrosis. Furthermore, direct expression of engineered BacNav channels in mammalian excitable tissues, such as, for example, cardiomyocytes, enhanced endogenous excitability and prevented arrhythmogenic conduction slowing under various pathological conditions associated with depressed excitability, decreased intercellular coupling, and fibrosis.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and," and "the" include plural references unless the context clearly dictates otherwise. The present disclosure also contemplates other embodiments "comprising," "consisting of," and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "about" as used herein as applied to one or more values of interest, refers to a value that is similar to a stated reference value. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The term "administration" or "administering," as used herein, refers to providing, contacting, and/or delivery of an agent by any appropriate route to achieve the desired effect. These agents may be administered to a subject in numerous ways including, but not limited to, sublingually, orally, ocularly, nasally, intravenously, topically, as aerosols, suppository, etc. and may be used in combination.

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids may include, for example, Gly, Ala, Val, Ile, Leu, Met, Phe, Tyr, Trp, Cys, Pro, Arg, His, Lys, Asp, Glu, Ser, Thr, Asn, and Gln. Amino acids include the side chain and polypeptide backbone portions.

"Antigen" refers to a molecule capable of being bound by an antibody or a T cell receptor. The term "antigen", as used herein, also encompasses T-cell epitopes. An antigen is additionally capable of being recognized by the immune system and/or being capable of inducing a humoral immune response and/or cellular immune response leading to the activation of B-lymphocytes and/or T-lymphocytes. In some embodiments, the antigen contains or is linked to a Th cell epitope. An antigen can have one or more epitopes (B-epitopes and T-epitopes). Antigens may include polypeptides, polynucleotides, carbohydrates, lipids, small molecules, and combinations thereof. Antigens may also be mixtures of several individual antigens. "Antigenicity" refers to the ability of an antigen to specifically bind to a T cell receptor or antibody and includes the reactivity of an antigen toward pre-existing antibodies in a subject. "Immunogenicity" refers to the ability of any antigen to induce an immune response and includes the intrinsic ability of an antigen to generate antibodies in a subject.

As used herein, the term "cloning" refers to the process of ligating a polynucleotide into a vector and transferring it into an appropriate host cell for duplication during propagation of the host.

The terms "control," "reference level," and "reference" are used herein interchangeably. The reference level may be a predetermined value or range, which is employed as a benchmark against which to assess the measured result.

"Control group" as used herein refers to a group of control subjects. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having CRC. A description of ROC analysis is provided in P. J. Heagerty et al. (*Biometrics* 2000, 56, 337-44), the disclosure of which is hereby incorporated by reference in its entirety. Alternatively, cutoff values may be determined by a quartile analysis of biological samples of a patient group. For example, a cutoff value may be determined by selecting a value that corresponds to any value in the 25th-75th percentile range, preferably a value that corresponds to the 25th percentile, the 50th percentile or the 75th percentile, and more preferably the 75th percentile. Such statistical analyses may be performed using any method known in the art and can be implemented through any number of commercially available software packages (e.g., from Analyse-it Software Ltd., Leeds, UK; StataCorp LP, College Station, TX; SAS Institute Inc., Cary, NC). The healthy or normal levels or ranges for a target or for a protein activity or level may be defined in accordance with standard practice. A control may be a molecule, or sample comprising a molecule, that is different from an ion channel polypeptide as detailed herein. A control may be a subject, or a sample therefrom, without an ion channel polypeptide as detailed herein. A control may be a subject, or a sample therefrom, whose disease state is known. The subject, or sample therefrom, may be healthy, diseased, diseased prior to treatment, diseased during treatment, or diseased after treatment, or a combination thereof. The term "normal subject" as used herein means a healthy subject, i.e. a subject having no clinical signs or symptoms of disease. The normal subject may be clinically evaluated for otherwise undetected signs or symptoms of disease, which evaluation may include routine physical examination and/or laboratory testing. In some embodiments, the control is a healthy control.

The term "host cell" is a cell that is susceptible to transformation, transfection, transduction, conjugation, and the like with a nucleic acid construct or expression vector. Host cells can be derived from plants, bacteria, yeast, fungi, insects, animals, etc. In some embodiments, the host cell includes *Escherichia coli*.

The terms "naturally occurring" or "native", as used herein to describe a polynucleotide or polypeptide, each refer to a composition that can be found in nature as distinct from being artificially produced or isolated by man. Generally, a native sequence refers to a functional unit, for example, an open reading frame. Thus, a nucleotide or amino acid sequence present in an organism, which can be isolated from a source in nature and which has not been intentionally modified by man in the laboratory, is naturally occurring. The term "native protein" may indicate that a protein does not contain amino acid residues encoded by vector sequences; the native protein may contain only those amino acids found in the protein as it occurs in nature. A native protein may be endogenously expressed by a cell. A native protein may be produced by recombinant means or may be isolated from a naturally occurring source.

An "open reading frame" includes at least 3 consecutive codons which are not stop codons. The term "codon" as used herein refers to any group of three consecutive nucleotide bases in a given messenger RNA molecule, or coding strand of DNA or polynucleotide that specifies a particular amino acid, a starting signal, or a stopping signal for translation. The term codon also refers to base triplets in a DNA strand.

The term "operatively linked" or "operably linked," as used herein, refers to a functional combination between a promoter region and a nucleotide sequence such that the transcription of the nucleotide sequence is controlled and regulated by the promoter region. Techniques for operatively linking a promoter region to a nucleotide sequence are known in the art. The term may refer to the linkage of polynucleotide sequences in such a manner that a polynucleotide molecule capable of directing the transcription of a given gene and/or the synthesis of a desired protein molecule is produced. The term also refers to the linkage of amino acid sequences in such a manner so that a functional protein is produced.

The term "expression vector" or "vector" indicates a plasmid, a cosmid, a virus, or another medium, known in the art, into which a nucleic acid sequence for encoding a desired protein can be inserted or introduced. A vector refers to a polynucleotide molecule having nucleotide sequences that enable its replication in a host cell. A vector can also include nucleotide sequences to permit ligation of nucleotide sequences within the vector, wherein such nucleotide sequences are also replicated in a host cell. A vector can also mediate recombinant production of a ion channel polypeptide, as described further herein.

"Polynucleotide" as used herein can be single stranded or double stranded, or can contain portions of both double stranded and single stranded sequence. The polynucleotide can be nucleic acid, natural or synthetic, DNA, genomic DNA, cDNA, RNA, or a hybrid, where the polynucleotide can contain combinations of deoxyribo- and ribo-nucleotides, and combinations of bases including uracil, adenine, thymine, cytosine, guanine, inosine, xanthine hypoxanthine, isocytosine, and isoguanine. Polynucleotides can be obtained by chemical synthesis methods or by recombinant methods.

Polynucleotides are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a polynucleotide sequence, even if internal to a larger oligonucleotide, also may be said to have 5' and 3' ends. In either a linear or circular polynucleotide, discrete elements are referred to as being "upstream" or 5' of the "downstream" or 3' elements. This terminology reflects the fact that transcription proceeds in a 5' to 3' fashion along the polynucleotide strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term "gene" means the polynucleotide sequence comprising the coding region of a gene, e.g., a structural gene, and the including sequences located adjacent to the coding region on both the 5' and 3' ends for a distance of about 1 kb on either end such that the gene corresponds to the length of the full-length mRNA. The sequences which are located 5' or upstream of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA, for example, heterogeneous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

As used herein, an oligonucleotide or polynucleotide "having a nucleotide sequence encoding a gene" means a polynucleotide sequence comprising the coding region of a gene, or in other words, the nucleic acid sequence which encodes a gene product. The coding region may be present in either a cDNA, genomic DNA, or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the vector may contain endogenous enhancers/promoters, splice junctions, intervening sequences, polyadenylation signals, etc., or a combination of both endogenous and exogenous control elements.

A "peptide" or "polypeptide" is a linked sequence of two or more amino acids linked by peptide bonds. The polypeptide can be natural, synthetic, or a modification or combination of natural and synthetic. Peptides and polypeptides include proteins such as binding proteins, receptors, and antibodies. The terms "polypeptide", "protein," and "peptide" are used interchangeably herein. "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. "Domains" are portions of a polypeptide that form a compact unit of the polypeptide and are typically 15 to 350 amino acids long. Exemplary domains include domains with enzymatic activity or ligand binding activity. Typical domains are made up of sections of lesser organization such as stretches of beta-sheet and alpha-helices. "Tertiary structure" refers to the complete three dimensional structure of a polypeptide monomer. "Quaternary structure" refers to the three dimensional structure formed by the noncovalent association of independent tertiary units. A "motif" is a portion of a polypeptide sequence and includes at least two amino acids. A motif may be 2 to 20, 2 to 15, or 2 to 10 amino acids in length. In some embodiments, a motif includes 3, 4, 5, 6, or 7 sequential amino acids. A domain may be comprised of a series of the same type of motif.

The phrases "pharmaceutically acceptable" or "pharmacologically acceptable" refer to molecular entities and compositions that do not produce an adverse, allergic, or other untoward reaction when administered to an animal, or human. As used herein, "pharmaceutically acceptable carrier" includes any and all solvents, dispersion media, coatings, antibacterial and antifungal agents, isotonic and absorption delaying agents, and the like. In some embodiments, a carrier includes a solution at neutral pH. In some embodiments, a carrier includes a salt. In some embodiments, a carrier includes a buffered solution.

"Recombinant" when used with reference, e.g., to a cell, or nucleic acid, protein, or vector, indicates that the cell, nucleic acid, protein, or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed, or not expressed at all. For example, the term "recombinant DNA molecule" as used herein refers to a DNA molecule which is comprised of segments of DNA joined together by means of molecular biological techniques. The term "recombinant protein" or "recombinant polypeptide" as used herein refers to a protein molecule which is expressed from a recombinant DNA molecule or recombinant polynucleotide.

As used herein, the term "restriction endonuclease" or "restriction enzyme" refers to a member or members of a classification of catalytic molecules that bind a cognate sequence of a polynucleotide and cleave the polynucleotide at a precise location within that sequence. Restriction endonuclease may be bacterial enzymes. Restriction endonuclease may cut double-stranded DNA at or near a specific nucleotide sequence.

As used herein, "recognition site" or "restriction site" refers to a sequence of specific bases or nucleotides that is recognized by a restriction enzyme if the sequence is present in double-stranded DNA; or, if the sequence is present in single-stranded RNA, the sequence of specific bases or nucleotides that would be recognized by a restriction enzyme if the RNA was reverse transcribed into cDNA and the cDNA employed as a template with a DNA polymerase to generate a double-stranded DNA; or, if the sequence is present in single-stranded DNA, the sequence of specific bases or nucleotides that would be recognized by a restriction enzyme if the single-stranded DNA was employed as a template with a DNA polymerase to generate a double-stranded DNA; or, if the sequence is present in double-stranded RNA, the sequence of specific bases or nucleotides that would be recognized by a restriction enzyme if either strand of RNA was reverse transcribed into cDNA and the cDNA employed as a template with a DNA polymerase to generate a double-stranded DNA. The term "unique restriction enzyme site" or "unique recognition site" indicates that the recognition sequence for a given restriction enzyme appears once within a polynucleotide.

As used herein, the term "regulatory element" refers to a genetic element which controls some aspect of the expression of polynucleotide sequences. For example, a promoter is a regulatory element that facilitates the initiation of transcription of an operably linked coding region. Other regulatory elements may include splicing signals, polyadenylation signals, termination signals, and the like. Transcriptional control signals in eukaryotes include "promoter" and "enhancer" elements. Promoters and enhancers include short arrays of polynucleotide sequences that interact specifically with cellular proteins involved in transcription (Maniatis et al., Science, 236: 1237 (1987), incorporated herein by reference). Conventional promoter and enhancer elements have been isolated from a variety of eukaryotic sources such as, for example, genes in yeast, insect and mammalian cells, and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see Voss et al., Trends Biochem. Sci., 11:287 (1986) and Maniatis et al., supra (1987)). For example, the SV40 early gene enhancer is very active in a wide variety of cell types from many mammalian species and has been widely used for the expression of proteins in mammalian cells (Dijkema et al. EMBO J. 1985, 4, 761). Two other examples of promoter/enhancer elements active in a broad range of mammalian cell types include those from the human elongation factor 10 gene (Uetsuki et al. J. Biol. Chem. 1989, 264, 5791; Kim et al. Gene, 1990, 91, 217; Mizushima et al. Nuc. Acids. Res. 1990, 18, 5322) and the long terminal repeats of the Rous sarcoma virus (Gorman et al. Proc. Natl. Acad. Sci. USA 1982, 79, 6777) and the human cytomegalovirus (Boshart et al. Cell 1985, 41, 521).

As used herein, the term "promoter/enhancer" denotes a segment of a polynucleotide that contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

"Replication origins" are unique polynucleotide segments that contain multiple short repeated sequences that are recognized by multimeric origin-binding proteins and which play a key role in assembling DNA replication enzymes at the origin site.

The presence of "splicing signals" on an expression vector often results in higher levels of expression of the recombinant transcript. Splicing signals mediate the removal of introns from the primary RNA transcript and consist of a splice donor and acceptor site (Sambrook et al., Molecular Cloning: A Laboratory Manual, 2nd ed., Cold Spring Harbor Laboratory Press, New York (1989) pp. 16.7-16.8). An example of a splice donor and acceptor site is the splice junction from the 16S RNA of SV40.

As used herein the term "portion" when in reference to a protein or polynucleotide (as in "a portion of a given protein") refers to fragments of that protein or polynucleotide. The protein fragments may range in size from two or more amino acid residues to the entire amino acid sequence minus one amino acid. Polynucleotide fragments may range in size from two or more nucleotides to the entire polynucleotide sequence minus one nucleotide.

As used herein, the term "fusion protein" refers to a chimeric protein containing the protein of interest joined to a different peptide or protein fragment. The fusion partner may, for example, enhance the solubility of a linked protein of interest, allow identification and/or purification of the recombinant fusion protein, may direct expression or localization of the protein, may provide an epitope tag or affinity domain to allow identification and/or purification of the recombinant fusion protein, e.g., from a host cell which expresses the fusion or a culture supernatant of that cell, or both, or may have another property or activity, e.g., two functional enzymes can be fused to produce a single protein with multiple enzymatic activities. If desired, the fusion protein may be removed from the protein of interest by a variety of enzymatic or chemical means known to the art. Thus, examples of fusion protein producing sequences useful in the vectors of the invention may include motifs as detailed herein, epitope tag encoding sequences, affinity domain encoding sequences, fluorescent proteins, or other functional protein encoding sequences, and the like. The use of the term "functional protein encoding sequence," as used herein, indicates that the fusion protein producing element of a vector encodes a protein or peptide having a particular activity, such as an enzymatic activity, e.g., luciferase or dehalogenase, a binding activity, and the like, e.g., thioredoxin. For example, a functional protein encoding sequence may encode a kinase catalytic domain (Hanks and Hunter, FASEB J. 1995, 9, 576-595), producing a fusion protein that can enzymatically add phosphate moieties to particular amino acids, or may encode a Src Homology 2 (SH2) domain (Sadowski et al. Mol. Cell. Bio. 1986, 6, 4396; Mayer and Baltimore, Trends Cell. Biol. 1993, 3, 8), producing a fusion protein that specifically binds to phosphorylated tyrosines.

"Sample" or "test sample" as used herein can mean any sample in which the presence and/or level of a target is to be detected or determined or any sample comprising an agent, cell, or an ion channel polypeptide as described herein. Samples may include liquids, solutions, emulsions, or suspensions. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

As used herein, the term "selectable marker" or "selectable marker gene" refers to the use of a gene which encodes an enzymatic activity that confers the ability to grow in medium lacking what would otherwise be an essential nutrient (e.g., the TRPI gene in yeast cells), and/or confer upon the cell resistance to an antibiotic or drug in which the selectable marker is expressed. Selection markers may provide a means to select for or against growth of cells which have been successfully transformed with a vector containing the selection marker sequence and express the marker. A selectable marker may be used to confer a particular phenotype upon a host cell. When a host cell must express a selectable marker to grow in selective medium, the marker is said to be a positive selectable marker (e.g., drug or antibiotic resistance genes which confer the ability to grow in the presence of the appropriate antibiotic, or enable cells to detoxify an exogenously added drug that would otherwise kill the cell). Another example of a positive selection marker is a an auxotrophic marker, which allows cells to synthesize an essential component (usually an amino acid) while grown in media which lacks that essential component. Selectable auxotrophic gene sequences include, for example, hisD, which allows growth in histidine free media in the presence of histidinol. Selectable markers can also be used to select against host cells containing a particular gene (e.g., the sacB gene which, if expressed, kills the bacterial host cells grown in medium containing 5% sucrose); selectable markers used in this manner are referred to as negative selectable markers or counter-selectable markers. In some embodiments, selectable markers include resistance genes such as antibiotic resistance genes.

"Subject" as used herein can mean a mammal that wants or is in need of the herein described ion channel polypeptides. The subject may be a patient. The subject may be a human or a non-human animal. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be of any age or stage of development, such as, for example, an adult, an adolescent, or an infant. In some embodiments, the subject is human. In some embodiments, the subject has a specific genetic marker.

"Substantially identical" can mean that a first and second amino acid sequence are at least 60%, 65%, 70%, 75%, 80%, 85%, 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 amino acids.

A "therapeutically effective amount," or "effective dosage," or "effective amount" as used interchangeably herein unless otherwise defined, means a dosage of an agent or drug effective for periods of time necessary, to achieve the desired therapeutic result. An effective dosage may be determined by a person skilled in the art and may vary according to factors such as the disease state, age, sex, and weight of the individual, and the ability of the drug to elicit a desired response in the individual. This term as used herein may also refer to an amount effective at bringing about a desired in vivo effect in a subject. A therapeutically effective amount may be administered in one or more administrations (e.g., the composition may be given as a preventative treatment or therapeutically at any stage of disease progression, before or after symptoms, and the like), applications, or dosages, and is not intended to be limited to a particular formulation, combination, or administration route. It is within the scope of the present disclosure that the drug may be administered at various times during the course of treatment of the subject. The times of administration and dosages used will depend on several factors, such as the goal of treatment (e.g., treating v. preventing), condition of the subject, etc. and can be readily determined by one skilled in the art. A therapeutically effective amount is also one in which any toxic or detrimental effects of substance are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The terms "transformation" and "transfection" as used herein refer to the introduction of foreign DNA or polynucleotide into prokaryotic or eukaryotic cells. Transformation of prokaryotic cells may be accomplished by a variety of means known to the art including, for example, the treatment of host cells with $CaCl_2$ to make competent cells, electroporation, etc. Transfection of eukaryotic cells may be accomplished by a variety of means known to the art including, for example, calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The terms "treat," "treated," or "treating" as used herein refers to a therapeutic wherein the object is to slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment also includes prolonging survival as compared to expected survival if not receiving treatment. "Treatment" or "treating," when referring to protection of a subject from a disease, may include suppressing, repressing, ameliorating, or completely eliminating the disease. Preventing the disease involves administering a composition of the present invention to a subject prior to onset of the disease. Suppressing the disease involves administering a composition of the present invention to a subject after induction of the disease but before its clinical appearance. Repressing or ameliorating the disease involves administering a composition of the present invention to a subject after clinical appearance of the disease.

"Variant" as used herein with respect to a polynucleotide means (i) a portion or fragment of a referenced nucleotide sequence; (ii) the complement of a referenced nucleotide sequence or portion thereof; (iii) a polynucleotide that is substantially identical to a referenced polynucleotide or the complement thereof; or (iv) a polynucleotide that hybridizes under stringent conditions to the referenced polynucleotide, complement thereof, or a sequences substantially identical thereto.

A "variant" can further be defined as a peptide or polypeptide that differs in amino acid sequence by the insertion, deletion, or conservative substitution of amino acids, but retain at least one biological activity. Representative examples of "biological activity" include the ability to be bound by a specific antibody or polypeptide or to promote an immune response. Variant can mean a substantially identical sequence. Variant can mean a functional fragment thereof. Variant can also mean multiple copies of a polypeptide. The multiple copies can be in tandem or separated by a linker. Variant can also mean a polypeptide with an amino acid sequence that is substantially identical to a referenced polypeptide with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids. See Kyte et al., *J. Mol. Biol.* 1982, 157, 105-132. The hydropathic index of an amino acid is based on a consideration of its hydrophobicity and charge. It is known in the art that amino acids of similar hydropathic indexes can be substituted and still retain protein function. In one aspect, amino acids having hydropathic indices of ±2 are substituted. The hydrophobicity of amino acids can also be used to reveal substitutions that would result in polypeptides retaining biological function. A consideration of the hydrophilicity of amino acids in the context of a polypeptide permits calculation of the greatest local average hydrophilicity of that polypeptide, a useful measure that has been reported to correlate well with antigenicity and immunogenicity, as discussed in U.S. Pat. No. 4,554,101, which is fully incorporated herein by reference. Substitution of amino acids having similar hydrophilicity values can result in polypeptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant can be a polynucleotide sequence that is substantially identical over the full length of the full gene sequence or a fragment thereof. The polynucleotide sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant can be an amino acid sequence that is substantially identical over the full length of the amino acid sequence or fragment thereof. The amino acid sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

2. Prokaryotic Ion Channel Polypeptides

Provided herein are prokaryotic ion channel polypeptides and vectors encoding the same. Voltage-gated ion channels are a class of transmembrane proteins that provides a basis for cellular excitability and the ability to transmit information via ion-generated membrane potentials. In response to changes in membrane potentials, these proteins may mediate ion flux through selective channels in a cell membrane. If channel density is high enough, a regenerative depolarization results, which is called an action potential. The voltage-gated ion channels are responsible for the generation and propagation of action potentials in most electrically excitable cells, including neurons, heart cells, and muscle. Electrical activity is triggered by depolarization of the membrane, which opens channels through the membrane that are highly selective for ions. Ions are then driven intracellularly through open channels by an electrochemical gradient. The voltage-gated ion channel may display voltage-gated ion conductance across a lipid bilayer or membrane.

Although ion-based action potentials in different tissues may be similar, electrophysiological studies have demonstrated that multiple structurally and functionally distinct ion channels exist. Voltage-gated ion channels may be identified or classified by function, by structure (secondary and/or tertiary), and by sequence homology (primary structure). A hallmark of the voltage-gated ion channels are the six putative transmembrane spanning helices S1-S6 and the "PVP" motif (proline-valine-proline). Within the larger super-family are various families including potassium gated (Kv), sodium gated (Nav), and calcium gated (Cav) ion channels. The ion channel may be a sodium ion channel or a calcium ion channel. In some embodiments, the ion channel polypeptide provided herein is sodium gated (Nav). In some embodiments, the ion channel polypeptide is a prokaryotic voltage-gated ion channel polypeptide. In some embodiments, the ion channel polypeptide is a prokaryotic sodium-gated (BacNav) ion channel polypeptide. Prokaryotic sodium-gated ion channel polypeptides are homotetrameric and may be smaller than eukaryotic ion channels and/or encoded by a shorter polynucleotide. In some embodiments, the polypeptide comprises the wild-type BacNav ion channel from *Shewanella putrefaciens* (SEQ ID NO: 23).

The polypeptide may be a variant of any wild-type bacterial or prokaryotic polypeptide ion channel. For example, the polypeptide may be a variant of the wild-type BacNav ion channel from *Shewanella putrefaciens* (wild-type polypeptide from *Shewanella putrefaciens* is SEQ ID NO: 23). The amino acid positions detailed herein are relative to the wild-type BacNav ion channel from *Shewanella putrefaciens* (SEQ ID NO: 23) or a homolog thereof and are well conserved across BacNav ion channels from other bacteria and prokaryotes. The ion channel may comprise a polypeptide comprising the amino acid sequence of SEQ ID NO: 23 with at least one amino acid mutated to another amino acid. The ion channel polypeptide may include mutations that alter the voltage dependencies of gating. The ion channel polypeptide may include mutations at the extracellular negative charge clusters, for example, at amino acids E43, or D60, or a combination thereof. The ion channel polypeptide may include mutations at the intracellular negative charge clusters, for example, at amino acids D70, or E91, or a combination thereof. The ion channel polypeptide may include mutations at the S4 gating charges, for example, at amino acids R110, R113, R116, or R119, or a combination thereof. The ion channel polypeptide may include mutations at the activation gate, for example, at amino acid M232. The ion channel polypeptide may include mutations at the proximal "neck" region located between the activation gate and the four-helix bundle region of the C-terminal domain (CTD).

The ion channel polypeptide may include mutations that increase the speed of gating kinetics. The ion channel polypeptide may include mutations at the hinge region, for example, at amino acid A216. The ion channel polypeptide may include a hydrophilic substitution at amino acid L64. Hydrophobic amino acids include, for example, Ala, Val, Ile, Leu, Met, Phe, Tyr, Trp, Cys, and Pro. Hydrophilic amino acids include, for example, Arg, His, Lys, Asp, Glu, Ser, Thr, Asn, and Gln.

The ion channel polypeptide may include mutations that alter the ion specificity. The ion channel polypeptide may include mutations at the selectivity filter (LESWSM; SEQ ID NO: 7). For example, the ion channel polypeptide may include a mutation from LESWSM (SEQ ID NO: 7) to LDDWSD (SEQ ID NO: 8).

The ion channel polypeptide may include mutations that improve gene and/or membrane expression. The ion channel polypeptide may include synonymous mutations in the polynucleotide sequence for human codon optimization.

In some embodiments, the ion channel comprises a polypeptide comprising the amino acid sequence of SEQ ID NO: 23 with a mutation at E43 to another amino acid. In some embodiments, the ion channel comprises a polypeptide comprising the amino acid sequence of SEQ ID NO: 23 with a mutation at D60 to another amino acid. In some embodiments, the ion channel comprises a polypeptide corresponding to the amino acid sequence of SEQ ID NO: 23 with the mutation D60A, D60N, or D60S. In some embodiments, the ion channel comprises a polypeptide comprising the amino acid sequence of SEQ ID NO: 23 with a mutation at E43 and D60. In some embodiments, the ion channel comprises a polypeptide having a D60A mutation relative to the amino acid sequence of SEQ ID NO: 23. The ion channel polypeptide may further comprise additional mutations relative to SEQ ID NO: 23.

a. Export Motifs and Tags

The ion channel polypeptide may further include one or more motifs such as an export motif or other signaling sequence. The motif may direct the ion channel polypeptide to certain cellular locations such as the cellular membrane. Motifs may include a sequence directing the ion channel polypeptide for interaction with a particular receptor, antigen, or other polypeptide. Motifs may include a Golgi export motif. Golgi export motifs may include, for example, RSFVKKDGHCNVQFINV (SEQ ID NO: 13). Motifs may include a membrane trafficking motif. Membrane trafficking motifs or signals may include, for example, KSRITSEGEYIPLDQIDINV (SEQ ID NO: 14). The motif may be an endoplasmic reticulum (ER) export motif. ER export motifs may include, for example, SEQ ID NO: 4 (GVKESL), SEQ ID NO: 5 (DLRRSL), or SEQ ID NO: 6 (FCYENEV), or a combination thereof. The motif may be a membrane anchoring signal, such as, for example, PDZ binding motif, or Ankyrin-G binding motif. PDZ binding motifs may include, for example, SEI (SEQ ID NO: 9), SIV (SEQ ID NO: 10), TDV (SEQ ID NO: 11), or a combination thereof. Ankyrin-G binding motifs may include, for example, VPIAVAESD (SEQ ID NO: 12). The motif may be at the C-terminus, at the N-terminus, at an internal location of the ion channel polypeptide, or a combination thereof. In some embodiments, the ion channel polypeptide includes a motif at the C-terminal end. In some embodiments, the ion channel polypeptide further includes a fluorescent tag for detection. Fluorescent tags may include fluorescent polypeptides known in the art such as, for example, GFP, mEGFP, RFP, and YFP. The motif and/or tag may be encoded by a polynucleotide in the same reading frame as the polynucleotide encoding the ion channel polypeptide. The motif or tag may be linked to the ion channel polypeptide via a peptide linker. Peptide linkers may include, for example, (G)$_n$ wherein n is an integer from 1 to 10 (SEQ ID NO: 15); (GGGGS)$_n$ wherein n is an integer from 1 to 10 (SEQ ID NO: 16); (EAAAK)$_n$ wherein n is an integer from 1 to 10 (SEQ ID NO: 17); or (XP)$_n$ wherein n is an integer from 1 to 10 and X is any amino acid (SEQ ID NO: 18); or a combination thereof. In some embodiments, the ion channel polypeptide with motif is the wild-type BacNav ion channel polypeptide from *Shewanella putrefaciens* with ER export motif (SEQ ID NO: 24).

b. Polynucleotides

Further provided herein are polynucleotides encoding an ion channel polypeptide as detailed herein. In some embodiments, the ion channel polypeptide comprises an amino acid sequence encoded by a polynucleotide comprising SEQ ID NO: 1, SEQ ID NO: 2, or SEQ ID NO: 3. SEQ ID NO: 1 encodes the wild-type BacNav ion channel polypeptide from *Shewanella putrefaciens* (SEQ ID NO: 23), and SEQ ID NO: 2 and SEQ ID NO: 3 are human codon optimized versions of SEQ ID NO: 1. In some embodiments, the ion channel polypeptide with export motif comprises an amino acid sequence encoded by a polynucleotide comprising SEQ ID NO: 20, SEQ ID NO: 21, or SEQ ID NO: 22. SEQ ID NO: 20 encodes the wild-type BacNav ion channel polypeptide from *Shewanella putrefaciens* with ER export motif (SEQ ID NO: 24), and SEQ ID NO: 21 and SEQ ID NO: 22 are human codon optimized versions of SEQ ID NO: 20. To obtain expression of a polypeptide, one may subclone the polynucleotide encoding the polypeptide into an expression vector that contains a promoter to direct transcription, a transcription/translation terminator, and if for a nucleic acid encoding a protein, a ribosome binding site for translational initiation. The ion channel polypeptide may be expressed recombinantly in a host cell according to one of skill in the art. The ion channel polypeptide may be purified by any means known to one of skill in the art. In some embodiments, the ion channel polypeptide may be purified with chromatography.

i) Codon Optimization

The polynucleotide encoding the ion channel polypeptide may be codon optimized for enhanced expression in certain tissues or subjects. In some embodiments, the polynucleotide encoding the ion channel polypeptide may be codon optimized for enhanced expression in humans.

ii) Vector

Mammalian voltage-gated ion channels are a greater molecular weight than prokaryotic ion channels, which makes it challenging to encode the mammalian ion channels in a vector. The prokaryotic ion channels detailed herein are smaller, that is, of decreased molecular weight compared to mammalian ion channels, and may be encoded by a vector. Accordingly, provided herein is an ion channel polypeptide encoded by a vector. Further provided is a vector encoding an ion channel polypeptide as detailed herein. Vectors may include viral vectors. In some embodiments, the vector is a lentivirus. In some embodiments, the vector is an adeno-associated virus (AAV) such as AAV9. A vector encoding an ion channel polypeptide may be used to transduce cells for expression of the ion channel polypeptide therein, which may be referred to as gene therapy. Cells may include fibroblasts (ventricular or dermal), glial cells, astrocytes, epicardial cells, cardiomyocytes, neurons, or a combination thereof. In some embodiments, the ion channel polypeptide is expressed in cardiomyocytes.

The ion channel polypeptide may be expressed with inward-rectifier potassium channel Kir2.1, or the gap junctional protein connexin-43 (Cx43), or a combination thereof. Cx43 may comprise a polypeptide having an amino acid sequence of SEQ ID NO: 26. Kir2.1 may comprise a polypeptide having an amino acid sequence of SEQ ID NO: 27. In some embodiments, the ion channel, Kir2.1, and Cx43 are encoded by the same or different vectors. In some embodiments, Kir2.1 and/or Cx43 are overexpressed from the same or different vectors. In some embodiments, Kir2.1 and/or Cx43 are expressed from the same or different promoters. The vector may encode the ion channel and Kir2.1. The vector may encode the ion channel and Cx43. The vector may encode the ion channel and Kir2.1 and Cx43. In some embodiments, Cx43, Kir2.1, or a combination thereof, are expressed by the genome of the transduced cell. In some embodiments, Cx43, Kir2.1, or a combination thereof, are expressed endogenously by the transduced cell. In some embodiments, the vector comprises a polynucleotide sequence of SEQ ID NO: 25, which includes a polynucleotide encoding the wild-type BacNav ion channel from *Shewanella putrefaciens* (SEQ ID NO: 23), a polynucleotide encoding GFP, and a CMV promotor.

Further provided herein is a system for heterologous expression of a functional ion channel. In some embodiments, the system includes a recombinantly expressed ion channel polypeptide as detailed herein, and a host cell comprising the recombinantly expressed ion channel polypeptide. In other embodiments of the invention, the system includes a vector comprising a polynucleotide encoding an ion channel polypeptide as detailed herein operatively linked to a promoter, and a host cell comprising the vector, wherein the host cell expresses the ion channel polypeptide.

c. Immunogenicity

In some embodiments, the prokaryotic ion channels detailed herein have low or reduced immunogenicity relative to a control. In some embodiments, the prokaryotic ion channels detailed herein have low or reduced antigenicity relative to a control. The antigen may be an ion channel. The antigen may be a prokaryotic ion channel. The antigen may be a cell engineered to express a prokaryotic ion channel. In some embodiments, the prokaryotic ion channels detailed herein, or cells engineered with the prokaryotic ion channels detailed herein, are immunosuppressive. Immunoreactivity may be assayed with a variety of methods known in the art, such as, for example, an allogeneic lymphocyte proliferation assay. An allogeneic lymphocyte proliferation assay may include monitoring the proliferation of peripheral blood mononuclear cells (PBMCs) with phytohemagglutinin (PHA), a known PBMC mitogen, as a positive control.

d. Pharmaceutical Compositions

The ion channel polypeptide as detailed herein, or a vector encoding the same, may be formulated into pharmaceutical compositions in accordance with standard techniques well known to those skilled in the pharmaceutical art. A composition may comprise the ion channel polypeptide or a vector encoding the ion channel polypeptide. The composition may further include a pharmaceutically acceptable carrier. The term "pharmaceutically acceptable carrier," as used herein, means a non-toxic, inert solid, semi-solid or liquid filler, diluent, encapsulating material or formulation auxiliary of any type. The composition may be prepared for administration to a subject. Such compositions comprising an ion channel polypeptide can be administered in dosages and by techniques well known to those skilled in the medical arts taking into consideration such factors as the age, sex, weight, and condition of the particular subject, and the route of administration.

Pharmaceutically acceptable carriers include, for example, diluents, lubricants, binders, disintegrants, colorants, flavors, sweeteners, antioxidants, preservatives, glidants, solvents, suspending agents, wetting agents, surfactants, emollients, propellants, humectants, powders, pH adjusting agents, and combinations thereof.

Suitable diluents include, for example, sugars such as glucose, lactose, dextrose, and sucrose; diols such as propylene glycol; calcium carbonate; sodium carbonate; sugar alcohols, such as glycerin; mannitol; sorbitol; cellulose; starch; and gelatin. The amount of diluent(s) in a systemic or topical composition may typically be about 50 to about 90%.

Suitable lubricants include, for example, silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil, and oil of theobroma. The amount of lubricant(s) in a systemic or topical composition may typically be about 5 to about 10%.

Suitable binders include, for example, polyvinyl pyrrolidone; magnesium aluminum silicate; starches such as corn starch and potato starch; gelatin; tragacanth; sucrose; and cellulose and its derivatives, such as sodium carboxymethylcellulose, ethyl cellulose, methylcellulose, microcrystalline cellulose, and hydroxypropyl methylcellulose. The amount of binder(s) in a systemic composition may typically be about 5 to about 50%.

Suitable disintegrants include, for example, agar, alginic acid and the sodium salt thereof, effervescent mixtures, croscarmelose, crospovidone, sodium carboxymethyl starch, sodium starch glycolate, clays, and ion exchange resins. The amount of disintegrant(s) in a systemic or topical composition may typically be about 0.1 to about 10%.

Suitable colorants include, for example, a colorant such as an FD&C dye. When used, the amount of colorant in a systemic or topical composition may typically be about 0.005 to about 0.1%.

Suitable flavors include, for example, menthol, peppermint, and fruit flavors. The amount of flavor(s), when used, in a systemic or topical composition may typically be about 0.1 to about 1.0%.

Suitable sweeteners include, for example, aspartame and saccharin, or a combination thereof. The amount of sweetener(s) in a systemic or topical composition may typically be about 0.001 to about 1%.

Suitable antioxidants include, for example, butylated hydroxyanisole ("BHA"), butylated hydroxytoluene ("BHT"), and vitamin E. The amount of antioxidant(s) in a systemic or topical composition may typically be about 0.1 to about 5%.

Suitable preservatives include, for example, benzalkonium chloride, methyl paraben, and sodium benzoate. The amount of preservative(s) in a systemic or topical composition may typically be about 0.01 to about 5%.

Suitable glidants include, for example, silicon dioxide. The amount of glidant(s) in a systemic or topical composition may typically be about 1 to about 5%.

Suitable solvents include, for example, water, isotonic saline, ethyl oleate, glycerine, castor oils, hydroxylated castor oils, alcohols such as ethanol or isopropanol, methylene chloride, ethylene glycol monoethyl ether, diethylene glycol monobutyl ether, diethylene glycol monoethyl ether, dimethylsulfoxide, dimethyl formamide, tetrahydrofuran, and phosphate buffer solutions, and combinations thereof. The amount of solvent(s) in a systemic or topical composition is typically from about 0 to about 100%, or 0% to about 95%.

Suitable suspending agents include, for example, AVICEL RC-591 (from FMC Corporation of Philadelphia, PA) and sodium alginate. The amount of suspending agent(s) in a systemic or topical composition may typically be about 1 to about 8%.

Suitable surfactants include, for example, lecithin, Polysorbate 80, and sodium lauryl sulfate, and the TWEENS from Atlas Powder Company of Wilmington, Delaware. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition may typically be about 0.1% to about 5%.

Suitable emollients include, for example, stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition may typically be about 5% to about 95%.

Suitable propellants include, for example, propane, butane, isobutane, dimethyl ether, carbon dioxide, nitrous oxide, and combinations thereof. The amount of propellant in a topical composition may be about 0% to about 95%.

Suitable humectants include, for example, glycerin, sorbitol, sodium 2-pyrrolidone-5-carboxylate, soluble collagen, dibutyl phthalate, gelatin, and combinations thereof. The amount of humectant in a topical composition may be about 0% to about 95%.

Suitable powders include, for example, beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition may typically be 0% to 95%.

Suitable pH adjusting additives include, for example, HCl or NaOH in amounts sufficient to adjust the pH of a topical pharmaceutical composition.

In some embodiments, the pharmaceutically acceptable carrier is a sugar such as lactose, glucose, and sucrose. In some embodiments, the pharmaceutically acceptable carrier is a starch such as, for example, corn starch and potato starch. In some embodiments, the pharmaceutically acceptable carrier is cellulose and its derivatives such as, but not limited to, sodium carboxymethyl cellulose, ethyl cellulose and cellulose acetate. In some embodiments, the pharmaceutically acceptable carrier is powdered tragacanth, malt, gelatin, or talc. In some embodiments, the pharmaceutically acceptable carrier is an excipient such as, but not limited to, cocoa butter and suppository waxes. In some embodiments, the pharmaceutically acceptable carrier is oil such as, but not limited to, peanut oil, cottonseed oil, safflower oil, sesame oil, olive oil, corn oil and soybean oil. In some embodiments, the pharmaceutically acceptable carrier is a glycol, such as propylene glycol. In some embodiments, the pharmaceutically acceptable carrier is an ester such as, but not limited to, ethyl oleate and ethyl laurate. In some embodiments, the pharmaceutically acceptable carrier is an agar. In some embodiments, the pharmaceutically acceptable carrier is a buffering agent such as, but not limited to, magnesium hydroxide and aluminum hydroxide. In some embodiments, the pharmaceutically acceptable carrier is alginic acid, pyrogen-free water, isotonic saline, Ringer's solution, ethyl alcohol, or a phosphate buffer solution. In some embodiments, the pharmaceutically acceptable carrier is a non-toxic compatible lubricant such as, but not limited to, sodium lauryl sulfate and magnesium stearate.

Compositions for oral administration can have various dosage forms. For example, solid forms include tablets, capsules, granules, and bulk powders. Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Capsules (including implants, time release, and sustained release formulations) typically include a compound, and a carrier including one or more diluents disclosed above in a capsule comprising gelatin. Granules typically comprise a compound, and preferably glidants such as silicon dioxide to improve flow characteristics. Implants can be of the biodegradable or the non-biodegradable type.

Compositions for oral administration can have solid forms. Solid oral compositions may be coated by conventional methods, typically with pH or time-dependent coatings, such that a compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT® coatings (available from Evonik Industries of Essen, Germany), waxes, and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Compositions for topical administration can be applied locally to the skin and may be in any form including solids, solutions, oils, creams, ointments, gels, lotions, shampoos, leave-on and rinse-out hair conditioners, milks, cleansers, moisturizers, sprays, skin patches, and the like. The carrier of the topical composition preferably aids penetration of the compound into the skin. In the topical compositions, the carrier includes a topical carrier. Suitable topical carriers can include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications may include propylene glycol, dimethyl isosorbide, and water, and even more particularly, phosphate buffered saline, isotonic water, deionized water, monofunctional alcohols, and symmetrical alcohols. The carrier of a topical composition may further include one or more ingredients selected from emollients, propellants, solvents, humectants, thickeners, powders, fragrances, pigments, and preservatives, all of which are optional.

Although the amounts of components in the compositions may vary depending on the type of composition prepared, in general, systemic compositions may include 0.01% to 50% of an ion channel polypeptide or vector and 50% to 99.99% of one or more carriers. Compositions for parenteral administration may typically include 0.1% to 10% of an ion channel polypeptide or vector and 90% to 99.9% of one or more carriers. Oral dosage forms may include, for example, at least about 5%, or about 25% to about 50% of an ion channel polypeptide or vector. The oral dosage compositions may include about 50% to about 95% of carriers, or from about 50% to about 75% of carriers. The amount of the carrier employed in conjunction with a disclosed ion channel polypeptide or vector is sufficient to provide a practical quantity of composition for administration per unit dose of the compound. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

e. Administration

The ion channel polypeptide as detailed herein or a vector encoding the same, or the pharmaceutical composition comprising the same, may be administered to a subject. The ion channel polypeptide or vector can be formulated into a composition and administered in dosages and by techniques well known to those skilled in the medical arts taking into consideration such factors as the age, sex, weight, and condition of the particular subject, and the route of administration. The ion channel polypeptide, or vector encoding it, can be administered prophylactically or therapeutically. In prophylactic administration, the ion channel polypeptide, or vector encoding it, can be administered in an amount sufficient to induce a response. In therapeutic applications, the ion channel polypeptide, or vector encoding it, is administered to a subject in need thereof in an amount sufficient to elicit a therapeutic effect. An amount adequate to accomplish this is defined as "therapeutically effective dose." Amounts effective for this use will depend on, e.g., the particular composition of the ion channel polypeptide regimen administered, the manner of administration, the stage and severity of the disease, the general state of health of the patient, and the judgment of the prescribing physician.

The ion channel polypeptide as detailed herein or a vector encoding the same, or the pharmaceutical composition comprising the same, can be administered by methods well known in the art as described in Donnelly et al. (Ann. Rev. Immunol. 1997, 15, 617-648); Feigner et al. (U.S. Pat. No. 5,580,859, issued Dec. 3, 1996); Feigner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The ion channel polypeptide as detailed herein or a vector encoding the same can be complexed to particles or beads that can be administered to an individual, for example, using a vaccine gun. One skilled in the art would know that the choice of a pharmaceutically acceptable carrier, including a physiologically acceptable compound, depends, for example, on the route of administration.

The ion channel polypeptide, or vector encoding it, can be delivered via a variety of routes. Typical delivery routes include parenteral administration, e.g., intradermal, intramuscular or subcutaneous delivery. Other routes include oral administration, sublingual, intranasal, intravaginal, transdermal, intravenous, parenteral, subcutaneous, intramuscular, intraarterial, intratumoral, intraperitoneal, intrathecal, rectal, intravaginal, and epidermal routes. In some embodiments, the ion channel polypeptide, or vector encoding it, is administered intravenously, intraarterially, or intraperitoneally to the subject.

The ion channel polypeptide, or vector encoding it, can be a liquid preparation such as a suspension, syrup, or elixir. The ion channel polypeptide, or vector encoding it, can be incorporated into liposomes, microspheres, or other polymer matrices (such as by a method described in Feigner et al., U.S. Pat. No. 5,703,055; Gregoriadis, Liposome Technology, Vols. I to III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

In some embodiments, the ion channel polypeptide, or vector encoding it, is administered in a controlled release formulation. The ion channel polypeptide, or vector encoding it, may be released into the circulation, for example. In some embodiments, the ion channel polypeptide, or vector encoding it, may be released over a period of at least about 1 day, at least about 2 days, at least about 3 days, at least about 4 days, at least about 5 days, at least about 6 days, at least about 7 days, at least about 1 week, at least about 1.5 weeks, at least about 2 weeks, at least about 2.5 weeks, at least about 3.5 weeks, at least about 4 weeks, or at least about 1 month.

3. Voltage Gated Ion Channel-Related Conditions

The ion channels detailed herein may be used to treat a voltage gated ion channel-related condition. Voltage gated ion channel-related conditions may include, for example, heart arrhythmia, chronic atrial fibrillation, damage from myocardial infarction, damage from stroke, chronic ischemia, any condition listed in TABLE 1, or a combination thereof. Shown in TABLE 1 are eukaryotic sodium channels and the conditions that are associated with or result from their loss of function, which may also be referred to as loss-of-function channelopathies.

TABLE 1

Conditions associated with loss of function of a eukaryotic sodium channel.

| Gene | Channel | Tissue Expression | Loss-of-Function Channelopathies |
|------|---------|-------------------|----------------------------------|
| SCN1A | Nav1.1 | CNS, PNS | Dravet Sydrome, Severe idiopathic generalized epilepsy of infancy |
| SCN2A | Nav1.2 | CNS, PNS | Benign familial neonatal-infantile seizures, Autism spectrum disorders |
| SCN3A | Nav1.3 | CNS, PNS | Epilepsy |
| SCN4A | Nav1.4 | Skeletal muscle | Hypokalemic Periodic Paralysis |
| SCN5A | Nav1.5 | Cardiac muscle | Brugada Syndrome Type 1 |
| SCN8A | Nav1.6 | CNS, PNS | Epilepsy, Ataxia |
| SCN9A | Nav1.7 | PNS | Congenital Insensitivity to Pain, Anosmia |
| SCN10A | Nav1.8 | PNS | Brugada Syndrome |
| SCN11A | Nav1.9 | PNS | |

* CNS, central nervous system; PNS, peripheral nervous system.

Voltage gated ion channel-related conditions may include those associated with or resulting from a mutation listed in TABLE 2, or the human mutation corresponding thereto. Shown in TABLE 2 are transgenic mice with mutations that result in loss-of-function of a sodium channel in the heart. The mutations currently known to be relevant for human disease are indicated with an asterisk (*). Voltage gated ion channel-related conditions may benefit from gene therapy to express an ion channel polypeptide as detailed herein. In some embodiments, the ion channels are expressed in the heart. When expressed in the heart, the ion channels may improve cardiac conduction; treat atrial fibrillations; terminate, reduce, or prevent arrhythmias; enhance cardiomyocyte contractility; or a combination thereof.

TABLE 2

List of transgenic mice with mutations that result in loss-of-function in sodium current in the heart.

| Protein | Mouse Transgenic Line | Mechanisms |
|---------|----------------------|------------|
| $Na_v1.5$ α-subunit | *Scn5a+/− | Reduced $Na_v1.5$ mRNA and protein expression Negative shift in $Na_v1.5$ inactivation curve (Papadatos, G. A., et al. *PNAS* 2002, 9, 6210-6215) |
| $Na_v1.5$ α-subunit | Scn5a ΔSIV knock-in (homozygous) | Reduced $Na_v1.5$ anchoring on lateral membranes due to loss of binding to PDZ domain of α1-syntrophin (Shy, D., et al. *Circulation* 2014, 130, 147-60) |
| $Na_v\beta3$ | *Scn3b−/− | Reduced membrane expression or percentage of functional $Na_v1.5$ channels Negative shift in $Na_v1.5$ inactivation curve (Hakim, P., et al. *Prog. Biophys. Mol. Biol.* 2008, 98, 251-266) |
| Ankyrin-G | *$Ank3^{flox/flox}$ × αMHC-cre | Decreased targeting of $Na_v1.5$ at intercalated disc membranes (Makara, M. A., et al. *Circ. Res.* 2014, 115, 929-938) |

TABLE 2-continued

List of transgenic mice with mutations that result in loss-of-function in sodium current in the heart.

| Protein | Mouse Transgenic Line | Mechanisms |
|---|---|---|
| Plakophilin-2 | *Pkp2+/− | Desmosomal deficiency leading to reduced $Na_v1.5$ localization at intercalated discs<br>Negative shift in $Na_v1.5$ inactivation curve<br>Slowed $Na_v1.5$ recovery from inactivation<br>(Cerrone, M., et al. *Cardiovasc. Res.* 2012, 95, 460-468; Grossmann, K. S., et al. *J. Cell Biol.* 2004, 167, 149-160) |
| Desmoglein-2 | αMHC-Dsg2-N271S | Decreased $Na_v1.5$ expression at intercalated disc membranes<br>(Rizzo, S., et al. *Cardiovasc. Res.* 2012, 95, 409-418; Pilichou, K., et al. *J. Exp. Med.* 2009, 206, 1787-1802) |
| GPD1-L | *$GPD1L^{flox/flox}$ × αMHC-cre | Decreased $Na_v1.5$ membrane trafficking<br>(Mehdi, H., et al. *Circulation* 2014, 130, A17871-A17871) |
| Ryanodine receptor 2 | RyR2-P2328S/ P2328S | Elevated cytosolic $Ca^{2+}$, leading to reduced $Na_v1.5$ protein and membrane expression<br>Positive shift in $Na_v1.5$ activation curve<br>Enhanced $I_{Na}$ slow inactivation<br>(Goddard, C. A., et al. *Acta Physiol. (Oxf)*. 2008, 194, 123-140; King, J. H., et al. *Cardiovasc. Res.* 2013, 99, 751-759) |
| PDK1 | $PDK1^{flox/flox}$ × αMHC-Cre | Increased activity of Foxo1 transcription factor, leading to decreased expression of $Na_v1.5$<br>(Han, Z., et al. *PLoS One* 2015, 10, e0122436) |

*Directly or indirectly linked to Brugada syndrome in humans.

4. Methods

The ion channel polypeptides may be encoded by a vector for administration to a subject for gene therapy. The ion channels detailed herein can be encoded by therapeutic vectors and used to manipulate human tissues whose function relies on sodium and/or calcium channels (such as, for example, heart, brain, skeletal muscle, pancreas).

a. Methods of Treating a Voltage Gated Ion Channel-Related Condition

Provided herein is a method of treating a voltage gated ion channel-related condition in a subject. The method may include administering to the subject a recombinant vector, such as a AAV9 vector, encoding an ion channel polypeptide as detailed herein. In some embodiments, the ion channel is a BacNav prokaryotic ion channel. In some embodiments, the BacNav prokaryotic ion channel polypeptide is expressed in the cardiomyocytes of the subject. In some embodiments, the voltage gated ion channel-related condition is selected from heart arrhythmia, chronic atrial fibrillation, damage from myocardial infarction, damage from stroke, and chronic ischemia. In some embodiments, the vector is administered to a coronary artery or a coronary sinus of the subject. In some embodiments, the vector is administered to the subject sublingually, orally, intranasally, intravenously, parenterally, subcutaneously, intramuscularly, intraperitoneally, rectally, intravaginally, or intrathecally. In some embodiments, the voltage gated ion channel is a sodium channel, a calcium channel, or a combination thereof.

b. Methods of Increasing the Conductivity of Cardiac Tissue

Provided herein is a method of increasing the conductivity of a cardiac tissue of a subject. The method may include administering to the subject a recombinant vector, such as a AAV9 vector, encoding an ion channel polypeptide as detailed herein. In some embodiments, the ion channel is a BacNav prokaryotic ion channel. In some embodiments, the BacNav prokaryotic voltage gated ion channel polypeptide is expressed in the cardiomyocytes of the subject. In some embodiments, the voltage gated ion channel-related condition is selected from heart arrhythmia, chronic atrial fibrillation, damage from myocardial infarction, damage from stroke, and chronic ischemia. In some embodiments, the vector is administered to a coronary artery or a coronary sinus of the subject. In some embodiments, the vector is administered to the subject sublingually, orally, intranasally, intravenously, parenterally, subcutaneously, intramuscularly, intraperitoneally, rectally, intravaginally, or intrathecally. In some embodiments, the voltage gated ion channel is a sodium channel, a calcium channel, or a combination thereof.

c. Methods of Increasing the Resistance to Conduction Block

Provided herein is a method of increasing the resistance to conduction block of a cardiac tissue of a subject. The method may include administering to the subject a recombinant vector, such as a AAV9 vector, encoding a BacNav prokaryotic ion channel polypeptide as detailed herein. In some embodiments, the BacNav prokaryotic ion channel polypeptide is expressed in the cardiomyocytes of the subject. In some embodiments, the voltage gated ion channel-related condition is selected from heart arrhythmia, chronic atrial fibrillation, damage from myocardial infarction, damage from stroke, and chronic ischemia. In some embodiments, the vector is administered to a coronary artery or a coronary sinus of the subject. In some embodiments, the vector is administered to the subject sublingually, orally, intranasally, intravenously, parenterally, subcutaneously, intramuscularly, intraperitoneally, rectally, intravaginally, or intrathecally. In some embodiments, the voltage gated ion channel is a sodium channel, a calcium channel, or a combination thereof.

d. Methods of Increasing the Upstroke Velocity of Cardiac Tissue

Provided herein is a method of increasing the upstroke velocity of a cardiac tissue of a subject. The method may include administering to the subject a recombinant vector, such as a AAV9 vector, encoding a BacNav prokaryotic ion channel polypeptide as detailed herein. In some embodiments, the BacNav prokaryotic ion channel polypeptide is expressed in the cardiomyocytes of the subject. In some embodiments, the voltage gated ion channel-related condition is selected from heart arrhythmia, chronic atrial fibrillation, damage from myocardial infarction, damage from stroke, and chronic ischemia. In some embodiments, the vector is administered to a coronary artery or a coronary sinus of the subject. In some embodiments, the vector is administered to the subject sublingually, orally, intranasally, intravenously, parenterally, subcutaneously, intramuscularly, intraperitoneally, rectally, intravaginally, or intrathecally. In some embodiments, the voltage gated ion channel is a sodium channel, a calcium channel, or a combination thereof.

5. Examples

Example 1

Materials and Methods

Characterization of human codon-optimized NavSheP D60A constructs. Human codon optimization of bacterial NavSheP D60A (bShePA) gene was performed via Genscript OptimumGene algorithm (Liu, X. et al. Google Patents, 2012) (hShePA) and ATUM Gene-GPS™ algorithm (Welch, M. et al. PloS One 2009, 4, e7002) (h2ShePA). Wild-type and codon-optimized sequences are listed below. Human codon optimized cDNAs were synthesized by respective companies and subsequently subcloned into CMV-driven, bi-cistronic lentiviral plasmids where they were linked with eGFP via the T2A peptide. Lentiviral plasmid containing the non-optimized channel co-expressed with eGFP (bShePA-T2A-eGFP) served as the control. Lentiviruses for each plasmid were made as described in the previous section, diluted to the same titer ($\sim 1.7 \times 10^8$ transduction units/mL), and transduced into HEK293 cells monoclonally derived for Kir2.1 expression. Flow cytometry was used to ensure similar percentage of transduced cells across all three groups and to evaluate average eGFP intensity in each group. Whole-cell patch clamp was performed to compare sodium current density and AP characteristics (upstroke, $APD_{80}$, and resting membrane potential) between three groups while optical mapping was performed to assess conduction properties.

Assessment of BacNav channel trafficking. Fusion of BacNav channel into the N- and C-termini of mEGFP was performed using the mEGFP-N1 (Addgene #54767, Cambridge, MA) and mEGFP-C1 (Addgene #54759, Cambridge, MA) plasmids, respectively. These plasmids contain CMV promoter driving expression of mEGFP, which displays the A206K mutation to prevent aggregation of GFP proteins (Zacharias, D. A., et al. Science 2002, 296, 913-916). Specifically, BacNav was subcloned into mEGFP-N1 using NheI and XhoI restriction sites to generate BacNav-mEGFP, while EcoRI and XbaI were used for ligation into mEGFP-C1 to obtain mEGFP-BacNav. Since NavRosD sequence contains internal EcoRI cut sites, XhoI and XbaI were chosen instead to generate mEGFP-NavRosD, followed by Quikchange mutagenesis (Agilent Technologies, Santa Clara, CA) to delete a base pair after XhoI and correct the open reading frame. Addition of endoplasmic reticulum export motifs (ERs) into mEGFP-BacNav constructs was achieved via polymerase chain reactions (PCR) using forward or reverse primers containing the ER DNA sequences. Three ER sequences were tested: ER1 (GVKESL) from Kv1.4, ER2 (DLRRSL) from Kv1.5, and ER3 (FCYENEV) from Kir2.1. HEK293 cells were seeded in tissue culture-treated 12-well plate at a density of $5 \times 10^4$ cells/cm$^2$ and transfected with each construct the next day using Lipofectamine 2000 transfection reagent (Life Technologies, Carlsbad, CA). Twenty-four hours after transfection, cells were dissociated and transferred onto fibronectin-coated (15 µg/mL) glass-bottom dishes, and live-cell images were taken 48 hours post transfection using inverted fluorescence microscope (Nikon TE2000) at 60× magnification. Patch clamp recordings and optical mapping for HEK293 cells transfected with selected constructs were performed 36-48 hours after transfection.

Cardiomyocyte-fibroblast co-cultures. NRVMs were isolated. To obtain cell population with higher percentages of fibroblasts, only one pre-plating step was performed. Cells were also seeded at a lower density ($1.5 \times 10^5$ cells/cm$^2$) in DMEM/F-12 medium supplemented with 10% horse serum, 1% penicillin, and 1% B12. Seeding media was replaced by maintenance media (DMEM/F12+5% FBS+10 µM EdU) 24 hours later. At day 2, NavSheP D60A lentivirus was added into the cultures in the presence of 8 ng/µL polybrene. Complete maintenance media change was performed every two days and cultures were mapped at day 5. Cells were continuously stimulated with a bipolar point electrode at gradually increasing rates until maximum capture rate was reached or reentry was induced.

Example 2

Improvement of BacNav Expression Via Codon Optimization

Figure 1C:
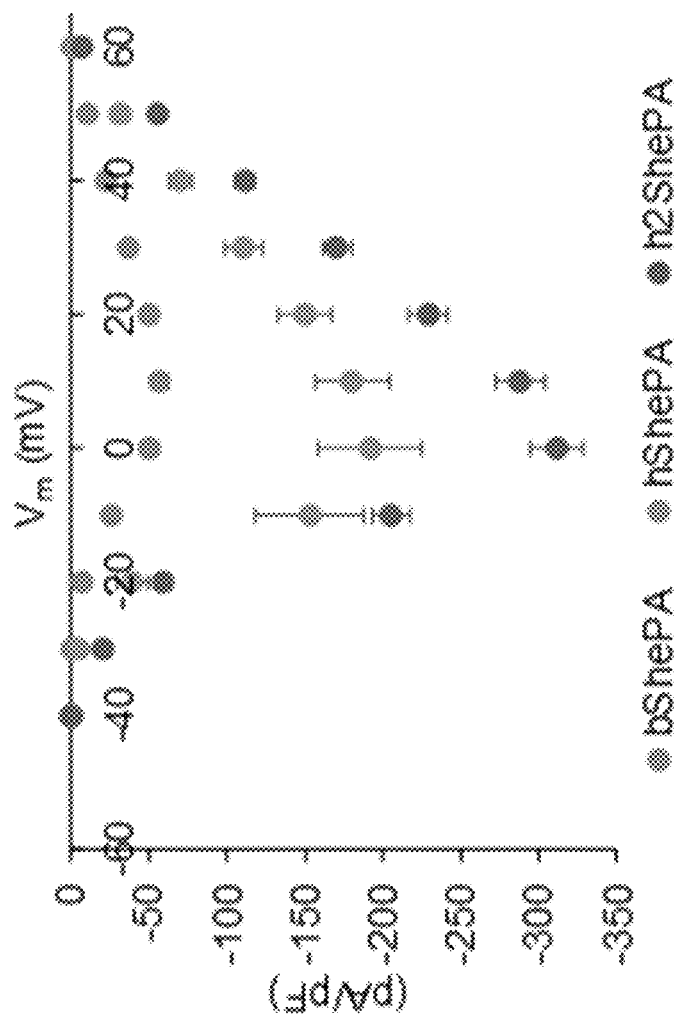
Figures 1E, 1F:
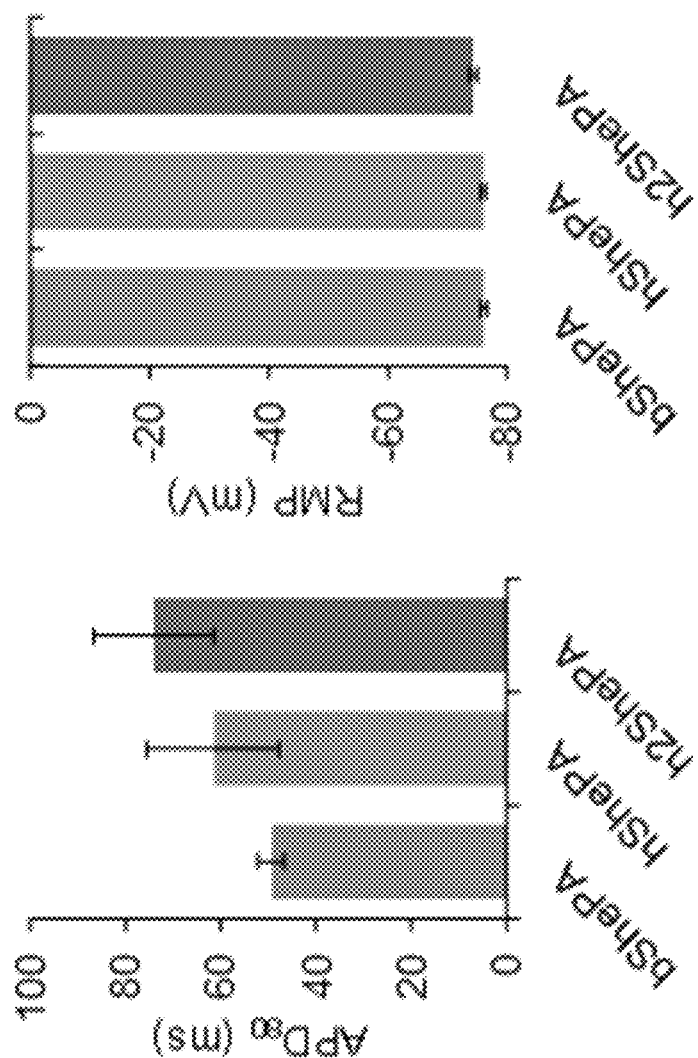

Since NavSheP D60A and EGFP genes are linked via the T2A peptide in each lentiviral construct, any change in transcriptional and translational efficiencies of NavSheP D60A gene as a result of codon optimization is expected to effect change in EGFP expression level. Indeed, under similar functional titers, transduction of monoclonal HEK293 line expressing Kir2.1 with bShePA-EGFP virus yielded lower EGFP intensity compared to both optimized versions (hShePA-EGFP and h2ShePA-EGFP) (FIG. 1A), with ATUM optimized construct showing highest EGFP signal (FIG. 1B). Patch damp recordings revealed a similar trend for NavSheP D60A channel expression, with hShePA and h2ShePA exhibiting 3.3-fold and 5.4-fold increases in peak INa (−204±29 and −312±17 pA/pF) respectively, compared to non-optimized bShePA (−58±5 pA/pF). As a result, AP upstrokes were improved 2.5 and 3.8 times using hShePA (168±36 V/s) and h2ShePA (252±28 V/s) respectively, compared to bShePA (66±10 V/s) (FIG. 1C). As NavSheP D60A channel contributes to the main depolarizing current during the plateau phase of AP, an increasing trend in AP duration was observed with higher INa, albeit without any statistically significant difference (FIG. 1D, FIG. 1E). Resting membrane potential also remained stable across all three groups (FIG. 1F). These results demonstrated significant improvement in expression level of NavSheP D60A channels via codon optimization, particularly using ATUM algorithm.

Example 3

Improvement of BacNav Channel Trafficking

Figures 2A, 2B, 2C, 2D:
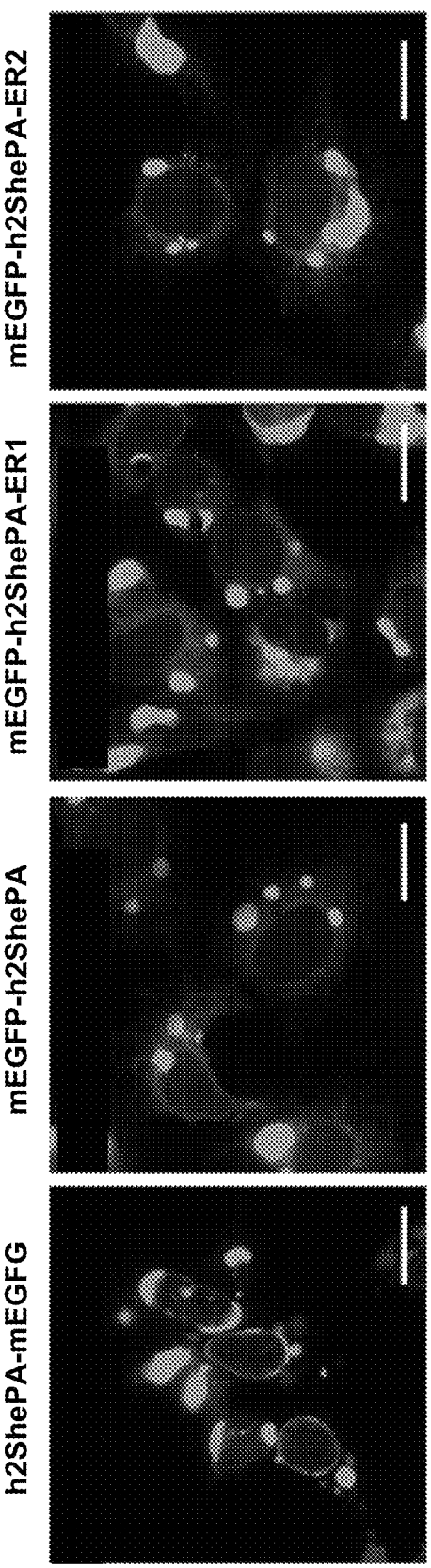

In order to evaluate membrane trafficking of NavSheP D60A, we fused the channel to either the carboxyl or amino terminus of mEGFP. Fusion of mEGFP to channel's C-terminus (h2ShePA-mEGFP) resulted in primarily perinuclear labeling (FIG. 2A). Since the C-terminal domain of BacNav plays roles in channel assembly and stability of the tetrameric structure, the addition of fluorescence reporter at the C-terminal domain may hinder these processes. In contrast, mEGFP fused at the N-terminus of NavSheP D60A (mEGFP-h2ShePA) showed significantly improved channel spatial distribution; however, large intracellular aggregations were observed throughout the cell (FIG. 2B). Moreover, GFP pattern resembled the endoplasmic reticulum (ER) structure, suggesting that export from the ER could be the limiting step of NavSheP D60A trafficking. In order to minimize intracellular aggregation and improve ER export of these channels, we added to their carboxyl terminus short amino acid motifs that regulate export of Kv1.4, Kv1.5, and Kir2.1 (named ER1, ER2, ER3, respectively). We observed no improvement when ER1 and ER2 were present (FIG. 2C and FIG. 2D). However, the addition of ER3 significantly enhanced membrane labeling and minimized intracellular aggregation of the channels (FIG. 2E). The position of ER3 also appeared to be affect expression, since addition of this motif to the N-terminus of the fusion protein failed to show any improvement (FIG. 2F). Importantly, enhanced membrane trafficking in the presence of ER3 motif resulted in higher current density (FIG. 2G) and improved upstroke velocity (FIG. 2H).

Figure 3K:
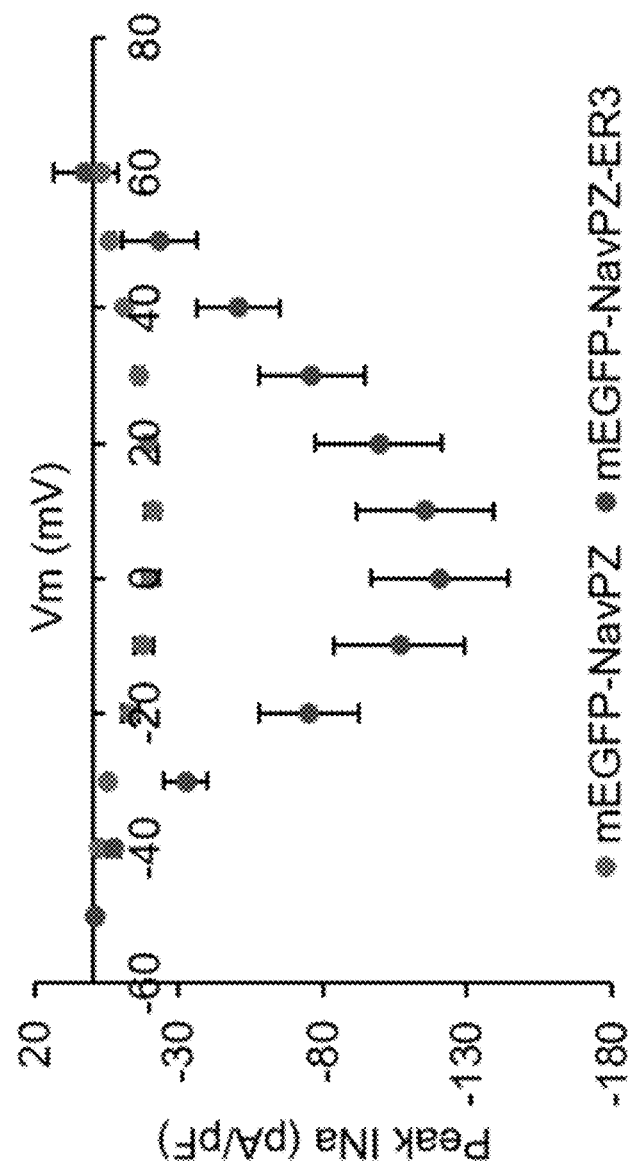

In order to assess membrane trafficking of other BacNav orthologs, we fused their genes to the C-terminus of mEGFP (FIG. 3A-FIG. 3E). Similar to NavSheP, large intracellular aggregates were observed for NavBacL and NaChBac (FIG. 3A and FIG. 3B). Notably, for NavMs, aggregates were located primarily around cell nucleus (FIG. 3C), suggesting that small current density typically observed for NavMs-expressing cells during patch clamp recordings (data not shown) could be attributed to impaired channel trafficking. On the other hand, mEGFP-NavPz and mEGFP-NavSilP displayed virtually no intracellular aggregates; however, GFP pattern still resembled the ER structure with poor membrane labeling (FIG. 3D and FIG. 3E). Importantly, we showed that addition of the ER3 motif to the C-termini of all tested channels significantly improved their membrane trafficking (FIG. 3F-FIG. 3J). Patch clamp recordings further showed significant increase in current density from NavPZ in the presence of ER3, suggesting this motif enhanced membrane channel density even for BacNav isoforms with minimal intracellular aggregation (FIG. 3K). One exception was NavMs, which still showed notable perinuclear labeling, suggesting that impaired trafficking of this ortholog could be attributed to other processes besides ER export. Further improvement in NavMs trafficking could benefit from the addition of other motifs such as the Golgi export motifs (Bonifacino, J. S. & Traub, L. M. *Annu Rev Biochem* 2003, 72, 395-447) or trafficking signals (Hofherr, A., et al. *J Cell Sci* 2005, 118, 1935-1943). Nevertheless, these results demonstrated that enhancement in trafficking of BacNav orthologs to the plasma membrane could be achieved via the simple addition of a short amino acid sequence, presenting yet another method to boost BacNav current in mammalian expression system.

Example 4

Direct Expression of BacNav in Healthy and Fibrotic NRVM Cultures

Figure 4A:
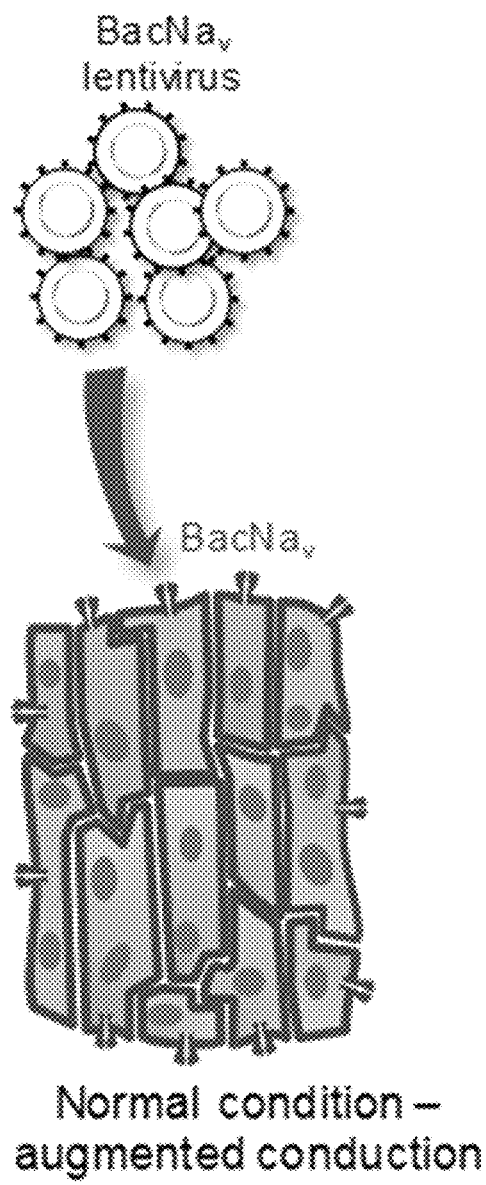
Figure 4C:
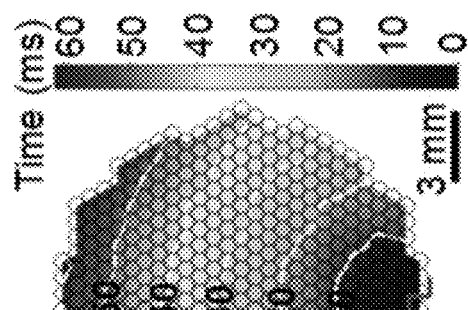
Figure 4B:
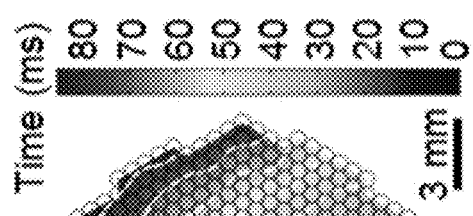
Figure 4E:
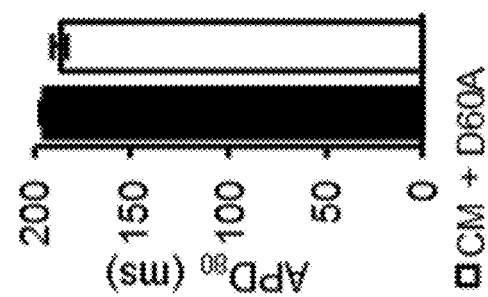
Figure 4D:
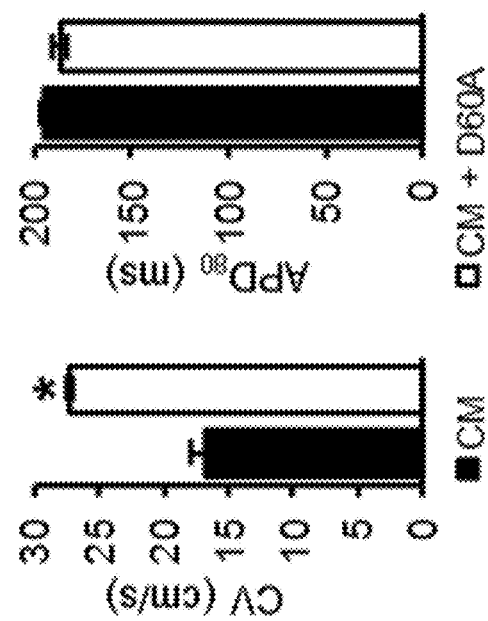

To examine the effects of BacNav in cardiomyocytes, we transduced monolayers of neonatal rat ventricular myocytes with NavSheP D60A lentivirus with expectation that under normal conditions, expression of BacNav in cardiomyocytes could enhance tissue excitability and improve conduction velocity (FIG. 4A). In fact, optical mapping results revealed that expression of NavSheP D60A significantly augmented conduction velocity of healthy NRVM cultures from 15.9±0.8 cm/s to 26.1±0.7 cm/s (FIG. 4B-FIG. 4D) without notable change in AP duration (FIG. 4E). We further assessed the effects of expressing NavSheP D60A in cardiomyocytes using a Luo-Rudy model (Luo, C. H. & Rudy, Y. *Circ Res* 1991, 68, 1501-1526) adapted to simulate CV and APD in neonatal rat ventricular myocyte monolayers. Simulation results showed gradual increase in CV with addition of more NavSheP D60A channels (FIG. 4F). The $\overline{G}_{Na}$ value needed to improve CV of the cardiac model to the same level shown in our mapping results was 281 nS (FIG. 4G), which also induced only a slight decrease in APD80 (FIG. 4H) and demonstrates a good match between simulated and experimental results.

Figure 5H:
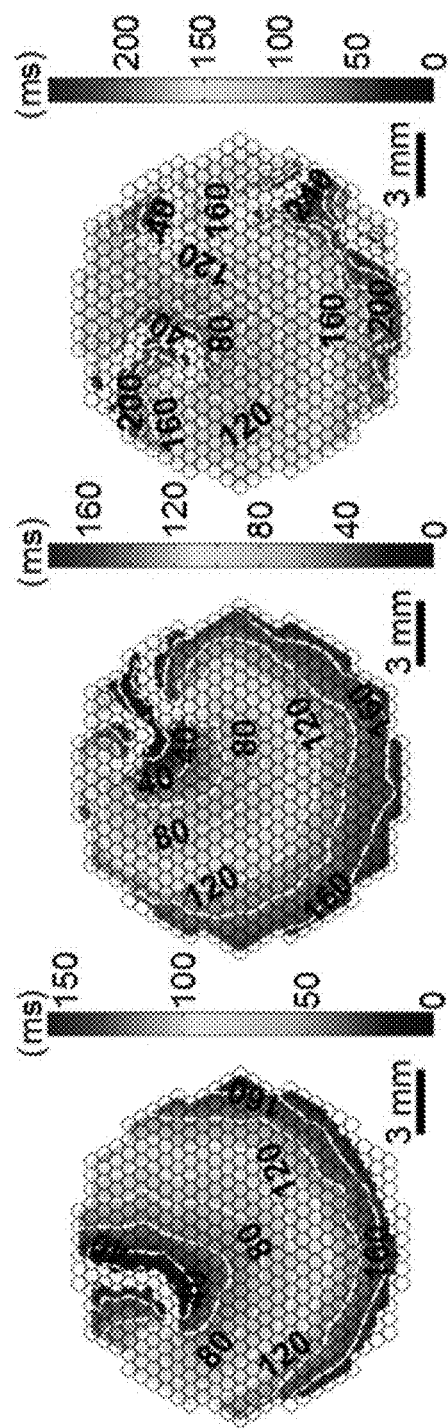
Figure 5I:
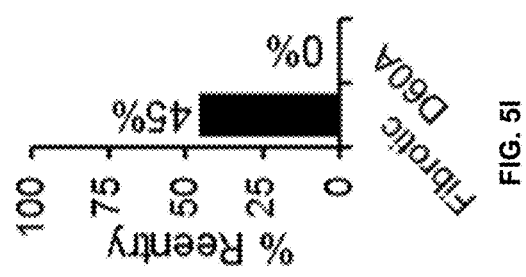

High fibroblast content in cardiomyocyte cultures has been shown to significantly slow down conduction and increase incidence of reentry. Thus, we next examined whether BacNav expression could improve conduction and prevent reentrant activity in fibrosis-mimetic cardiac cultures. Transduction with NavSheP D60A-EGFP lentivirus resulted in robust GFP expression throughout the co-culture (FIG. 5B), but not in the untransduced group (FIG. 5A). Expression of the prokaryotic sodium channels increased conduction velocity from 13.1±0.5 cm/s (FIG. 5C and FIG. 5E) in fibrotic control to 19.9±1.6 cm/s (FIG. 5D and FIG. 5E). Furthermore, transduced cultures exhibited higher maximum capture rate (5.6±0.6 Hz) compared to untransduced controls (4.5±0.2 Hz; FIG. 5F). Similar to mapping in non-fibrotic NRVM monolayers, no change in APD80 was observed with the expression of NavSheP D60A (FIG. 5G). Importantly, while 45% of tested untransduced fibrotic monolayers displayed spontaneous or induced reentrant activity, no reentries were observed in NavSheP D60A transduced monolayers (FIG. 5H and FIG. 5I). Taken together, these results demonstrated that expression of NavSheP D60A channels can improve conduction velocity and decrease incidence of arrhythmias in cardiomyocyte-fibroblast co-cultures.

Example 5

Immunomodulatory Effect of Engineered Fibroblasts

Figure 6:
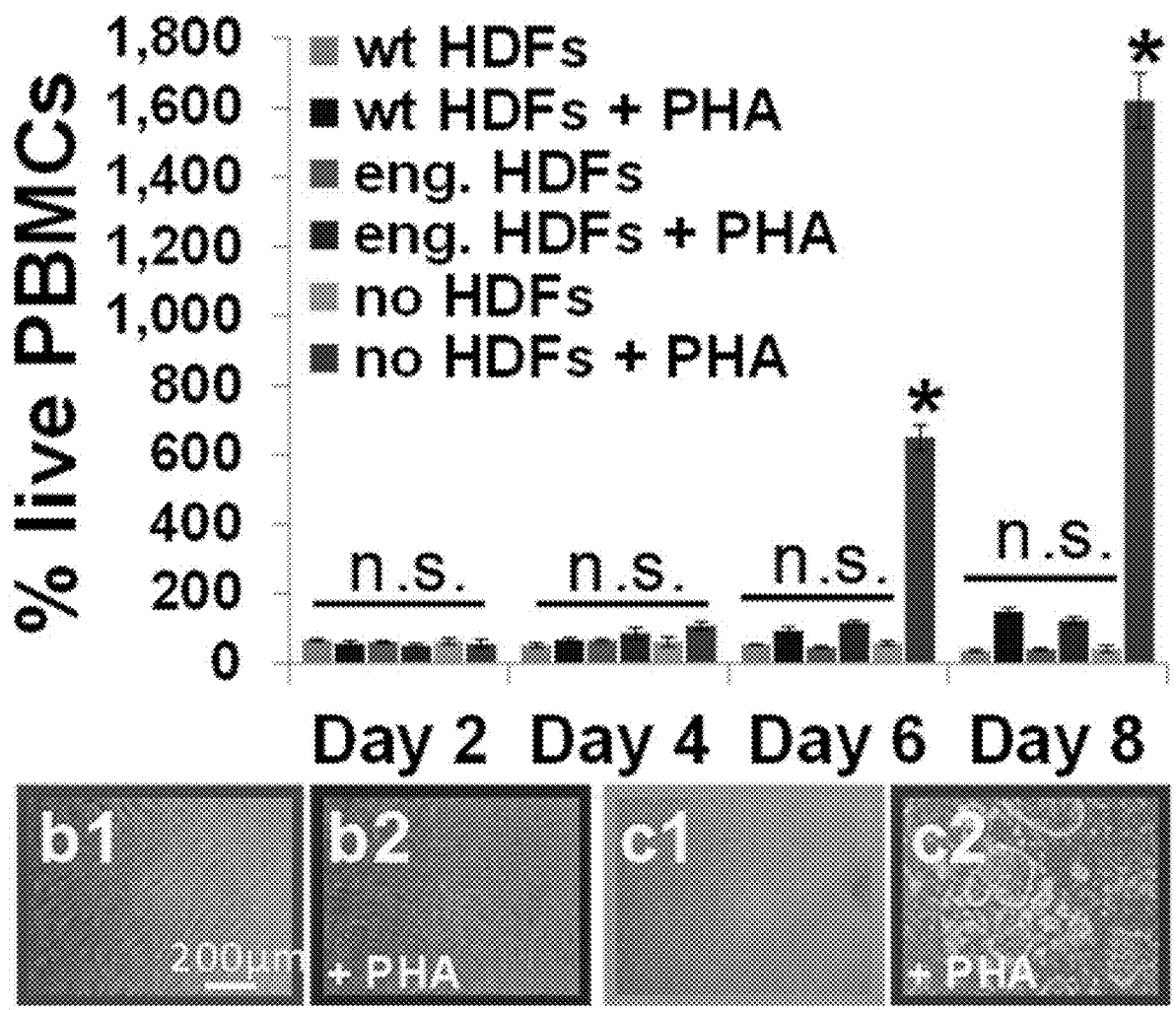
FIG. 6. Immunoreactivity of human PBMCs co-cultured with HDFs. PBMC proliferation during coculture with wild-type (wt) HDFs, engineered (eng.) HDFs, or no HDFs, with or without 10 µg/mL PHA stimulation. n=4-7; *$p<0.001$. Representative images of PBMCs 8 days after culture with engineered HDFs (b1-b2) or alone (no HDFs, c1-c2) without (b1,c1) or with (b2,c2) PHA.

Since the engineered fibroblasts express prokaryotic sodium channels, we assessed their potential immunomodulatory effects using an in vitro allogeneic lymphocyte proliferation assay (Quah, B. J., et al. *Nature Protocols* 2007, 2, 2049-2056). Engineered or wild-type human dermal fibroblasts (HDFs) were co-cultured for 8 days with human peripheral blood mononuclear cells (PBMCs). PBMC proliferation was quantified as indicative of innate immunoreactivity. Phytohemagglutinin (PHA), a known PBMC mitogen, was administered as a positive control. We found that none of the engineered HDFs activated PBMC proliferation (FIG. 6). Furthermore, wild-type and engineered HDFs were found to be immunosuppressive and inhibited stimulated PBMC proliferation much like human foreskin fibroblasts and mesenchymal stem cells.

Example 6

Animal Studies

In vivo function of the vectors is demonstrated via the epicardial gene painting method in large animals (pigs). Poloxamer/trypsin solution is made by adding trypsin from bovine pancreas to phosphate-buffered saline (PBS) at 1% (wt/vol) chilling to 4° C., and mixing with poloxamer 407 at 40% (wt/vol) for 16-24 hours until poloxamer completely dissolved into the solution. Immediately before use, AAV vector (e.g. serotypes 1, 6, 8, 9) is mixed with the poloxamer/trypsin solution at a 1:1 ratio to form the gel painting mixture containing AAV, 20% poloxamer (wt/vol), and 0.5% trypsin (wt/vol).

Healthy pigs and those undergoing chronical atrial fibrillation are sedated with ketamine (30 mg/kg) and anesthetized with sodium thiopental (2 to 5 mL of 5% solution). Anesthesia is maintained with 1% to 2% isoflurane. After sterile preparation, the chest is opened by median sternotomy. The pericardium is incised to expose both atria. The pleurae remain intact, and the lung fields are never exposed. The AAV-gel mixture is painted onto the atria with a round-bristle, flat paintbrush composed of camel hair. The heart is manipulated to expose all epicardial surfaces of the atria. The 5-mL total painting mixture is divided in half, so each atrium receives 2.5 mL of solution. Each atrium is coated twice for 60 seconds each time, with approximately 5 minutes elapsed between painting coats to facilitate adsorption. After being painted, the atria are left exposed to air for 10 minutes to enable virus penetration, after which chest is closed. Alternatively, AAV solution in PBS is delivered via multiple injections in the endocardium of the atrial or ventricular wall using an injection catheter. After surgery, pain is managed with narcotics and nonsteroidal anti-inflammatory medications as needed. Postoperative monitoring includes 30 seconds of 6-lead ECG recordings daily for 15-45 days, as well as daily assessment of behavior and feeding habits. In some animals, ECG telemetric monitoring is used for chronic recording of electrical activity in the heart. At the end of the experiments, hearts are excised, mounted on Langendorff apparatus, stained with voltage sensitive dye and assessed for action potential shape and propagation using optical mapping with CCD or CMOS cameras. Vulnerability to arrhythmia induction is studied using standard programmed electrical stimulation protocols.

The animals are maintained in accordance with the guiding principles of the American Physiological Society regarding experimental animals.

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1. A method of treating a voltage gated ion channel-related condition in a subject, the method comprising administering to the subject a recombinant AAV9 vector encoding a BacNav prokaryotic ion channel polypeptide, wherein the BacNav prokaryotic ion channel polypeptide is expressed in the cardiomyocytes of the subject, and wherein the voltage gated ion channel-related condition is selected from heart arrhythmia, chronic atrial fibrillation, damage from myocardial infarction, damage from stroke, and chronic ischemia.

Clause 2. A method of increasing the conductivity of a cardiac tissue of a subject, the method comprising administering to the subject a recombinant AAV9 vector encoding a BacNav prokaryotic ion channel polypeptide, wherein the BacNav prokaryotic ion channel polypeptide is expressed in the cardiomyocytes of the subject.

Clause 3. A method of increasing the resistance to conduction block of a cardiac tissue of a subject, the method comprising administering to the subject a recombinant AAV9 vector encoding a BacNav prokaryotic ion channel polypeptide, wherein the BacNav prokaryotic ion channel polypeptide is expressed in the cardiomyocytes of the subject.

Clause 4. A method of increasing the upstroke velocity of a cardiac tissue of a subject, the method comprising administering to the subject a recombinant AAV9 vector encoding a BacNav prokaryotic ion channel polypeptide, wherein the BacNav prokaryotic ion channel polypeptide is expressed in the cardiomyocytes of the subject.

Clause 5. The method of any one of the previous clauses, wherein the BacNav prokaryotic ion channel polypeptide comprises an amino acid sequence selected from SEQ ID NO: 23 or a variant thereof, or SEQ ID NO: 24 or a variant thereof.

Clause 6. The method of any one clauses 1-4, wherein the BacNav prokaryotic ion channel polypeptide comprises an amino acid sequence encoded by a polynucleotide sequence selected from SEQ ID NO: 1, SEQ ID NO: 2, and SEQ ID NO: 3.

Clause 7. The method of any one of clauses 1-4, wherein the BacNav prokaryotic ion channel polypeptide comprises a motif having an amino acid sequence of SEQ ID NO: 4 (GVKESL), SEQ ID NO: 5 (DLRRSL), or SEQ ID NO: 6 (FCYENEV), or a combination thereof.

Clause 8. The method of clause 7, wherein the motif is positioned at the C-terminal end of the BacNav prokaryotic ion channel polypeptide.

Clause 9. The method of any one of clauses 1-4, wherein the vector comprises a polynucleotide sequence of SEQ ID NO: 25.

Clause 10. The method of any one of the previous clauses, wherein the vector is administered to the subject in a pharmaceutical composition comprising the vector and a pharmaceutically acceptable carrier.

Clause 11. The method of any one of the previous clauses, wherein the vector is administered to a coronary artery or a coronary sinus of the subject.

Clause 12. The method of any one of clauses 1-11, wherein the vector is administered to the subject sublingually, orally, intranasally, intravenously, parenterally, subcutaneously, intramuscularly, intraperitoneally, rectally, intravaginally, or intrathecally.

Clause 13. The method of any one of clauses 1-4, 7-8, and 10-12, wherein the BacNav prokaryotic ion channel polypeptide is a sodium channel, a calcium channel, or a combination thereof.

Clause 14. The method of any one of clauses 1-13, wherein the BacNav prokaryotic ion channel polypeptide is a sodium channel.

Clause 15. The method of any one of clauses 1-14, wherein the prokaryotic ion channel polypeptide has reduced immunogenicity relative to a control.

Clause 16. The method of any one of clauses 1-14, wherein the prokaryotic ion channel polypeptide has reduced antigenicity relative to a control.

Clause 17. The method of any one of clauses 1-14, wherein the prokaryotic ion channel polypeptide is immunosuppressive.

Clause 18. The method of any one of clauses 1-14, wherein the cardiomyocyte expressing the prokaryotic ion channel polypeptide has reduced immunogenicity relative to a control.

Clause 19. The method of any one of clauses 1-14, wherein the cardiomyocyte expressing the prokaryotic ion channel polypeptide has reduced antigenicity relative to a control.

Clause 20. The method of any one of clauses 1-14, wherein the cardiomyocyte expressing the prokaryotic ion channel polypeptide is immunosuppressive.

SEQUENCES

```
bShePA: SEQ ID NO: 1
BacNav polynucleotide
atgagtacatctttacttaacgcgccaacgggtttgcaggcacgagtgattaacttggttgagc
aaaactggtttggtcatttattttggcattgattttaatcaacgcggtgcagttaggtatgga
gacctcagccagcctgatggcgcaatacggtactttgttgatgagtcttgataagttgctactg
agtgtatttgtggtggagttattgctgcggatttatgcctacaggggaaattttttaaagacc
cttggagcgtgttcgattttaccgtgatagtgatagcactgatccctgcatctgggccattggc
tgtcctgcgttcgctcagggtattgcgggtgctgagagtgttaacaattgtgccatcaatgaaa
cgggtggtgtctgcgctgttgggatcacttcctggattggcatcgatcgccacggtattactgt
tgatttattatgtgtttgcggtgattgctaccaaaattttggcgatgcattccctgaatggtt
tggcactattgctgactcattttatacctatttcaaataatgacgcttgaaagctggtctatg
ggaatttcgcggccagtgatggaagtgtaccctatgcttgggtattttcgtaccatttattc
tggtagcgactttcacaatgctaaatttgtttattgcgattatcgtcaataccatgcaaaccttt
cagcgacgaagagcatgcattagagcgtgaacaagacaaacaaatcttagagcaggaacaaaga
caaatgcacgaggagttgaaagccatcagactcgagctacaacaattacaaaccttgttgcgca
atgctgctggtgattcttctaatgtgtcgacaaagggaaacattggttctgactga hShePA: SEQ ID NO: 2
BacNav polynucleotide, human codon optimized
atgtcaacctcactgctgaacgctccaactgggctgcaggcaagagtcatcaatctggtcgaac
agaactggtttgggcactttattctggcactgatcctgattaacgcagtgcagctgggaatgga
gaccagcgcctccctgatggcacagtacggaacactgctgatgtccctggcaaagctgctgctg
agcgtgttcgtggtcgaactgctgctgcgaatctacgcctatcggggcaagttctttaaagacc
cctggagcgtgttcgacttcaccgtgatcgtcattgccctgattccagctagtggacctctggc
cgtgctgcggtcactgagagtgctgagggtcctgcgcgtgctgacaatcgtgcctagcatgaag
agggtggtctcagctctgctgggcagcctgccaggactggcatccatcgctactgtgctgctgc
tgatctactatgtcttcgcagtgatcgccactaaaattttcggagacgcttttcccgagtggtt
cggcaccatcgcagattctttttatacactgttccagatcatgactctggagtcttggagtatg
ggcatcagtcgcccagtcatggaagtgtaccctatgcctgggtcttctttgtgccttttattc
tggtcgccaccttcacaatgctgaacctgtttatcgctatcattgtgaatactatgcagaccttt
tagcgacgaggaacacgctctggagcgagaacaggataagcagattctggagcaggaacagaga
cagatgcatgaggaactgaaagcaatcaggctggagctgcagcagctgcagacactgctgagaa
acgctgctggcgattcatcaaacgtgtccactaaaggaaacattggctctgactga h2ShePA: SEQ ID NO: 3
BacNav polynucleotide, human codon optimized
atgtcaacctcccttctgaacgcccccaccggtctgcaagcccgcgtcatcaacctggtcgaac
agaactggttcggccacttcatcctcgcactgattctcattaacgccgtgcagcttggaatgga
aactagcgcgtccctgatggctcaatacggcacactgctcatgagcctggcgaagctgctcctg
tccgtgttcgtggtgaactgttgctgcggatctatgcgtaccgcggaaaattcttcaaggatc
catggagcgtgttcgactttactgtgattgtgatcgcactcatcccggcctcgggaccgctcgc
cgtgctccggtcactgagagtcctgagggtgctcagagtgctgaccattgtgcctagcatgaag
cgcgtggtgtccgccctgttgggatccctgccgggtttggcttcgattgccactgtgctgctcc
tgatctactacgtgttcgccgtcattgccactaagattttcggcgacgcctttcctgagtggtt
cggaaccatcgctgactctttctacaccttgttccaaatcatgaccctggaatcctggtccatg
gggatttcgaggcccgtgatggaggtgtaccctacgcctgggtgttcttcgtcccctcatcc
ttgtcgcaaccttcaccatgcttaacctgtttatcgccatcatcgtgaacacgatgcagaccttt
ctccgatgaagaacatgcgctggagcgggaacaggacaagcagatcctggagcaggaacagcgg
cagatgcacgaggagctgaaggccatccggctggagctgcagcagctccaaactctgctgcgca
acgcggccggagattcaagcaatgtgtcgaccaaggggaacatcggctccgactga
```

| SEQUENCES |
| --- |

SEQ ID NO: 4
ER Export Motif
(GVKESL)

SEQ ID NO: 5
ER Export Motif
(DLRRSL)

SEQ ID NO: 6
ER Export Motif
(FCYENEV)

SEQ ID NO: 7
LESWSM

SEQ ID NO: 8
LDDWSD

SEQ ID NO: 9
PDZ binding motif
SEI

SEQ ID NO: 10
PDZ binding motif
SIV

SEQ ID NO: 11
PDZ binding motif
TDV

SEQ ID NO: 12
Ankyrin-G binding motif
VPIAVAESD

SEQ ID NO: 13
Golgi export motif
RSFVKKDGHCNVQFINV

SEQ ID NO: 14
Membrane trafficking motif
KSRITSEGEYIPLDQIDINV

SEQ ID NO: 15
Peptide linker
$(G)_n$ wherein n is an integer from 1 to 10

SEQ ID NO: 16
Peptide linker
$(GGGGS)_n$ wherein n is an integer from 1 to 10

SEQ ID NO: 17
Peptide linker
$(EAAAK)_n$ wherein n is an integer from 1 to 10

SEQ ID NO: 18
Peptide linker
$(XP)_n$ wherein n is an integer from 1 to 10 and X is any amino acid SEQ ID NO: 19
Polynucleotide encoding ER export motif of SEQ ID NO: 6
ttctgctacgagaacgaggtg SEQ ID NO: 20
BacNav polynucleotide with ER export motif
atgagtacatctttacttaacgcgccaacgggtttgcaggcacgagtgattaacttggttgagc
aaaactggtttggtcattttattttggcattgattttaatcaacgcggtgcagttaggtatgga
gacctcagccagcctgatggcgcaatacggtactttgttgatgagtcttgataagttgctactg
agtgtatttgtggtggagttattgctgcggatttatgcctacaggggaaatttttaaagacc
cttggagcgtgttcgattttaccgtgatagtgatagcactgatccctgcatctgggccattggc
tgtcctgcgttcgctcagggtattgcgggtgctgagagtgttaacaattgtgccatcaatgaaa
cgggtggtgtctgcgctgttgggatcacttcctggattggcatcgatcgccacggtattactgt
tgatttattatgtgtttgcggtgattgctaccaaaatttttggcgatgcattccctgaatggtt
tggcactattgctgactcattttataccctatttcaaataatgacgcttgaaagctggtctatg
ggaatttcgcggccagtgatggaagtgtacccttatgcttgggtatttttcgtaccatttattc
tggtagcgactttcacaatgctaaatttgtttattgcgattatcgtcaataccatgcaaacctt
cagcgacgaagagcatgcattagagcgtgaacaagacaaacaaatcttagagcaggaacaaaga

| SEQUENCES |
|---|
| caaatgcacgaggagttgaaagccatcagactcgagctacaacaattacaaaccttgttgcgca atgctgctggtgattcttctaatgtgtcgacaaagggaaacattggttctgacttctgctacga gaacgaggtgtga |

SEQ ID NO: 21
BacNav polynucleotide with ER export motif, human codon optimized
atgtcaacctcactgctgaacgctccaactgggctgcaggcaagagtcatcaatctggtcgaac
agaactggtttgggcactttattctggcactgatcctgattaacgcagtgcagctgggaatgga
gaccagcgcctccctgatggcacagtacggaacactgctgatgtccctggcaaagctgctgctg
agcgtgttcgtggtcgaactgctgctgcgaatctacgcctatcggggcaagttctttaaagacc
cctggagcgtgttcgacttcaccgtgatcgtcattgccctgattccagctagtggacctctggc
cgtgctgcggtcactgagagtgctgagggtcctgcgcgtgctgacaatcgtgcctagcatgaag
agggtggtctcagctctgctgggcagcctgccaggactggcatccatcgctactgtgctgctgc
tgatctactatgtcttcgcagtgatcgccactaaaattttcggagacgcttttcccgagtggtt
cggcaccatcgcagattcttttatacactgttccagatcatgactctggagtcttggagtatg
ggcatcagtcgcccagtcatggaagtgtacccctatgcctgggtcttctttgtgcctttttattc
tggtcgccaccttcacaatgctgaacctgtttatcgctatcattgtgaatactatgcagacctt
tagcgacgaggaacacgctctggagcgagaacaggataagcagattctggagcaggaacagaga
cagatgcatgaggaactgaaagcaatcaggctggagctgcagcagctgcagacactgctgagaa
acgctgctggcgattcatcaaacgtgtccactaaaggaaacattggctctgacttctgctacga
gaacgaggtgtga SEQ ID NO: 22
BacNav polynucleotide with ER export motif, human codon optimized
atgtcaacctcccttctgaacgcccccaccggtctgcaagcccgcgtcatcaacctggtcgaac
agaactggttcggccacttcatcctcgcactgattctcattaacgccgtgcagcttggaatgga
aactagcgcgtccctgatggctcaatacggcacactgctcatgagcctggcgaagctgctcctg
tccgtgttcgtggtggaactgttgctgcggatctatgcgtaccgcggaaaattcttcaaggatc
catggagcgtgttcgactttactgtgattgtgatcgcactcatcccggcctcgggaccgctcgc
cgtgctccggtcactgagagtcctgagggtgctcagagtgctgaccattgtgcctagcatgaag
cgcgtggtgtccgccctgttgggatccctgccgggtttggcttcgattgccactgtgctgctcc
tgatctactacgtgttcgccgtcattgccactaagattttcggcgacgcctttcctgagtggtt
cggaaccatcgctgactctttctacaccttgttccaaatcatgaccctggaatcctggtccatg
gggatttcgaggcccgtgatggaggtgtacccttacgcctgggtgttcttcgtccccttcatcc
ttgtcgcaaccttcaccatgcttaacctgtttatcgccatcatcgtgaacacgatgcagacctt
ctccgatgaagaacatgcgctggagcgggaacaggacaagcagatcctggagcaggaacagcgg
cagatgcacgaggagctgaaggccatccggctggagctgcagcagctccaaactctgctgcgca
acgcggccggagattcaagcaatgtgtcgaccaaggggaacatcggctccgacttctgctacga
gaacgaggtgtga SEQ ID NO: 23
Wild-type polypeptide sequence of BacNav ion channel from *Shewanella putrefaciens*.
STSLLNAPTGLQARVINLVEQNWFGHFILALILINAVQLGMETSASLMAQYGTLLMSLAKLLLS
VFVVELLLRIYAYRGKFFKDPWSVFDFTVIVIALIPASGPLAVLRSLRVLRVLRVLTIVPSMKR
VVSALLGSLPGLASIATVLLLIYYVFAVIATKIFGDAFPEWFGTIADSFYTLFQIMTLESWSMG
ISRPVMEVYPYAWVFFVPFILVATFTMLNLFIAIIVNTMQTFSDEEHALEREQDKQILEQEQRQ
MHEELKAIRLELQQLQTLLRNAAGDSSNVSTKGNIGSD SEQ ID NO: 24
Wild-type polypeptide sequence of BacNav ion channel from *Shewanella putrefaciens* with ER export motif.
STSLLNAPTGLQARVINLVEQNWFGHFILALILINAVQLGMETSASLMAQYGTLLMSLAKLLLS
VFVVELLLRIYAYRGKFFKDPWSVFDFTVIVIALIPASGPLAVLRSLRVLRVLRVLTIVPSMKR
VVSALLGSLPGLASIATVLLLIYYVFAVIATKIFGDAFPEWFGTIADSFYTLFQIMTLESWSMG
ISRPVMEVYPYAWVFFVPFILVATFTMLNLFIAIIVNTMQTFSDEEHALEREQDKQILEQEQRQ
MHEELKAIRLELQQLQTLLRNAAGDSSNVSTKGNIGSDFCYENEV

SEQ ID NO: 25
Polynucleotide; lentiviral vector encoding wild-type BacNav ion channel from *Shewanella putrefaciens*, GFP, CMV promotor.
agcttaatgtagtcttatgcaatactcttgtagtcttgcaacatggtaacgatgagttagcaac
atgccttacaaggagagaaaaagcaccgtgcatgccgattggtggaagtaaggtggtacgatcg
tgccttattaggaaggcaacagacgggtctgacatggattggacgaaccactgaattgccgcat
tgcagagatattgtatttaagtgcctagctcgatacaataaacgggtctctctggttagaccag
atctgagcctgggagctctctggctaactagggaacccactgcttaagcctcaataaagcttgc
cttgagtgcttcaagtagtgtgtgcccgtctgttgtgtgactctggtaactagagatccctcag
acccttttagtcagtgtggaaaatctctagcagtggcgcccgaacagggacctgaaagcgaaag
ggaaaccagagctctctcgacgcaggactcggcttgctgaagcgcgcacggcaagaggcgaggg
gcggcgactggtgagtacgccaaaaattttgactagcggaggctagaaggagagagatgggtgc
gagagcgtcagtattaagcgggggagaattagatcgcgatgggaaaaaattcggttaaggccag
ggggaaagaaaaaatataaattaaaacatatagtatgggcaagcagggagctagaacgattcgc
agttaatcctggcctgttagaaacatcagaaggctgtagacaaatactgggacagctacaacca
tcccttcagacaggatcagaagaacttagatcattatataatacagtagcaaccctctattgtg
tgcatcaaaggatagagataaaagacaccaaggaagctttagacaagatagaggaagagcaaaa
caaaagtaagaccaccgcacagcaagcggccgctgatcttcagacctggaggaggagatatgag
ggacaattggagaagtgaattatataaatataaagtagtaaaaattgaaccattaggagtagca -continued

| SEQUENCES |
|---|
| cccaccaaggcaaagagaagagtggtgcagagagaaaaaagagcagtgggaataggagctttgt |
| tccttgggttcttgggagcagcaggaagcactatgggcgcagcctcaatgacgctgacggtaca |
| ggccagacaattattgtctggtatagtgcagcagcagaacaatttgctgagggctattgaggcg |
| caacagcatctgttgcaactcacagtctggggcatcaagcagctccaggcaagaatcctggctg |
| tggaaagatacctaaaggatcaacagctcctggggatttggggttgctctggaaaactcatttg |
| caccactgctgtgccttggaatgctagttggagtaataaatctctggaacagatttggaatcac |
| acgacctggatggagtgggacagagaaattaacaattacacaagcttaatacactccttaattg |
| aagaatcgcaaaaccagcaagaaaagaatgaacaagaattattggaattagataaatgggcaag |
| tttgtggaattggtttaacataacaaattggctgtggtatataaaattattcataatgatagta |
| ggaggcttggtaggtttaagaatagtttttgctgtactttctatagtgaatagagttaggcagg |
| gatattcaccattatcgtttcagacccacctcccaacccgaggggacccgacaggcccgaagg |
| aatagaagaaggtggagagagacagagacagatccattcgattagtgaacggatctcga |
| cggtatcggttaacttttaaaagaaaaggggggattgggggtacagtgcagggggaaagaatag |
| tagacataatagcaacagacatacaaactaaagaattacaaaaacaaattacaaaaattcaaaa |
| ttttatcgataagcttgggagttccgcgttacataacttacggtaaatggcccgcctggctgac |
| cgccaacgaccccccgcccattgacgtcaataatgacgtatgttcccatagtaacgccaatagg |
| gactttccattgacgtcaatgggtggagtatttacggtaaactgcccacttggcagtacatcaa |
| gtgtatcatatgccaagtacgccccctattgacgtcaatgacggtaaatggcccgcctggcatt |
| atgcccagtacatgaccttatgggactttcctacttggcagtacatctacgtattagtcatcgc |
| tattaccatggtgatgcggttttggcagtacatcaatgggcgtggatagcggtttgactcacgg |
| ggatttccaagtctccaccccattgacgtcaatgggagtttgttttggcaccaaaatcaacggg |
| actttccaaaatgtcgtaacaactccgccccattgacgcaaatgggcggtaggcgtgtacggtg |
| ggaggtctatataagcagagctcgtttagtgaaccgtcagatcgcctggagacgccatccacgc |
| tgttttgacctccatagaagacaccgactctagtaatacgactcactataggctagcgccacca |
| tgagtacatctttacttaacgcgccaacgggtttgcaggcacgagtgattaacttggttgagca |
| aaactggtttggtcattttattttggcattgattttaatcaacgcggtgcagttaggtatggag |
| acctcagccagcctgatggcgcaatacggtactttgttgatgagtcttgataagttgctactga |
| gtgtatttgtggtggagttattgctgcggatttatgcctacaggggggaaattttttaaagaccc |
| ttggagcgtgttcgattttaccgtgatagtgatagcactgatccctgcatctgggccattggct |
| gtcctgcgttcgctcagggtattgcgggtgctgagagtgttaacaattgtgccatcaatgaaac |
| gggtggtgtctgcgctgtgggatcacttcctggattggcatcgatcgccacggtattactgtt |
| gatttattatgtgtttgcggtgattgctaccaaaattttttggcgatgcattccctgaatggttt |
| ggcactattgctgactcattttataccctatttcaaataatgacgcttgaaagctggtctatgg |
| gaatttcgcggccagtgatggaagtgtacccttatgcttgggtattttcgtaccatttattct |
| ggtagcgactttcacaatgctaaatttgtttattgcgattatcgtcaataccatgcaaaccttc |
| agcgacgaagagcatgcattagagcgtgaacaagacaaacaaatcttagagcaggaacaaagac |
| aaatgcacgaggagttgaaagccatcagactcgagctacaacaattacaaaccttgttgcgcaa |
| tgctgctggtgattcttctaatgtgtcgacaaagggaaacattggttctgacgaattcgagggc |
| agaggaagtcttctaacatgcggtgacgtggaggagaatcccggccctaccacaaccatggtga |
| gcaagggcgaggagctgttcaccggggtggtgcccatcctggtcgagctggacggcgacgtaaa |
| cggccacaagttcagcgtgtccggcgagggcgagggcgatgccaccctacggcaagctgaccctg |
| aagttcatctgcaccaccggcaagctgcccgtgccctggcccaccctcgtgaccaccctgacct |
| acggcgtgcagtgcttcagccgctaccccgaccacatgaagcagcacgacttcttcaagtccgc |
| catgcccgaaggctacgtccaggagcgcaccatcttcttcaaggacgacggcaactacaagacc |
| cgcgccgaggtgaagttcgagggcgacaccctggtgaaccgcatcgagctgaagggcatcgact |
| tcaaggaggacggcaacatcctggggcacaagctggagtacaactacaacagccacaacgtcta |
| tatcatggccgacaagcagaagaacggcatcaaggtgaacttcaagatccgccacaacatcgag |
| gacggcagcgtgcagctcgccgaccactaccagcagaacacccccatcggcgacggccccgtgc |
| tgctgcccgacaaccactacctgagcacccagtccgccctgagcaaagacccccaacgagaagcg |
| cgatcacatggtcctgctggagttcgtgaccgccgcgggatcactctcggcatggacgagctg |
| tacaagtagtctagacttaagccttaagaccaatgacttacaaggcagctgtagatcttagcc |
| acttttaaaagaaaaggggggactggaagggctaattcactcccaacgaagacaagatctgct |
| ttttgcttgtactgggtctctctggttagaccagatctgagcctgggagctctctggctaacta |
| gggaacccactgcttaagcctcaataaagcttgccttgagtgcttcaagtagtgtgtgcccgtc |
| tgttgtgtgactctggtaactagagatccctcagacccttttagtcagtgtggaaaatctctag |
| cagtagtagttcatgtcatcttattattcagtatttataacttgcaaagaaatgaatatcagag |
| agtgagaggaacttgtttattgcagcttataatggttacaaataaagcaatagcatcacaaatt |
| tcacaaataaagcatttttttcactgcattctagttgtggtttgtccaaactcatcaatgtatc |
| ttatcatgtctggctctagctatcccgcccctaactccgcccagttccgcccattctccgcccc |
| atggctgactaattttttttatttatgcagaggccgaggccgcctcggcctctgagctattcca |
| gaagtagtgaggaggcttttttggaggcctaggcttttgcgtcgagacgtaccccaattcgccct |
| atagtgagtcgtattacgcgcgctcactggccgtcgttttacaacgtcgtgactgggaaaaccc |
| tggcgttacccaacttaatcgccttgcagcacatccccctttcgccagctggcgtaatagcgaa |
| gaggcccgcaccgatcgcccttcccaacagttgcgcagcctgaatggcgaatggcgcgacgcgc |
| cctgtagcggcgcattaagcgcggcgggtgtggtggttacgcgcagcgtgaccgctacacttgc |
| cagcgccctagcgcccgctcctttcgctttcttcccttcctttctcgccacgttcgccggcttt |
| ccccgtcaagctctaaatcgggggctccctttagggttccgatttagtgctttacggcacctcg |
| accccaaaaaacttgattagggtgatggttcacgtagtgggccatcgccctgatagacggtttt |
| tcgccctttgacgttggagtccacgttctttaatagtggactcttgttccaaactggaacaaca |
| ctcaaccctatctcggtctattcttttgatttataagggattttgccgatttcggcctattggt |
| taaaaaatgagctgatttaacaaaaatttaacgcgaattttaacaaaatattaacgtttacaat |
| ttcccaggtggcacttttcggggaaatgtgcgcggaacccctatttgtttatttttctaaatac |
| attcaaatatgtatccgctcatgagacaataaccctgataaatgcttcaataatattgaaaaag |
| gaagagtatgagtattcaacatttccgtgtcgcccttattcccttttttgcggcatttttgcctt |
| cctgtttttgctcacccagaaacgctggtgaaagtaaaagatgctgaagatcagttgggtgcac |
| gagtgggttacatcgaactggatctcaacagcggtaagatccttgagagttttcgccccgaaga |
| acgttttccaatgatgagcacttttaaagttctgctatgtggcgcggtattatcccgtattgac |

SEQUENCES

```
gccgggcaagagcaactcggtcgccgcatacactattctcagaatgacttggttgagtactcac
cagtcacagaaaagcatcttacggatggcatgacagtaagagaattatgcagtgctgccataac
catgagtgataacactgcggccaacttacttctgacaacagtcgaggaccgaaggagctaacc
gcttttttgcacaacatggggatcatgtaactcgccttgatcgttgggaaccggagctgaatg
aagccataccaaacgacgagcgtgacaccacgatgcctgtagcaatggcaacaacgttgcgcaa
actattaactggcgaactacttactctagcttcccggcaacaattaatagactggatggaggcg
gataaagttgcaggaccacttctgcgctcggcccttccggctggctggtttattgctgataaat
ctggagccggtgagcgtgggtctcgcggtatcattgcagcactgggcaggatggtaagccctc
ccgtatcgtagttatctacacgacggggagtcaggcaactatggatgaacgaaatagacagatc
gctgagataggtgcctcactgattaagcattggtaactgtcagaccaagtttactcatatatac
tttagattgatttaaaacttcattttaatttaaaaggatctaggtgaagatccttttttgataa
tctcatgaccaaaatcccttaacgtgagttttcgttccactgagcgtcagaccccgtagaaaag
atcaaaggatcttcttgagatcctttttttctgcgcgtaatctgctgcttgcaaacaaaaaaac
caccgctaccagcggtggtttgtttgccggatcaagagctaccaactcttttccgaaggtaac
tggcttcagcagagcgcagataccaaatactgtccttctagtgtagccgtagttaggccaccac
ttcaagaactctgtagcaccgcctacatacctcgctctgctaatcctgttaccagtggctgctg
ccagtggcgataagtcgtgtcttaccgggttggactcaagacgatagttaccggataaggcgca
gcggtcgggctgaacggggggttcgtgcacacagcccagcttggagcgaacgacctacaccgaa
ctgagatacctacagcgtgagctatgagaaagcgccacgcttcccgaagggagaaaggcggaca
ggtatccggtaagcggcagggtcggaacaggagagcgcacgagggagcttccaggggaaacgc
ctggtatctttatagtcctgtcgggtttcgccacctctgacttgagcgtcgattttgtgatgc
tcgtcagggggcggagcctatggaaaaacgccagcaacgcggccttttacggttcctggcct
tttgctggccttttgctcacatgttctttcctgcgttatccctgattctgtggataaccgtat
taccgcctttgagtgagctgataccgctcgccgcagccgagcgagcgagcgagtcagtg
agcgaggaagcggaagagcgcccaatacgcaaaccgcctctccccgcgcgttggccgattcatt
aatgcagctggcacgacaggtttcccgactggaaagcgggcagtgagcgcaacgcaattaatgt
gagttagctcactcattaggcaccccaggctttacactttatgcttccggctcgtatgttgtgt
ggaattgtgagcggataacaatttcacacaggaaacagctatgaccatgattacgccaagcgcg
caattaaccctcactaaagggaacaaaagctggagctgca
```

SEQ ID NO: 26
connexin 43 (Cx43) polypeptide, *Homo sapiens*, Accession No. AAD37802, 382 amino acids

```
MGDWSALGKL LDKVQAYSTA GGKVWLSVLF IFRILLLGTA VESAWGDEQS
AFRCNTQQPG CENVCYDKSF PISHVRFWVL QIIFVSVPTL LYLAHVFYVM
RKEEKLNKKE EELKVAQTDG VNVDMHLKQI EIKKFKYGIE EHGKVKMRGG
LLRTYIISIL FKSIFEVAFL LIQWYIYGFS LSAVYTCKRD PCPHQVDCFL
SRPTEKTIFI IFMLVVSLVS LALNIIELFY VFFKGVKDRV KGKSDPYHAT
SGALSPAKDC GSQKYAYFNG CSSPTAPLSP MSPPGYKLVT GDRNNSSCRN
YNKQASEQNW ANYSAEQNRM GQAGSTISNS HAQPFDFPDD NQNSKKLAAG
HELQPLAIVD QRPSSRASSR ASSRPRPDDL EI
```

SEQ ID NO: 27
inwardly-rectifying potassium channel Kir2.1 polypeptide, *Homo sapiens*, Accession No. AAF73242, 427 amino acids

```
MGSVRTNRYS IVSSEEDGMK LATMAVANGF GNGKSKVHTR QQCRSRFVKK
DGHCNVQFIN VGEKGQRYLA DIFTTCVDIR WRWMLVIFCL APVLSWLFFG
CVFWLIALLH GDLDASKEGK ACVSEVNSFT AAFLFSIETQ TTIGYGFRCV
TDECPIAVFM VVFQSIVGCI IDAFIIGAVM AKMAKPKKRN ETLVFSHNAV
IAMRDGKLCL MWRVGNLRKS HLVEAHVRAQ LLKSRITSEG EYIPLDQIDI
NVGFDSGIDR IFLVSPITIV HEIDEDSPLY DLSKQDIDNA DFEIVVILEG
MVEATAMTTQ CRSSYLANEI LWGHRYEPVL FEEKHYYKVD YSRFHKTYEV
PNTPLCSARD LAEKKYILSN ANSFCYENEV ALTSKEEDDS ENGVPESTST
DTPPDIDLHN QASVPLEPRP LRRESEI
```

The invention claimed is:

1. A method of treating a voltage gated ion channel-related condition in a subject, the method comprising administering directly to the heart of the subject by injection a recombinant AAV9 vector encoding a BacNav prokaryotic ion channel polypeptide,
wherein the subject is a mammal,
wherein the vector comprises a promoter that directs expression of the BacNav prokaryotic ion channel polypeptide,
wherein the BacNav prokaryotic ion channel polypeptide is expressed in the cardiomyocytes of the subject,
wherein the voltage gated ion channel-related condition is selected from heart arrhythmia, chronic atrial fibrillation, damage from myocardial infarction, heart damage from stroke, and chronic ischemia,
wherein the BacNav prokaryotic ion channel polypeptide comprises the amino acid sequence of SEQ ID NO: 24, and
wherein the voltage gated ion channel-related condition in the subject is treated.

2. The method of claim 1, wherein the vector comprises the polynucleotide sequence of SEQ ID NO: 25.

3. The method of claim 1, wherein the vector is administered to the subject in a pharmaceutical composition comprising the vector and a pharmaceutically acceptable carrier.

4. The method of claim 1, wherein the subject is a rat.

5. The method of claim 1, wherein the subject is a primate.

6. The method of claim 1, wherein the subject is a human.

7. A method of increasing the conductivity of a cardiac tissue of a subject, the method comprising administering directly to the heart of the subject by injection a recombinant AAV9 vector encoding a BacNav prokaryotic ion channel polypeptide,
wherein the subject is a mammal and has a condition selected from heart arrhythmia, chronic atrial fibrillation, damage from myocardial infarction, heart damage from stroke, and chronic ischemia,
wherein the vector comprises a promoter that directs expression of the BacNav prokaryotic ion channel polypeptide,
wherein the BacNav prokaryotic ion channel polypeptide is expressed in the cardiomyocytes of the subject,
wherein the BacNav prokaryotic ion channel polypeptide comprises the amino acid sequence of SEQ ID NO: 24, and
wherein the conductivity of the cardiac tissue in the subject is increased.

8. A method of increasing the resistance to conduction block of a cardiac tissue of a subject, the method comprising administering directly to the heart of the subject by injection a recombinant AAV9 vector encoding a BacNav prokaryotic ion channel polypeptide,
wherein the subject is a mammal and has a condition selected from heart arrhythmia, chronic atrial fibrillation, damage from myocardial infarction, heart damage from stroke, and chronic ischemia,
wherein the vector comprises a promoter that directs expression of the BacNav prokaryotic ion channel polypeptide,
wherein the BacNav prokaryotic ion channel polypeptide is expressed in the cardiomyocytes of the subject,
wherein the BacNav prokaryotic ion channel polypeptide comprises the amino acid sequence of SEQ ID NO: 24, and
wherein the resistance to conduction block of the cardiac tissue in the subject is increased.

9. A method of increasing the upstroke velocity of a cardiac tissue of a subject, the method comprising administering directly to the heart of the subject by injection a recombinant AAV9 vector encoding a BacNav prokaryotic ion channel polypeptide,
wherein the subject is a mammal and has a condition selected from heart arrhythmia, chronic atrial fibrillation, damage from myocardial infarction, heart damage from stroke, and chronic ischemia,
wherein the vector comprises a promoter that directs expression of the BacNav prokaryotic ion channel polypeptide,
wherein the BacNav prokaryotic ion channel polypeptide is expressed in the cardiomyocytes of the subject,
wherein the BacNav prokaryotic ion channel polypeptide comprises the amino acid sequence of SEQ ID NO: 24, and
wherein the upstroke velocity of the cardiac tissue in the subject is increased.

* * * * *